US012668834B2

(12) United States Patent
Naji et al.

(10) Patent No.: US 12,668,834 B2
(45) **Date of Patent: *Jun. 30, 2026**

(54) STRAND DISPLACING AMPLIFICATION ENZYMES

(71) Applicant: Singular Genomics Systems, Inc., San Diego, CA (US)

(72) Inventors: Souad Naji, La Jolla, CA (US); Eli N. Glezer, Del Mar, CA (US); Bruna Krebs Kutche, San Diego, CA (US); Ali Nikoomanzar, San Diego, CA (US); Alexander Sevy, San Diego, CA (US); Caleb Newman, San Diego, CA (US); Ryan Shultzaberger, San Diego, CA (US); Abrehet Abdu, San Diego, CA (US); Youngjin Cho, San Diego, CA (US); Janell J. Kosmatka, Encinitas, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 582 days.

This patent is subject to a terminal disclaimer.

(21) Appl. No.: 18/145,007

(22) Filed: Dec. 21, 2022

(65) Prior Publication Data

US 2023/0257803 A1 Aug. 17, 2023

Related U.S. Application Data

(60) Provisional application No. 63/292,890, filed on Dec. 22, 2021.

(51) Int. Cl.

*C12Q 1/6844* (2018.01)
*C12N 9/12* (2006.01)
*C12Q 1/6811* (2018.01)
*C12Q 1/686* (2018.01)

(52) U.S. Cl.

CPC ......... *C12Q 1/6844* (2013.01); *C12N 9/1247* (2013.01); *C12Q 1/6811* (2013.01)

(58) Field of Classification Search

CPC ..... C12Q 1/6844; C12Q 1/686; C12N 9/1247
See application file for complete search history.

(56) References Cited

U.S. PATENT DOCUMENTS 4,318,846 A 3/1982 Khanna et al.
5,034,506 A 7/1991 Summerton et al.
5,066,580 A 11/1991 Lee
5,188,934 A 2/1993 Menchen et al.
5,235,033 A 8/1993 Summerton et al.
5,366,860 A 11/1994 Bergot et al.
5,599,675 A 2/1997 Brenner
5,688,648 A 11/1997 Mathies et al.
5,750,341 A 5/1998 Macevicz
5,756,334 A 5/1998 Perler et al.
5,763,954 A 6/1998 Hiatt et al.
5,800,996 A 9/1998 Lee et al.
5,808,045 A 9/1998 Hiatt et al.
5,847,162 A 12/1998 Lee et al.
5,872,244 A 2/1999 Hiatt et al.
6,210,891 B1 4/2001 Nyren et al.
6,232,465 B1 5/2001 Hiatt et al.
6,258,568 B1 7/2001 Nyren
6,274,320 B1 8/2001 Rothberg et al.
6,465,254 B1 10/2002 Saito et al.
6,664,079 B2 12/2003 Ju et al.
7,057,026 B2 6/2006 Barnes et al.
7,541,170 B2 6/2009 Wang et al.
7,541,444 B2 6/2009 Milton et al.
8,114,973 B2 2/2012 Siddiqi et al.
8,178,360 B2 5/2012 Barnes et al.
10,041,115 B2 8/2018 Stupi et al.
10,738,072 B1 8/2020 Graham et al.
11,034,942 B1 6/2021 Naji et al.
11,136,565 B2 10/2021 Naji et al.
11,174,281 B1 11/2021 Graham et al.
11,845,923 B2 12/2023 Naji et al.
11,851,687 B2 12/2023 Naji et al.
11,884,943 B2 1/2024 Naji et al.
11,891,633 B2 2/2024 Naji et al.
12,344,867 B2 7/2025 Naji et al.
12,454,683 B2 10/2025 Naji et al.
2004/0191825 A1 9/2004 Wang et al.
2005/0266439 A1 12/2005 Hjorleifsdottir et al.
2006/0240439 A1 10/2006 Smith et al.
2011/0045489 A1 2/2011 Gardner et al.
2013/0012399 A1 1/2013 Myers et al.
2015/0140561 A1 5/2015 Bergmann et al.
2016/0090579 A1 3/2016 Bomati et al.
2017/0022553 A1 1/2017 Vijayan et al.

(Continued)

FOREIGN PATENT DOCUMENTS

WO 1989010977 A1 11/1989
WO 1996007669 A1 3/1996

(Continued)

OTHER PUBLICATIONS

Abil, Z. et al. (Apr. 9, 2018, e-published Mar. 2018). "Compartmentalized Self-Replication for Evolution of a DNA Polymerase," *Current Protocols in Chemical Biology* 10: 1-17.
Bentley, D. R. et al. (Nov. 6, 2008). "Accurate whole human genome sequencing using reversible terminator chemistry," *Nature* 456(7218): 53-59.
Bergen, K. et al. (Jun. 17, 2013, e-published Jun. 3, 2013). "Structures of KOD and 9°N DNA polymerases complexed with primer template duplex," Chembiochem 14(9): 1058-1062.
Buchfink, B. et al. (Jan. 2015, e-published Nov. 17, 2014). "Fast and sensitive protein alignment using DIAMOND," *Nature methods* 12(1): 59-60.
Fire, A. et al. (May 9, 1995). "Rolling replication of short DNA circles," PNAS USA 92(10): 4641-4645.

(Continued)

*Primary Examiner* — Maryam Monshipouri
(74) *Attorney, Agent, or Firm* — Mintz, Levin, Cohn, Ferris, Glovsky and Popeo, P.C.; Zachary L. Terranova

(57) ABSTRACT

Disclosed herein, inter alia, are novel strand-displacing polymerases and methods of use thereof.

21 Claims, 1 Drawing Sheet

Specification includes a Sequence Listing.

(56) References Cited

U.S. PATENT DOCUMENTS

| | | | |
|---|---|---|---|
| 2017/0130051 A1 | 5/2017 | Marma et al. |
| 2017/0298327 A1 | 10/2017 | Bomati et al. |
| 2019/0048404 A1 | 2/2019 | Dambacher |
| 2020/0080065 A1 | 3/2020 | Fuller et al. |
| 2023/0011240 A1 | 1/2023 | Fuller et al. |
| 2023/0203578 A1 | 6/2023 | Naji et al. |
| 2023/0257803 A1 | 8/2023 | Naji et al. |
| 2024/0200041 A1 | 6/2024 | Naji et al. |

FOREIGN PATENT DOCUMENTS

| | | | |
|---|---|---|---|
| WO | 2004018497 A2 | 3/2004 |
| WO | 2005024010 A1 | 3/2005 |
| WO | 2009131919 A1 | 10/2009 |
| WO | 2015148402 A1 | 10/2015 |
| WO | 2017058953 A1 | 4/2017 |
| WO | 2017205336 A1 | 11/2017 |
| WO | 2018148723 A1 | 8/2018 |
| WO | 2019164977 A1 | 8/2019 |
| WO | 2020056044 A1 | 3/2020 |
| WO | 2021173711 A2 | 9/2021 |

OTHER PUBLICATIONS

Fogg, M. J. et al. (Dec. 1, 2002, e-published Nov. 4, 2002). "Structural basis for uracil recognition by archaeal family B DNA polymerases," *Nature structural biology* 9(12): 922-927.

Fuller, C.W. et al. (May 10, 2016, e-published Apr. 18, 2016). "Real-time single-molecule electronic DNA sequencing by synthesis using polymer-tagged nucleotides on a nanopore array," PNAS USA 113(19): 5233-5238.

Gibson, D. G. et al. (May 2009, e-published Apr. 12, 2009). "Enzymatic assembly of DNA molecules up to several hundred kilobases," *Nature methods* 6(5): 343-345.

Gibson, D. G. et al. (Oct. 10, 2010). "Chemical synthesis of the mouse mitochondrial genome," *Nature methods* 7(11): 901-903.

Guo, J. et al. (Jul. 8, 2008, e-published Jun. 30, 2008). "Four-color DNA sequencing with 3'- O-modified nucleotide reversible terminators and chemically cleavable fluorescent dideoxynucleotides," PNAS USA 105(27): 9145-9150.

Harris, C. L. et al. (Feb. 2013, e-published Apr. 3, 2018). "Polymerase chain displacement reaction," *Biotechniques* 54(2): 93-97.

Kumar, S. et al. (Sep. 21, 2012). "PEG-labeled nucleotides and nanopore detection for single molecule DNA sequencing by synthesis," *Scientific Reports* 2: Article 684, 8 pages.

Lage, J. M. et al. (2003). "Whole genome analysis of genetic alterations in small DNA samples using hyperbranched strand displacement amplification and array—CGH," *Genome research* 13(2): 294-307.

Lasken, R. S. et al. (Jul. 1996). "Archaebacterial DNA polymerases tightly bind uracil-containing DNA," *Journal of Biological Chemistry* 271(30): 17692-17696.

Lizardi, P. M. et al. (Jul. 1998). "Mutation detection and single-molecule counting using isothermal rolling-circle amplification," *Nature genetics* 19(3): 225-232.

Loeb, L. A. et al. (Aug. 2008, e-published Jul. 15, 2008). "DNA polymerases and human disease," *Nature Reviews Genetics* 9(8): 594-604.

Needleman, S. B. et al. (Mar. 28, 1970, e-published Oct. 28, 2004). "A general method applicable to the search for similarities in the amino acid sequence of two proteins," *Journal of molecular biology* 48(3): 443-453.

Nilsson, M. et al. (Sep. 1994). "Padlock probes: circularizing oligonucleotides for localized DNA detection," *Science* 265(5181): 2085-2088.

Nørholm, M. H. H. (Mar. 16, 2010). "A mutant Pfu DNA polymerase designed for advanced uracil-excision DNA engineering," *BMC biotechnology* 10: Article 21, 7 pages.

Notomi, T. et al. (Jun. 15, 2000). "Loop-mediated isothermal amplification of DNA," *Nucleic acids research* 28(12): e63.

Pearson, W. R. et al. (Apr. 1, 1988). "Improved tools for biological sequence comparison," *PNAS USA* 85(8): 2444-2448.

Smith, T. F. et al. (Dec. 1981, e-published Sep. 3, 2004). "Comparison of biosequences," *Advances in applied mathematics* 2(4): 482-489.

Southworth, M. W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," *PNAS USA* 93(11):5281-5285.

Untergasser, A. et al. (Aug. 1, 2012, e-published Jun. 22, 2012). "Primer3—new capabilities and interfaces," *Nucleic acids research* 40(15): e115.

Walker, G. T. et al. (Apr. 11, 1992). "Strand displacement amplification-an isothermal, in vitro DNA amplification technique," *Nucleic acids research* 20(7): 1691-1696.

Walker, G. T. et al. (Jan. 1, 1992). "Isothermal in vitro amplification of DNA by a restriction enzyme/DNA polymerase system," *PNAS USA* 89(1): 392-396.

Williams, R. et al. (Jul. 2006). "Amplification of complex gene libraries by emulsion PCR," *Nature methods* 3(7): 545-550.

Xu, G. et al. (Feb. 3, 2012). "Cross priming amplification: mechanism and optimization for isothermal DNA amplification," *Scientific reports* 2(1): Article 246, 7 pages.

Extended European Search Report issued in European Application 19859131.5, mailed on May 11, 2022, 7 pages.

Extended European Search Report issued in European Patent Application No. 21761816.4, mailed on, May 27, 2024, 10 pages.

International Search Report and Written Opinion issued in International Application No. PCT/US2021/019466, mailed on, Aug. 17, 2021, 11 pages.

International Search Report and Written Opinion issued in International Application No. PCT/US2019/050678, mailed on Jan. 28, 2020, 12 pages.

USPTO Sequence Alignment search for SEQ ID No. 1, performed Oct. 11, 2024, Oct. 11, 2024, 3 pages.

Aird, D. et al. (Feb. 11, 2011). "Analyzing and minimizing PCR amplification bias in Illumina sequencing libraries," Genome biology 12: R18, 14 pages.

Bains, W. et al. (Dec. 7, 1988). "A novel method for nucleic acid sequence determination," Journal of Theoretical Biology 135(3): 303-307.

Drmanac, S. et al. (Jan. 1, 1998). "Accurate sequencing by hybridization for DNA diagnostics and individual genomics," Nature Biotechnology 16(1): 54-58.

Fodor, S. P. A. et al. (Feb. 15, 1991). "Light-directed, spatially addressable parallel chemical synthesis," Science 251(4995): 767-773.

Gueguen, Y. et al. (Dec. 20, 2001). "Characterization of two DNA polymerases from the hyperthermophilic euryarchaeon *Pyrococcus abyssi*," European Journal of Biochemistry 268(22): 5961-5969.

Hutter, D. et al. (Dec. 1, 2010). "Labeled nucleoside triphosphates with reversibly terminating aminoalkoxyl groups," Nucleosides, Nucleotides and Nucleic Acids 29(11-12): 879- 895.

Jakobsen, T. H. et al. (Jul. 22, 2013). "Complete genome sequence of the cystic fibrosis pathogen Achromobacter xylosoxidans NH44784-1996 complies with important pathogenic phenotypes," PloS one 8(7): e68484.

Ju, J. et al. (Dec. 26, 2006). "Four-color DNA sequencing by synthesis using cleavable fluorescent nucleotide reversible terminators," PNAS USA 103(52): 19635-19640.

Killelea, T. et al. (Jun. 14, 2011, e-published May 20, 2011). "Role of Disulfide Bridges in Archaeal Family-B DNA Polymerases," ChemBioChem 12(9): 1330-1336.

Kisselev, L. (Jan. 2002) "Polypeptide Release Factors in Prokaryotes and Eukaryotes: Same Function, Different Structure", Structure, 10(1):8-9.

Lizardi et al. (Jul. 19, 1998) "Mutation Detection and Single-Molecule Counting Using Isothermal Rolling—Circle Amplification", Nature Genetics, 19(3):225-232.

Plasterer, Thomas N. (1997) "PRIMERSELECT. Primer and Probe Design", Methods in Molecular Biology, 70:291-302.

(56) References Cited

OTHER PUBLICATIONS

Ronaghi, M. et al. (Nov. 1, 1996). "Real-time DNA sequencing using detection of pyrophosphate release," Analytical Biochemistry 242(1): 84-89.
Ronaghi, M. et al. (Jul. 17, 1998). "A sequencing method based on real-time pyrophosphate," Science 281(5375): 363-365.
Ronaghi, M. (Jan. 2001). "Pyrosequencing sheds light on DNA sequencing," Genome Research 11(1): 3-11.
Rosenblum, B. B. et al. (Nov. 1, 1997). "New dye-labeled terminators for improved DNA sequencing patterns," Nucleic Acids Research 25(22): 4500-4504.
Ruparel, H. et al. (Apr. 26, 2005, e-published Apr. 13, 2005). "Design and synthesis of a 3'-O-ally) photocleavable fluorescent nucleotide as a reversible terminator for DNA sequencing by synthesis," PNAS USA 102(17): 5932-5937.
Rychlik, Wojciech (2007) "OLIGO 7 Primer Analysis Software", Methods in Molecular Biology, 402:35-60.
Shendure, J. et al. (Sep. 9, 2005, e-published Aug. 4, 2005). "Accurate multiplex polony sequencing of an evolved bacterial genome," Science 309(5741): 1728-1732.
Truniger et al. (Jan. 16, 2004) "Function of the C-Terminus Of @29 DNA Polymerase in DNA and Terminal Protein Binding", Nucleic Acids Research, 32(1): 361-370.
Whisstock et al. (Aug. 2003) "Prediction of Protein Function from Protein Sequence and Structure", Quarterly Reviews of Biophysics, 36(3):307-340.
Witkowski et al. (1999) "Conversion of a Beta-Ketoacyl Synthase to a Malonyl Decarboxylase by Replacement of the Active-Site Cysteine with Glutamine", Biochemistry, 38(36): 11643-11650.
Wu, J. et al. (Oct. 16, 2007). "3'-O-modified nucleotides as reversible terminators for pyrosequencing," PNAS USA 104(42): 16462-16467.
Yamaji et al. (Apr. 2015) "Mammalian Adaptive Mutations of the PA Protein of Highly Pathogenic Avian H5N1 Influenza Virus", Journal of Virology, 89(8):4117-4125.
Zhu, Z. et al. (Aug. 25, 1994). "Directly labeled DNA probes using fluorescent nucleotides with different length linkers," Nucleic Acids Research 22(16): 3418-3422.

| | Amino Acid position *P. horikoshii* | | | | | | | | | | | | | | | | | | | |
|---|---|---|---|---|---|---|---|---|---|---|---|---|---|---|---|---|---|---|---|---|
| | **541** | **542** | **543** | **544** | **545** | **546** | **547** | **548** | **549** | **550** | **551** | **552** | **553** | **554** | **555** | **556** | **557** | **558** | **559** | **560** |
| | | | | | | | | | | | | | | | | | | | | |
| P. horikoshii (SEQ ID NO:1) | T | D | G | L | Y | A | T | I | P | G | V | K | D | W | E | E | V | K | R | R |
| P. abyssi (SEQ ID NO:3) | T | D | G | L | Y | A | T | I | P | G | A | K | H | - | E | E | I | K | E | K |
| | **541** | **542** | **543** | **544** | **545** | **546** | **547** | **548** | **549** | **550** | **551** | **552** | **553** | | **554** | **555** | **556** | **557** | **558** | **559** |
| | Amino Acid position *P. abyssi* | | | | | | | | | | | | | | | | | | | |

SEQUENCE LISTING

```
Sequence total quantity: 12
SEQ ID NO: 1              moltype = AA  length = 775
FEATURE                   Location/Qualifiers
source                    1..775
                          mol_type = protein
                          organism = Pyrococcus horikoshii
SEQUENCE: 1
MILDADYITE DGKPIIRIFK KENGEFKVEY DRNFRPYIYA LLRDDSAIDE IKKITAQRHG  60
KVVRIVETEK IQRKFLGRPI EVWKLYLEHP QDVPAIRDKI REHPAVVDIF EYDIPFAKRY  120
LIDKGLTPME GNEKLTFLAV DIETLYHEGE EFGKGPVIMI SYADEEGAKV ITWKKIDLPY  180
```

-continued

```
VEVVSSEREM IKRLIRVIKE KDPDVIITYN GDNFDFPYLL KRAEKLGIKL LLGRDNSEPK  240
MQKMGDSLAV EIKGRIHFDL FPVIRRTINL PTYTLEAVYE AIFGKPKEKV YADEIAKAWE  300
TGEGLERVAK YSMEDAKVTY ELGREFFPME AQLARLVGQP VWDVSRSSTG NLVEWFLLRK  360
AYERNELAPN KPDEKEYERR LRESYEGGYV KEPEKGLWEG IVSLDFRSLY PSIIITHNVS  420
PDTLNREGCE EYDVAPKVGH RFCKDFPGFI PSLLGQLLEE RQKIKKRMKE SKDPVEKKLL  480
DYRQRAIKIL ANSYYGYYGY AKARWYCKEC AESVTAWGRQ YIDLVRRELE ARGFKVLYID  540
TDGLYATIPG VKDWEEVKRR ALEFVDYINS KLPGVLELEY EGFYARGFFV TKKKYALIDE  600
EGKIVTRGLE IVRRDWSEIA KETQARVLEA ILKHGNVEEA VKIVKDVTEK LTNYEVPPEK  660
LVIYEQITRP INEYKAIGPH VAVAKRLMAR GIKVKPGMVI GYIVLRGDGP ISKRAISIEE  720
FDPRKHKYDA EYYIENQVLP AVERILKAFG YKREDLRWQK TKQVGLGAWI KVKKS       775

SEQ ID NO: 2           moltype = DNA  length = 2328
FEATURE                Location/Qualifiers
source                 1..2328
                       mol_type = other DNA
                       organism = Pyrococcus horikoshii
SEQUENCE: 2
atgattctgg acgctgatta tattactgaa gatggtaaac cgattattcg tatttttaaa  60
aaagaaaatg gcgagttcaa agttgaatat gaccgtaact ttcgtccgta catctacgcg  120
ctgttgcgcg acgatagcgc gatcgatgag attaagaaaa ttaccgcgca gcgtcatggt  180
aaagttgttc gcatcgttga aaccgagaaa attcaacgta aattcctggg ccgcccaatt  240
gaagtgtgga agctgtacct ggagcatccg caagatgtcc cggcgatccg tgacaagatt  300
cgcgagcacc cggccgtcgt cgacattttc gaatacgata ttccgttcgc aaagcgttac  360
ctgatcgata agggtctgac cccgatggag ggtaatgaaa agctgacgtt cctggctgtc  420
gatattgaaa cgttgtacca cgagggtgaa gagtttggta agggcccggt cattatgatc  480
agctacgcgg atgaagaggg cgccaaagtt atcacgtgga aaaaaattga tctgccgtac  540
gttgaagttg tgtccagcga gcgcgagatg attaaacgct tgattcgtgt gattaaagaa  600
aaagatccag acgtgatcat tacctataat ggtgacaact ttgactttcc gtacttgctg  660
aaacgtgctg agaaactggg tatcaagctg ttgctgggtc gcgataatag cgagccgaag  720
atgcaaaaaa tgggcgatag cctggcagtc gagatcaagg gtcgcatcca ctttgatctc  780
tttccggtga ttcgtcgcac gatcaatctg ccgacctata cgctggaagc tgtctacgag  840
gcaatctttg gtaagccgaa agaaaaagtc tatgcggacg aaattgcgaa agcgtgggaa  900
accggcgagg gcctggagcg tgtggcaaag tactctatgg aagatgccaa agtgacctat  960
gaactgggtc gtgagttctt cccaatggaa gcccagttgg cgcgcttggt gggccaaccg  1020
gtttgggacg tttcccgtag cagcaccggt aacctggttg agtggttcct gttgcgtaaa  1080
gcgtatgagc gtaatgaact ggcaccgaac aagcctgacg agaaagaata tgaacgtcgc  1140
ctgcgtgaat cttacgaggg tggttacgtc aaagaaccgg aaaagggtct gtgggaaggc  1200
atcgtgagcc tggatttccg tagcctgtac cctagcatca tcatcacgca caatgttagc  1260
ccggacaccc tgaaccgcga gggctgcgaa gagtacgacg ttgcgccgaa agtcggccat  1320
cgtttttgta aagacttccc tggtttcatc ccaagcctgc tgggtcagct gctggaagag  1380
agacagaaaa ttaaaaaacg catgaaagaa tcgaaagatc cggttgagaa aaagctgctg  1440
gattaccgcc agcgtgccat caagattctg gctaactcat attatggcta ctacggttat  1500
gctaaagcgc gttggtactg taaagagtgc gcggagtccg tcaccgcgtg ggtcgccag  1560
tatatcgatc tggtgcgtcg cgagctggaa gcgcgtggtt ttaaggtcct gtacatcgat  1620
actgacggtc tgtatgcaac catccctggt gtcaaagact gggaagaggt taagcgtcgt  1680
gcactggaat ttgtggacta tatcaattct aagttgccgg gtgtgctgga gctggagtac  1740
gaaggcttct atgcacgcgg ctttttcgtt acgaaaaaga aatacgcact gatcgacgaa  1800
gagggcaaga ttgtgactcg tggtctggaa atcgttcgtc gcgactggag cgagattgca  1860
aaagaaaccc aagctcgcgt tctggaagca atcctgaaac atggtaacgt cgaagaagcc  1920
gtcaagatcg tgaaagatgt caccgaaaag ttgaccaact acgaagttcc accggaaaaa  1980
ctggtgattt atgagcaaat cacgcgtccg atcaatgaat ataaggccat tggcccgcac  2040
gtcgcggtgg ccaagcgcct gatggcgcgt ggtatcaaag tgaaaccggg tatggttatt  2100
ggttacatcg tgctgcgtgg cgacggcccg attagcaaac gtgcgatcag cattgaagaa  2160
tttgacccgc gtaagcacaa atatgacgcg gaatactata tcgagaatca agtgctgccg  2220
gccgtggaac gcattctgaa agctttcggc tacaagcgtg aagatttgcg ctggcagaaa  2280
accaaacagg ttggtcttgg tgcgtggatc aaggtcaaaa agtcctaa              2328

SEQ ID NO: 3           moltype = AA  length = 771
FEATURE                Location/Qualifiers
source                 1..771
                       mol_type = protein
                       organism = Pyrococcus sp.
SEQUENCE: 3
MIIDADYITE DGKPIIRIFK KEKGEFKVEY DRTFRPYIYA LLKDDSAIDE VKKITAERHG  60
KIVRITEVEK VQKKFLGRPI EVWKLYLEHP QDVPAIREKI REHPAVVDIF EYDIPFAKRY  120
LIDKGLTPME GNEELTFLAV DIETLYHEGE EFGKGPIIMI SYADEEGAKV ITWKSIDLPY  180
VEVVSSEREM IKRLVKVIRE KDPDVIITYN GDNFDFPYLL KRAEKLGIKL PLGRDNSEPK  240
MQRMGDSLAV EIKGRIHFDL FPVIRRTINL PTYTLEAVYE AIFGKSKEKV YAHEIAEAWE  300
TGKGLERVAK YSMEDAKVTF ELGKEFFPME AQLARLVGQP VWDVSRSSTG NLVEWFLLRK  360
AYERNELAPN KPDEREYERR LRESYEGGYV KEPEKGLWEG IVSLDFRSLY PSIIITHNVS  420
PDTLNRENCK EYDVAPQVGH RFCKDFPGFI PSLLGNLLEE RQKIKKRMKE SKDPVEKKLL  480
DYRQRAIKIL ANSYYGYYGY AKARWYCKEC AESVTAWGRQ YIDLVRRELE SRGFKVLYID  540
TDGLYATIPG AKHEEIKEKA LKFVEYINSK LPGLLELEYE GFYARGFFVT KKKYALIDEE  600
GKIVTRGLEI VRRDWSEIAK ETQAKVLEAI LKHGNVDEAV KIVKEVTEKL SKYEIPPEKL  660
VIYEQITRPL SEYKAIGPHV AVAKRLAAKG VKVKPGMVIG YIVLRGDGPI SKRAIAIEEF  720
DPKKHKYDAE YYIENQVLPA VERILRAFGY RKEDLKYQKT KQVGLGAWLK F          771

SEQ ID NO: 4           moltype = AA  length = 775
FEATURE                Location/Qualifiers
```

```
source                  1..775
                        mol_type = protein
                        organism = Pyrococcus woesei
SEQUENCE: 4
MILDVDYITE EGKPVIRLFK KENGKFKIEH DRTFRPYIYA LLRDDSKIEE VKKITGERHG  60
KIVRIVDVEK VEKKFLGKPI TVWKLYLEHP QDVPTIREKV REHPAVVDIF EYDIPFAKRY  120
LIDKGLIPME GEEELKILAF DIETLYHEGE EFGKGPIIMI SYADENEAKV ITWKNIDLPY  180
VEVVSSEREM IKRFLRIIRE KDPDIIVTYN GDSFDFPYLA KRAEKLGIKL TIGRDGSEPK  240
MQRIGDMTAV EVKGRIHFDL YHVITRTINL PTYTLEAVYE AIFGKPKEKV YADEIAKAWE  300
SGENLERVAK YSMEDAKATY ELGKEFLPME IQLSRLVGQP LWDVSRSSTG NLVEWFLLRK  360
AYERNEVAPN KPSEEEYQRR LRESYTGGFV KEPEKGLWEN IVYLDFRALY PSIIITHNVS  420
PDTLNLEGCK NYDIAPQVGH KFCKDIPGFI PSLLGHLLEE RQKIKTKMKE TQDPIEKILL  480
DYRQKAIKLL ANSFYGYYGY AKARWYCKEC AESVTAWGRK YIELVWKELE EKFGFKVLYI  540
DTDGLYATIP GGESEEIKKK ALEFVKYINS KLPGLLELEY EGFYKRGFFV TKKRYAVIDE  600
EGKVITRGLE IVRRDWSEIA KETQARVLET ILKHGDVEEA VRIVKEVIQK LANYEIPPEK  660
LAIYEQITRP LHEYKAIGPH VAVAKKLAAK GVKIKPGMVI GYIVLRGDGP ISNRAILAEE  720
YDPKKHKYDA EYYIENQVLP AVLRILEGFG YRKEDLRYQK TRQVGLTSWL NIKKS       775

SEQ ID NO: 5            moltype = AA  length = 775
FEATURE                 Location/Qualifiers
source                  1..775
                        mol_type = protein
                        organism = Pyrococcus furiosus
SEQUENCE: 5
MILDVDYITE EGKPVIRLFK KENGKFKIEH DRTFRPYIYA LLRDDSKIEE VKKITGERHG  60
KIVRIVDVEK VEKKFLGKPI TVWKLYLEHP QDVPTIREKV REHPAVVDIF EYDIPFAKRY  120
LIDKGLIPME GEEELKILAF DIETLYHEGE EFGKGPIIMI SYADENEAKV ITWKNIDLPY  180
VEVVSSEREM IKRFLRIIRE KDPDIIVTYN GDSFDFPYLA KRAEKLGIKL TIGRDGSEPK  240
MQRIGDMTAV EVKGRIHFDL YHVITRTINL PTYTLEAVYE AIFGKPKEKV YADEIAKAWE  300
SGENLERVAK YSMEDAKATY ELGKEFLPME IQLSRLVGQP LWDVSRSSTG NLVEWFLLRK  360
AYERNEVAPN KPSEEEYQRR LRESYTGGFV KEPEKGLWEN IVYLDFRALY PSIIITHNVS  420
PDTLNLEGCK NYDIAPQVGH KFCKDIPGFI PSLLGHLLEE RQKIKTKMKE TQDPIEKILL  480
DYRQKAIKLL ANSFYGYYGY AKARWYCKEC AESVTAWGRK YIELVWKELE EKFGFKVLYI  540
DTDGLYATIP GGESEEIKKK ALEFVKYINS KLPGLLELEY EGFYKRGFFV TKKRYAVIDE  600
EGKVITRGLE IVRRDWSEIA KETQARVLET ILKHGDVEEA VRIVKEVIQK LANYEIPPEK  660
LAIYEQITRP LHEYKAIGPH VAVAKKLAAK GVKIKPGMVI GYIVLRGDGP ISNRAILAEE  720
YDPKKHKYDA EYYIENQVLP AVLRILEGFG YRKEDLRYQK TRQVGLTSWL NIKKS       775

SEQ ID NO: 6            moltype = AA  length = 775
FEATURE                 Location/Qualifiers
source                  1..775
                        mol_type = protein
                        organism = Pyrococcus glycovorans
SEQUENCE: 6
MILDADYITE DGKPIIRIFK KENGEFKVEY DRNFRPYIYA LLKDDSQIDE VKKITAERHG  60
KIVRIVDVEK VKKKFLGRPI EVWKLYFEHP QDVPAIRDKI REHPAVVDIF EYDIPFAKRY  120
LIDKGLIPME GDEELKLLAF DIETLYHEGE EFAKGPIIMI SYADEEGAKV ITWKKVDLPY  180
VEVVSSEREM IKRFLKVIRE KDPDVIITYN GDSFDLPYLV KRAEKLGIKL PLGRDGSEPK  240
MQRLGDMTAV EIKGRIHFDL YHVIRRTINL PTYTLEAVYE AIFGKPKEKV YAHEIAEAWE  300
TGKGLERVAK YSMEDAKVTY ELGREFFPME AQLSRLVGQP LWDVSRSSTG NLVEWYLLRK  360
AYERNELAPN KPDEREYERR LRESYAGGYV KEPEKGLWEG LVSLDFRSLY PSIIITHNVS  420
PDTLNREGCM EYDVAPEVKH KFCKDFPGFI PSLLKRLLDE RQEIKRRMKA SKDPIEKKML  480
DYRQRAIKIL ANSYYGYYGY AKARWYCKEC AESVTAWGRE YIEFVRKELE EKFGFKVLYI  540
DTDGLYATIP GAKPEEIKRK ALEFVEYINA KLPGLLELEY EGFYVRGFFV TKKKYALIDE  600
EGKIITRGLE IVRRDWSEIA KETQAKVLEA ILKHGNVEEA VKIVKEVTEK LSKYEIPPEK  660
LVIYEQITRP LHEYKAIGPH VAVAKRLAAR GVKVRPGMVI GYIVLRGDGP ISKRAILAEE  720
FDPRKHKYDA EYYIENQVLP AVLRILEAFG YRKEDLRWQK TKQTGLTAWL NVKKK       775

SEQ ID NO: 7            moltype = AA  length = 775
FEATURE                 Location/Qualifiers
source                  1..775
                        mol_type = protein
                        organism = Pyrococcus sp.
SEQUENCE: 7
MILDADYITE DGKPIIRLFK KENGRFKVEY DRNFRPYIYA LLKDDSAIDD VRKITSERHG  60
KVVRVIDVEK VKKKFLGRPI EVWKLYFEHP QDVPAMRDKI REHPAVIDIF EYDIPFAKRY  120
LIDKGLIPME GNEELTFLAV DIETLYHEGE EFGKGPIIMI SYADEEGAKV ITWKKIDLPY  180
VEVVANEREM IKRLIKVIRE KDPDVIITYN GDNFDFPYLL KRAEKLGMKL PLGRDNSEPK  240
MQRLGDSLAV EIKGRIHFDL FPVIRRTINL PTYTLEAVYE AIFGKQKEKV YPHEIAEAWE  300
TGKGLERVAK YSMEDAKVTY ELGKEFFPME AQLARLVGQP LWDVSRSSTG NLVEWYLLRK  360
AYERNELAPN KPDEREYERR LRESYEGGYV KEPERGLWEG IVSLDFRSLY PSIIITHNVS  420
PDTLNKEGCG EYDEAPEVGH RFCKDFPGFI PSLLGSLLEE RQKIKKRMKE SKDPVERKLL  480
DYRQRAIKIL ANSFYGYYGY AKARWYCKEC AESVTAWGRQ YIELVRRELE ERGFKVLYID  540
TDGLYATIPG EKNWEEIKRR ALEFVNYINS KLPGILELEY EGFYTRGFFV TKKKYALIDE  600
EGKIVTRGLE IVRRDWSEIA KETQAKVLEA ILKHGNVEEA VKIVKEVTEK LSNYEIPVEK  660
LVIYEQITRP LNEYKAIGPH VAVAKRLAAK GIKIKPGMVI GYVVLRGDGP ISKRAIAIEE  720
FDGKKHKYDA EYYIENQVLP AVERILKAFG YKREDLRWQK TKQVGLGAWL KVKKS       775

SEQ ID NO: 8            moltype = AA  length = 759
```

-continued

```
FEATURE                 Location/Qualifiers
source                  1..759
                        mol_type = protein
                        organism = Pyrococcus sp.
SEQUENCE: 8
MILDADYITE NGKPIIRLFK KENGKFKVEY DRNFRPYIYA LLKDDSAIDD VRKITSERHG  60
KVVRVIDVEK VSKKFLGRPI EVWKLYFEHP QDVPAIRDKI REHPAVIDIF EYDIPFAKRY  120
LIDKGLIPME GNEELSFLAV DIETLYHEGE EFGKGPIIMI SYADEEGAKV ITWKKIDLPY  180
VEVVANEREM IKRLVRIIRE KDPDIIITYN GDNFDFPYLL KRAEKLGIKL PLGRDNSEPK  240
MQRLGESLAV EIKGRIHFDL FPVIRRTINL PTYTLRTVYE AIFGKPKEKV YPHEIAEAWE  300
TGKGLERVAK YSMEDAKVTY ELGKEFFPME AQLARLVGQP VWDVSRSSTG NLVEWFLLRK  360
AYERNELAPN KPDEKEYEKR LRESYEGGYV KEPEKGLWEG IVSLDFRSLY PSIIITHNVS  420
PDTLNREGCG KYDEAPEVGH RFCKDFPGFI PSLLGDLLEE RQKIKKRMKE SKDPIEKKLL  480
DYRQRAIKIL ANSFYGYYGY AKARWYCKEC AESVTAWGRQ YIELVRRELE ERGFKVLYID  540
TDGLYATIPG EKNWEEIKRK ALEFVNYINS KLPGILELEY EGFYTRGFFV TKKKYALIDE  600
EGKIITRGLE IVRRDWSEIA KETQAKVLEA ILKHGNVEEA VKIVKEVTEK LSNYEIPVEK  660
LVIYEQITRP LNEYKAIGPH VAVAKRLAAK GIKIKPGMVI GYVLLRGDGP ISKRAIAIEE  720
FDGKKHKYDA EYYIENQVLP AVERILKAFG YKKEDLRWQ                        759

SEQ ID NO: 9            moltype = AA  length = 775
FEATURE                 Location/Qualifiers
source                  1..775
                        mol_type = protein
                        organism = Pyrococcus sp.
SEQUENCE: 9
MILDADYITE DGKPIIRIFK KENGEFKVEY DRNFRPYIYA LLKDDSQIDE VRKITAERHG  60
KIVRIIDAEK VRKKFLGRPI EVWRLYFEHP QDVPAIRDKI REHSAVIDIF EYDIPFAKRY  120
LIDKGLIPME GDEELKLLAF DIETLYHEGE EFAKGPIIMI SYADEEEAKV ITWKKIDLPY  180
VEVVSSEREM IKRFLKVIRE KDPDVIITYN GDSFDLPYLV KRAEKLGIKL PLGRDGSEPK  240
MQRLGDMTAV EIKGRIHFDL YHVIRRTINL PTYTLEAVYE AIFGKPKEKV YAHEIAEAWE  300
TGKGLERVAK YSMEDAKVTY ELGREFFPME AQLSRLVGQP LWDVSRSSTG NLVEWYLLRK  360
AYERNELAPN KPDEREYERR LRESYAGGYV KEPEKGLWEG LVSLDFRSLY PSIIITHNVS  420
PDTLNREGCR EYDVAPEVGH KFCKDFPGFI PSLLKRLLDE RQEIKRKMKA SKDPIEKKML  480
DYRQRAIKIL ANSYYGYYGY AKARWYCKEC AESVTAWGRE YIEFVRKELE EKFGFKVLYI  540
DTDGLYATIP GAKPEEIKKK ALEFVDYINA KLPGLLELEY EGFYVRGFFV TKKKYALIDE  600
EGKIITRGLE IVRRDWSEIA KETQAKVLEA ILKHGNVEEA VKIVKEVTEK LSKYEIPPEK  660
LVIYEQITRP LHEYKAIGPH VAVAKRLAAR GVKVRPGMVI GYIVLRGDGP ISKRAILAEE  720
FDLRKHKYDA EYYIENQVLP AVLRILEAFG YRKEDLRWQK TKQTGLTAWL NIKKK       775

SEQ ID NO: 10           moltype = AA  length = 776
FEATURE                 Location/Qualifiers
source                  1..776
                        mol_type = protein
                        organism = Pyrococcus yayanosii
SEQUENCE: 10
MILDADYITE NGKPVVRIFK KENGEFKVEY DRSFRPYIYA LLRDDSAIED IKKITAERHG  60
KVVRVVEAEK VRKKFLGRPI EVWKLYFEHP QDVPAIREKI REHPAVIDIF EYDIPFAKRY  120
LIDKGLIPME GNEELKLLAF DIETLYHEGD EFGSGPIIMI SYADEKGAKV ITWKGVDLPY  180
VEVVSSEREM IKRFLRVIRE KDPDVIITYN GDNFDFPYLL KRAEKLGMKL PIGRDGSEPK  240
MQRMGDGFAV EVKGRIHFDI YPVIRRTINL PTYTLEAVYE AVFGRPKEKV YPNEIARAWE  300
NCKGLERVAK YSMEDAKVTY ELGREFFPME AQLARLVGQP VWDVSRSSTG NLVEWFLLRK  360
AYERNELAPN RPDEREYERR LRESYEGGYV KEPEKGLWEG IIYLDFRSLY PSIIITHNIS  420
PDTLNKEGCN SYDVAPKVGH RFCKDFPGFI PSLLGQLLDE RQKIKRKMKA TIDPIERKLL  480
DYRQRAIKIL ANSYYGYYGY AKARWYCKEC AESVTAWGRE YIELVSRELE KRGFKVLYID  540
TDGLYATIPG SREWDKIKER ALEFVKYINA RLPGLLELEY EGFYKRGFFV TKKKYALIDE  600
EGKIITRGLE IVRRDWSEIA KETQARVLEA ILKEGNLEKA VKIVKEVTEK LSKYEVPPEK  660
LVIYEQITRD LKDYKAVGPH VAVAKRLAAR GIKVRPGMVI GYLVLRGDGP ISRRAIPAEE  720
FDPSRHKYDA EYYIENQVLP AVLRILEAFG YRKEDLRYQK TRQAGLDAWL KRKASL      776

SEQ ID NO: 11           moltype = AA  length = 774
FEATURE                 Location/Qualifiers
source                  1..774
                        mol_type = protein
                        organism = Pyrococcus sp.
SEQUENCE: 11
MILDADYITE DGKPVIRLFK KENGEFKIEY DRTFKPYIYA LLKDDSAIDE VRKVTAERHG  60
KIVRIIDVEK VKKKYLGRPI EVWKLYFEHP QDVPAIREKI REHPAVVEIF EYDIPFAKRY  120
LIDKGIVPMD GDEELKLLAF DIETLYHEGE EFGKGPILMI SYADEEGAKV ITWKRINLPY  180
VEVVSSEREM IKRFLKVIRE KDPDVIITYN GDSFDFPYLV KRAEKLGIKL PLGRDGSPPK  240
MQRLGDMNAV EIKGRIHFDL YHVVRRTINL PTYTLEAVYE AIFGKPKEKV YAHEIAEAWE  300
TGKGLERVAK YSMEDAQVTY ELGKEFFPME VQLTRLVGQP LWDVSRSSTG NLVEWYLLRK  360
AYERNELAPN KPDEREYERR LRESYAGGYV KEPERGLWEN IVYLDFRSLY PSIIITHNVS  420
PDTLNREGCR KYDIAPEVGH KFCKDVEGFI PSLLGHLLEE RQKIKRKMKA TINPVEKKLL  480
DYRQKAIKIL ANSYYGYYGY AKARWYCKEC AESVTAWGRE YIELVRKELE GKFGFKVLYI  540
DTDGLYATIP RGDPAEIKKK ALEFVRYINE KLPGLLELEY EGFYRRGFFV TKKKYALIDE  600
EDKIITRGLE IVRRDWSEIA KETQAKVLEA ILKEGNVEKA VKIVKEVTEK LMKYEVPPEK  660
LVIYEQITRP LNEYKAIGPH VAVAKRLAAK GVKVRPGMVI GYIVLRGDGP ISKRAILAEE  720
YDPRKNKYDA EYYIENQVLP AVLRILEAFG YKKEDLKYQK SRQVGLGAWI KVKK        774
```

-continued

```
SEQ ID NO: 12          moltype = AA  length = 775
FEATURE                Location/Qualifiers
source                 1..775
                       mol_type = protein
                       organism = Pyrococcus sp.
SEQUENCE: 12
MILDADYITE DGKPIIRIFK KENGEFKVEY DRNFRPYIYA LLKDDSQIDE VRKITAERHG  60
KIVRIIDAEK VRKKFLGRPI EVWRLYFEHP QDVPAIRDKI REHSAVIDIF EYDIPFAKRY  120
LIDKGLIPME GDEELKLLAF DIETLYHEGE EFAKGPIIMI SYADEEEAKV ITWKKIDLPY  180
VEVVSSEREM IKRFLKVIRE KDPDVIITYN GDSFDLPYLV KRAEKLGIKL PLGRDGSEPK  240
MQRLGDMTAV EIKGRIHFDL YHVIRRTINL PTYTLEAVYE AIFGKPKEKV YAHEIAEAWE  300
TGKGLERVAK YSMEDAKVTY ELGREFFPME AQLSRLVGQP LWDVSRSSTG NLVEWYLLRK  360
AYERNELAPN KPDEREYERR LRESYAGGYV KEPEKGLWEG LVSLDFRSLY PSIIITHNVS  420
PDTLNREGCR EYDVAPEVGH KFCKDFPGFI PSLLKRLLDE RQEIKRKMKA SKDPIEKKML  480
DYRQRAIKIL ANSYYGYYGY AKARWYCKEC AESVTAWGRE YIEFVRKELE EKFGFKVLYI  540
DTDGLYATIP GAKPEEIKKK ALEFVDYINA KLPGLLELEY EGFYVRGFFV TKKKYALIDE  600
EGKIITRGLE IVRRDWSEIA KETQAKVLEA ILKHGNVEEA VKIVKEVTEK LSKYEIPPEK  660
LVIYEQITRP LHEYKAIGPH VAVAKRLAAR GVKVRPGMVI GYIVLRGDGP ISKRAILAEE  720
FDLRKHKYDA EYYIENQVLP AVLRILEAFG YRKEDLRWQK TKQTGLTAWL NIKKK       775
```

STRAND DISPLACING AMPLIFICATION ENZYMES

CROSS-REFERENCES TO RELATED APPLICATIONS

This application claims the benefit of U.S. Provisional Application No. 63/292,890 filed on Dec. 22, 2021, which is incorporated herein by reference in its entirety and for all purposes.

REFERENCE TO SEQUENCE LISTING SUBMITTED ELECTRONICALLY

The Sequence Listing titled 051385-564001US_SL_ST26.XML, was created on Dec. 15, 2022 in machine format IBM-PC, MS-Windows operating system, is 21,959 bytes in size, and is hereby incorporated by reference in its entirety for all purposes.

BACKGROUND

Genetic analysis is taking on increasing importance in modern society as a diagnostic, prognostic, and as a forensic tool, and typically requires amplification of genomic fragments. A majority of nucleic acid amplification techniques (e.g., DNA amplification) used in university, medical, and clinical laboratory research is performed using the polymerase chain reaction (PCR), though in the past decade alternative amplification methods have emerged that eliminate thermal cycling (i.e., isothermal amplification). Typical isothermal amplification methods require the use of a DNA polymerase with a strong strand displacement activity to displace downstream DNA, thereby enabling continuous replication without thermal cycling. Efficient amplification typically requires elevated temperatures to enable the annealing of primers at specific locations on the dsDNA. However, few thermostable strand displacing enzymes exist. For example, SD DNA polymerase (a mutant Taq DNA polymerase) and the large fragment of Bst DNA polymerase possess favorable characteristics for isothermal amplification, but both are inactivated and elevated temperatures (e.g., greater than 70° C.). Thus, there is a need for thermostable, strand-displacing polymerases. Disclosed herein, inter alia, are solutions to these and other problems in the art.

BRIEF SUMMARY

In an aspect is provided a polymerase including an amino acid sequence that is at least 80% identical to a continuous 500 amino acid sequence within SEQ ID NO: 1; including a first mutation at amino acid position 588 or an amino acid position corresponding to position 588; wherein the first mutation is leucine, isoleucine, valine, alanine, or glycine; and a second mutation at amino acid position 7 or an amino acid position corresponding to position 7, wherein the second mutation is histidine, lysine, or arginine; a second mutation at amino acid position 97 or an amino acid position corresponding to position 97, wherein the second mutation is cysteine, histidine, lysine, serine, threonine, or methionine; or a second mutation at amino acid position 742 or an amino acid position corresponding to position 742, wherein the second mutation is leucine, isoleucine, alanine, or glycine.

In an aspect is provided a polymerase including an amino acid sequence that is at least 80% identical to a continuous 500 amino acid sequence within SEQ ID NO: 1; including a first mutation at amino acid position 97 or an amino acid position corresponding to position 97, wherein the first mutation includes cysteine, histidine, lysine, serine, threonine, or methionine; a second mutation at amino acid position 588 or an amino acid position corresponding to position 588; wherein the second mutation includes leucine, isoleucine, valine, alanine, or glycine.

In an aspect is provided a method of incorporating a nucleotide into a nucleic acid sequence including combining in a reaction vessel: (i) a nucleic acid template, (ii) a nucleotide solution, and (iii) a polymerase, wherein the polymerase is a polymerase as described herein. In embodiments, the method includes combining the components in a reaction vessel under conditions for incorporating and/or polymerization. Such conditions are known in the art and described herein.

In another aspect is provided a method of amplifying a nucleic acid sequence including: a. hybridizing a nucleic acid template with a primer to form a primer-template hybridization complex; b. contacting the primer-template hybridization complex with a DNA polymerase and nucleotides, wherein the DNA polymerase is the polymerase as described herein; and c. subjecting the primer-template hybridization complex to conditions which enable the polymerase to incorporate one or more nucleotides into the primer-template hybridization complex to generate amplification products, thereby amplifying a nucleic acid sequence.

BRIEF DESCRIPTION OF THE DRAWINGS

FIG. 1 depicts an alignment of two sequences described herein. SEQ ID NO:3 is aligned to SEQ ID NO:1 and amino acid positions 541-560 are depicted in FIG. 1. The alignment highlights a deletion in SEQ ID NO:3 relative to SEQ ID NO:1, such that any amino acid positions beyond amino acid position 554 are shifted −1 in SEQ ID NO:3 relative to SEQ ID NO:1 (i.e., amino acid E554 in SEQ ID NO:3 corresponds to E555 in SEQ ID NO:1).

DETAILED DESCRIPTION

The aspects and embodiments described herein relate to strand displacing polymerases and uses thereof.

Definitions

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms “a”, “an”, and “the” include the plural reference unless the context clearly indicates otherwise. Reference throughout this specification to, for example, “one embodiment”, “an embodiment”, “another embodiment”, “a particular embodiment”, “a related embodiment”, “a certain embodiment”, “an additional embodiment”, or “a further embodiment” or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

As used herein, the term “about” means a range of values including the specified value, which a person of ordinary skill in the art would consider reasonably similar to the specified value. In embodiments, the term “about” means within a standard deviation using measurements generally acceptable in the art. In embodiments, about means a range extending to +/−10% of the specified value. In embodiments, about means the specified value.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

“Nucleic acid” refers to nucleotides (e.g., deoxyribonucleotides or ribonucleotides) and polymers thereof in either single-, double- or multiple-stranded form, or complements thereof. The terms “polynucleotide,” “oligonucleotide,” “oligo” or the like refer, in the usual and customary sense, to a sequence of nucleotides. The term “nucleotide” refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

The term “duplex” in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like. Different polynucleotides may have different three-dimensional structures, and may perform various functions, known or unknown.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The term “base” and “nucleobase” as used herein refers to a purine or pyrimidine compound, or a derivative thereof, that may be a constituent of nucleic acid (i.e. DNA or RNA, or a derivative thereof). In embodiments, the base is a derivative of a naturally occurring DNA or RNA base (e.g., a base analogue). In embodiments, the base is a base-pairing base. In embodiments, the base pairs to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), guanosine or a derivative thereof (e.g., 7-methylguanosine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is thymine, cytosine, uracil, adenine, guanine, hypoxanthine, xanthine, theobromine, caffeine, uric acid, or isoguanine. In embodiments, the base is

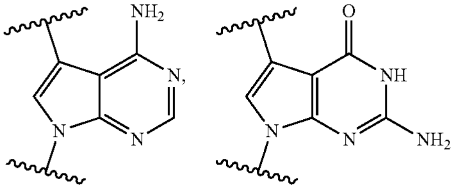
,

-continued

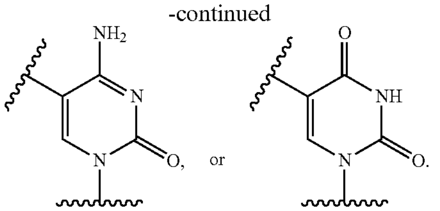

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "isolated", when applied to a nucleic acid or protein, denotes that the nucleic acid or protein is essentially free of other cellular components with which it is associated in the natural state. It can be, for example, in a homogeneous state and may be in either a dry or an aqueous solution. Purity and homogeneity are typically determined using analytical chemistry techniques such as polyacrylamide gel electrophoresis or high performance liquid chromatography. A protein that is the predominant species present in a preparation is substantially purified.

The terms "analog" and "analogue" and "derivative" in reference to a chemical compound, refers to compounds having a structure similar to that of another one, but differing from it in respect of one or more different atoms, functional groups, or substructures that are replaced with one or more other atoms, functional groups, or substructures. In the context of a nucleotide useful in practicing the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: a Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The term "complement," as used herein, refers to a nucleotide (e.g., RNA or DNA) or a sequence of nucleotides capable of base pairing with a complementary nucleotide or sequence of nucleotides. As described herein and commonly known in the art, the complementary (matching) nucleoside of adenosine is thymidine and the complementary (matching) nucleoside of guanosine is cytidine. Thus, a complement may include a sequence of nucleotides that base pair with corresponding complementary nucleotides of a second nucleic acid sequence. The nucleotides of a complement may match, partially or completely, the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence, only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein, the complementarity of sequences may be partial, in which only some of the nucleic acids match according to base pairing, or complete, where all the nucleic acids match according to base pairing. Thus, two sequences that are complementary to each other may have a specified percentage of nucleotides that are complementary (i.e., about 60% identity, preferably 65%, 70%, 75%, 80%, 85%, 90%, 91%, 92%, 93%, 94%, 95%, 96%, 97%, 98%, 99%, or higher complementarity over a specified region).

"DNA" refers to deoxyribonucleic acid, a polymer of deoxyribonucleotides (e.g., dATP, dCTP, dGTP, dTTP, dUTP, etc.) linked by phosphodiester bonds. DNA can be single-stranded (ssDNA) or double-stranded (dsDNA), and can include both single and double-stranded (or "duplex") regions. "RNA" refers to ribonucleic acid, a polymer of ribonucleotides linked by phosphodiester bonds. RNA can be single-stranded (ssRNA) or double-stranded (dsRNA), and can include both single and double-stranded (or "duplex") regions. Single-stranded DNA (or regions thereof) and ssRNA can, if sufficiently complementary, hybridize to form double-stranded DNA/RNA complexes (or regions).

The term "DNA primer" refers to any DNA molecule that may hybridize to a DNA template and be bound by a DNA polymerase and extended in a template-directed process for nucleic acid synthesis. The term "DNA template" refers to any DNA molecule that may be bound by a DNA polymerase and utilized as a template for nucleic acid synthesis.

The term “dATP analogue” refers to an analogue of deoxyadenosine triphosphate (dATP) that is a substrate for a DNA polymerase. The term “dCTP analogue” refers to an analogue of deoxycytidine triphosphate (dCTP) that is a substrate for a DNA polymerase. The term “dGTP analogue” refers to an analogue of deoxyguanosine triphosphate (dGTP) that is a substrate for a DNA polymerase. The term “dNTP analogue” refers to an analogue of deoxynucleoside triphosphate (dNTP) that is a substrate for a DNA polymerase. The term “dTTP analogue” refers to an analogue of deoxythymidine triphosphate (dUTP) that is a substrate for a DNA polymerase. The term “dUTP analogue” refers to an analogue of deoxyuridine triphosphate (dUTP) that is a substrate for a DNA polymerase.

The term “extendible” means, in the context of a nucleotide, primer, or extension product, that the 3'-OH group of the particular molecule is available and accessible to a DNA polymerase for extension or addition of nucleotides derived from dNTPs or dNTP analogues. “Incorporation” means joining of the modified nucleotide to the free 3' hydroxyl group of a second nucleotide via formation of a phosphodiester linkage with the 5' phosphate group of the modified nucleotide. The second nucleotide to which the modified nucleotide is joined will typically occur at the 3' end of a polynucleotide chain. As used herein, the term “incorporating” or “chemically incorporating,” when used in reference to a primer and a nucleotide, refers to the process of joining the nucleotide to the primer or extension product thereof by formation of a phosphodiester bond. As used herein, the term “extension” or “elongation” is used in accordance with their plain and ordinary meanings and refer to synthesis by a polymerase of a new polynucleotide strand (i.e., an “extension strand”) complementary to a template strand by adding free nucleotides (e.g., dNTPs) from a reaction mixture that are complementary to the template in a 5'-to-3' direction, including condensing a 5'-phosphate group of a dNTPs with a 3'-hydroxy group at the end of the nascent (elongating) DNA strand.

Descriptions of nucleotide analogues of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term “amino acid” refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms “non-naturally occurring amino acid” and “unnatural amino acid” refer to amino acid analogs, synthetic amino acids, and amino acid mimetics, which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms “polypeptide,” “peptide” and “protein” are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A “fusion protein” refers to a chimeric protein encoding two or more separate protein sequences that are recombinantly expressed as a single moiety.

“Conservatively modified variants” applies to both amino acid and nucleic acid sequences. With respect to particular nucleic acid sequences, “conservatively modified variants” refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are “silent variations,” which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a “conservatively modified variant” where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following groups each contain amino acids that are conservative substitutions for one another: 1) Non-polar—Alanine (A), Leucine (L), Isoleucine (I), Valine (V), Glycine (G), Methionine (M); 2) Aliphatic—Alanine (A), Leucine (L), Isoleucine (I), Valine (V); 3) Acidic—Aspartic acid (D), Glutamic acid (E); 4) Polar—Asparagine (N), Glutamine (Q); Serine (S), Threonine (T); 5) Basic—Arginine (R), Lysine (K); 7) Aromatic—Phenylalanine (F), Tyrosine (Y), Tryptophan (W), Histidine (H); 8) Other—Cysteine (C) and Proline (P).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithm with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. As used herein, percent (%) amino acid sequence identity is defined as the percentage of amino acids in a candidate sequence that is identical to the amino acids in a reference sequence, after aligning the sequences and introducing gaps, if necessary, to achieve the maximum percent sequence identity. Alignment for purposes of determining percent sequence identity can be achieved in various ways that are within the level of skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 700, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The term "DNA polymerase" and "nucleic acid polymerase" are used in accordance with their plain ordinary meaning and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator γ, 9° N polymerase (exo-), Therminator II, Therminator III, or Therminator IX). In embodiments, the DNA polymerase is a *Pyrococcus* DNA polymerase. For example, a polymerase catalyzes the addition of a next correct nucleotide to the 3'-OH group of the primer via a phosphodiester bond, thereby chemically incorporating the nucleotide into the primer. Optionally, the polymerase used in the provided methods is a processive polymerase. Optionally, the polymerase used in the provided methods is a distributive polymerase.

The term "thermophilic nucleic acid polymerase" as used herein refers to a family of DNA polymerases (e.g., 9° N™) and mutants thereof derived from the DNA polymerase originally isolated from the hyperthermophilic archaea,

*Thermococcus* sp. 9 degrees N-7, found in hydrothermal vents at that latitude (East Pacific Rise) (Southworth M W, et al. *PNAS.* 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase, including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L4085/Y409A/P410V mutations, NEB Therminator IX DNA polymerase), or γ-phosphate labeled nucleotides (e.g., Therminator γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. *PNAS.* 1996; 93(11):5281-5285; Bergen K, et al. *ChemBioChem.* 2013; 14(9):1058-1062; Kumar S, et al. *Scientific Reports.* 2012; 2:684; Fuller C W, et al. 2016; 113(19):5233-5238; Guo J, et al. *PNAS.* 2008; 105(27):9145-9150), which are incorporated herein in their entirety for all purposes.

In the context of this application, the term "motif A region" specifically refers to the three amino acids functionally equivalent, corresponding to, positionally equivalent, or homologous to amino acids 409, 410, and 411 in wild type *P. horikoshii*; these amino acids are functionally equivalent to amino acid positions 408, 409, and 410 in 9° N polymerase. Functionally equivalent, positionally equivalent, or homologous "motif A regions" of polymerases other than *P. horikoshii* can be identified on the basis of amino acid sequence alignment and/or molecular modeling. Sequence alignments may be compiled using any of the standard alignment tools known in the art, such as for example BLAST, DIAMOND (Buchfink et al. Nat Methods 12, 59-60 (2015)), and the like.

The terms "position", "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. Similarly, the term "functionally equivalent to" in relation to an amino acid position refers to an amino acid residue in a protein that corresponds to a particular amino acid in a reference sequence. An amino acid "corresponds" to a given residue when it occupies the same essential structural position within the protein as the given residue. One skilled in the art will immediately recognize the identity and location of residues corresponding to a specific position in a protein (e.g., polymerase) in other proteins with different numbering systems. For example, by performing a simple sequence alignment with a protein (e.g., polymerase) the identity and location of residues corresponding to specific positions of said protein are identified in other protein sequences aligning to said protein. For example, a selected residue in a selected protein corresponds to methionine at position 129 when the selected residue occupies the same essential spatial or other structural relationship as a methionine at position 129. In some embodiments, where a selected protein is aligned for maximum homology with a protein, the position in the aligned selected protein aligning with methionine 129 is said to correspond to methionine 129. Instead of a primary sequence alignment, a three-dimensional structural alignment can also be used, e.g., where the structure of the selected protein is aligned for maximum correspondence with the methionine at position 129, and the overall structures compared. In this case, an amino acid that occupies the same essential position as methionine 129 in the structural model is said to correspond to the methionine 129 residue. For example, references to a *P. horikoshii* polymerase amino acid position recited herein may refer to a numbered position set forth in SEQ ID NO:1, or the corresponding position in a polymerase homolog of SEQ ID NO:1. For example, when identifying an amino acid that corresponds to a position in SEQ ID NO:1, aligning the second enzyme species identifies if any insertions and/or deletions shift the position of the amino acid. An alignment of SEQ ID NO:3 to SEQ ID NO:1, a portion of which is provided in FIG. 1, highlights a deletion in SEQ ID NO:3 relative to SEQ ID NO:1, such that any amino acid positions beyond amino acid position 554 are shifted −1 in SEQ ID NO:3 relative to SEQ ID NO:1 (i.e., amino acid E554 in SEQ ID NO:3 corresponds to E555 in SEQ ID NO:1).

In embodiments, the polymerase may include an amino acid substitution mutation at a particular position corresponding to a position in SEQ ID NO: 1. For example, in embodiments, the polymerase includes an amino acid substitution mutation at position 141, which means the variant polymerase has a different amino acid at position 141 compared to SEQ ID NO: 1. In embodiments, the polymerase includes an amino acid substitution mutation at more than one position compared to SEQ ID NO: 1. For example, in embodiments, the polymerase includes the following substitution mutations: D141A; E143A; L4095; Y410A; P411V, where the number refers to the corresponding position in SEQ ID NO: 1. One having skill in the art would understand the amino acid mutation nomenclature, such that D141A refers to aspartic acid (single letter code is D), at position 141, being replaced with alanine (single letter code A).

The term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide, thereby releasing deoxyribonucleoside 5'-monophosphates one after another. One having skill in the art understands that an enzyme having 3'-5' exonuclease activity does not cleave DNA strands without terminal 3'-OH moieties. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

The terms "measure", "measuring", "measurement" and the like refer not only to quantitative measurement of a particular variable, but also to qualitative and semi-quantitative measurements. Accordingly, "measurement" also includes detection, meaning that merely detecting a change, without quantification, constitutes measurement.

A "polymerase-template complex" refers to a functional complex between a DNA polymerase and a DNA primer-template molecule (e.g., nucleic acid). In embodiments, the polymerase is non-covalently bound to a nucleic acid primer and the template nucleic acid molecule.

The term "solid substrate" means any suitable medium present in the solid phase to which an antibody or an agent can be covalently or non-covalently affixed or immobilized. Preferred solid substrates are glass. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers.

The term "species", when used in the context of describing a particular compound or molecule species, refers to a population of chemically indistinct molecules. When used in the context of taxonomy, "species" is the basic unit of classification and a taxonomic rank. For example, in reference to the microorganism *Pyrococcus horikoshii, horikoshii* is a species of the genus *Pyrococcus.*

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

"Control" or "control experiment" is used in accordance with its plain ordinary meaning and refers to an experiment in which the subjects (e.g., enzymes) or reagents of the experiment are treated as in a parallel experiment except for omission of a procedure, reagent, or variable of the experiment (e.g., a polymerase not having one or more mutations relative to the polymerase being tested). In some instances, the control is used as a standard of comparison in evaluating experimental effects. In some embodiments, a control is the measurement of the activity of a protein in the absence of a mutation as described herein (including embodiments and examples). "Control polymerase" is defined herein as the polymerase against which the activity of the altered polymerase is compared. In one embodiment of the invention the control polymerase may comprise a wild type polymerase or an exo-variant thereof. Unless otherwise stated, by "wild type" it is generally meant that the polymerase comprises its natural amino acid sequence, as it would be found in nature. The invention is not limited to merely a comparison of activity of the polymerases as described herein against the wild type equivalent or exo-variant of the polymerase that is being altered. Many polymerases exist whose amino acid sequence has been modified (e.g., by amino acid substitution mutations) and which can prove to be a suitable control for use in assessing the modified nucleotide incorporation efficiencies of the polymerases as described herein. The control polymerase can, therefore, comprise any known polymerase, including mutant polymerases known in the art. The activity of the chosen "control" polymerase with respect to incorporation of the desired nucleotide analogues may be determined by an incorporation assay.

The term "modulate" is used in accordance with its plain ordinary meaning and refers to the act of changing or varying one or more properties. "Modulation" refers to the process of changing or varying one or more properties.

The term "kit" is used in accordance with its plain ordinary meaning and refers to any delivery system for delivering materials or reagents for carrying out a method of the invention. Such delivery systems include systems that allow for the storage, transport, or delivery of reaction reagents (e.g., nucleotides, enzymes, nucleic acid templates, etc. in the appropriate containers) and/or supporting materials (e.g., buffers, written instructions for performing the reaction, etc.) from one location to another location. For example, kits include one or more enclosures (e.g., boxes) containing the relevant reaction reagents and/or supporting materials. Such contents may be delivered to the intended recipient together or separately. For example, a first container may contain an enzyme, while a second container contains nucleotides. In embodiments, the kit includes vessels containing one or more enzymes, primers, adapters, or other reagents as described herein. Vessels may include any structure capable of supporting or containing a liquid or solid material and may include tubes, vials, jars, containers, tips, etc. In embodiments, a wall of a vessel may permit the transmission of light through the wall. In embodiments, the vessel may be optically clear. The kit may include the enzyme and/or nucleotides in a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Synthetic" DNA polymerases refer to non-naturally occurring DNA polymerases such as those constructed by synthetic methods, mutated parent DNA polymerases such as truncated DNA polymerases and fusion DNA polymerases (e.g., as described in U.S. Pat. No. 7,541,170). Variants of the parent DNA polymerase have been engineered by mutating residues using site-directed or random mutagenesis methods known in the art. In embodiments, the mutations are in any of Motifs I-VI. The variant is expressed in an expression system such as *E. coli* by methods known in the art. The variant is then screened using the assays described herein to determine activity (e.g., strand-displacing activity).

As used herein, the term "template polynucleotide" or "template nucleic acid" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The terms "single strand" and "ssDNA" are used in accordance with its plain and ordinary meaning and refer to a single-stranded polynucleotide. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

In embodiments, a target polynucleotide is a cell-free polynucleotide. In general, the terms "cell-free," "circulating," and "extracellular" as applied to polynucleotides (e.g. "cell-free DNA" (cfDNA) and "cell-free RNA" (cfRNA)) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g. apoptosis or necrosis) or cell shedding, releasing polynucleotides into surrounding body fluids or into circulation. Accordingly, cell-free polynucleotides may be isolated from a non-cellular fraction of blood (e.g. serum or plasma), from other bodily fluids (e.g. urine), or from non-cellular fractions of other types of samples.

As used herein, a "native" nucleotide is used in accordance with its plain and ordinary meaning and refers to a naturally occurring nucleotide that does not include an exogenous label (e.g., a fluorescent dye, or other label) or chemical modification such as those that may characterize a nucleotide analog (e.g., a reversible terminating moiety). Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate). A "canonical" nucleotide is an unmodified nucleotide.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety (alternatively referred to herein as a reversible terminator moiety) and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently $-NH_2$, $-CN$, $-CH_3$, $C_2$-$C_6$ allyl (e.g., $-CH_2-CH=CH_2$), methoxyalkyl (e.g., —$CH_2$—O—$CH_3$), or —$CH_2N_3$. In embodiments, the blocking moiety is attached to the 3' oxygen of the nucleotide and is independently

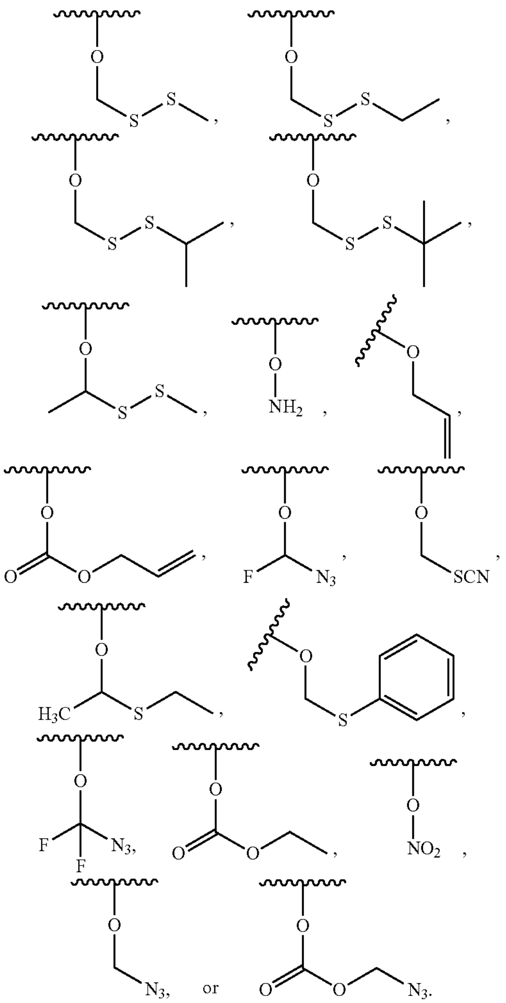

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. Nos. 6,664,079, 10,738,072, and 11,174,281, each which are incorporated herein by reference in their entirety for all purposes.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association.

As used herein, the term "complementary" or "substantially complementary" refers to the hybridization, base pairing, or the formation of a duplex between nucleotides or nucleic acids. For example, complementarity exists between the two strands of a double-stranded DNA molecule or between an oligonucleotide primer and a primer binding site on a single-stranded nucleic acid when a nucleotide (e.g., RNA or DNA) or a sequence of nucleotides is capable of base pairing with a respective cognate nucleotide or cognate sequence of nucleotides. When referring to a double-stranded polynucleotide including a first strand hybridized to a second strand, it is to be understood that each of the terms "first strand" and "second strand" refer to single-stranded polynucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

"Duplex" means at least two oligonucleotides and/or polynucleotides that are fully or partially complementary undergo Watson-Crick type base pairing among all or most of their nucleotides so that a stable complex is formed. Complementary single stranded nucleic acids and/or substantially complementary single stranded nucleic acids can hybridize to each other under hybridization conditions, thereby forming a nucleic acid that is partially or fully double stranded. When referring to a double-stranded polynucleotide including a first strand hybridized to a second strand, it is understood that each of the first strand and the second strand are independently single-stranded polynucleotides. All or a portion of a nucleic acid sequence may be substantially complementary to another nucleic acid sequence, in some embodiments.

As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often comprise nucleic acid sequences that are substantially complementary to each other.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, nucleic acid, a protein, or enzyme (e.g., a DNA polymerase).

As used herein, the terms "solid support" and "substrate" and "solid surface" are used interchangeably and refers to discrete solid or semi-solid surfaces to which a plurality of nucleic acid (e.g., primers) may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. Solid supports may be in the form of discrete particles, which alone does not imply or require any particular shape. The term "particle" means a small body made of a rigid or semi-rigid material. The body can have a shape characterized, for example, as a sphere, oval, microsphere, or other recognized particle shape whether having regular or irregular dimensions. As used herein, the term "discrete particles" refers to physically distinct particles having discernible boundaries. The term "particle" does not indicate any particular shape. The shapes and sizes of a collection of particles may be different or about the same (e.g., within a desired range of dimensions, or having a desired average or minimum dimension). A particle may be substantially spherical (e.g., microspheres) or have a non-spherical or irregular shape, such as cubic, cuboid, pyramidal, cylindrical, conical, oblong, or disc-shaped, and the like. In embodiments, the particle has the shape of a sphere, cylinder, spherocylinder, or ellipsoid. Discrete particles collected in a container and contacting one another will define a bulk volume containing the particles, and will typically leave some internal fraction of that bulk volume unoccupied by the particles, even when packed closely together. In embodiments, cores and/or core-shell particles are approximately spherical. As used herein the term "spherical" refers to structures which appear substantially or generally of spherical shape to the human eye, and does not require a sphere to a mathematical standard. In other words, "spherical" cores or particles are generally spheroidal in the sense of resembling or approximating to a sphere. In embodiments, the diameter of a spherical core or particle is substantially uniform, e.g., about the same at any point, but may contain imperfections, such as deviations of up to 1, 2, 3, 4, 5 or up to 10%. Because cores or particles may deviate from a perfect sphere, the term "diameter" refers to the longest dimension of a given core or particle. Likewise, polymer shells are not necessarily of perfect uniform thickness all around a given core. Thus, the term "thickness" in relation to a polymer structure (e.g., a shell polymer of a core-shell particle) refers to the average thickness of the polymer layer.

A solid support may further comprise a polymer or hydrogel on the surface to which the primers are attached (e.g., the primers are covalently attached to the polymer, wherein the polymer is in direct contact with the solid support). Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008). In certain embodiments a substrate comprises a surface (e.g., a surface of a flow cell, a surface of a tube, a surface of a chip, surface of a particle), for example a metal surface (e.g., steel, gold, silver, aluminum, silicon and copper). In some embodiments a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In some embodiments a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, silica, nylon, Wang resin, Merrifield resin, metal (e.g., iron, a metal alloy, sepharose, agarose, polyacrylamide, dextran, cellulose and the like or combinations thereof. In some embodiments a substrate comprises a magnetic material (e.g., iron, nickel, cobalt, platinum, aluminum, and the like). In certain embodiments a substrate comprises a magnetic bead (e.g., DYNABEADS®, hematite, AMPure XP). Magnets can be used to purify and/or capture nucleic acids bound to certain substrates (e.g., substrates comprising a metal or magnetic material).

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer. Polymers can be hydrophilic, hydrophobic, or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers.

The term "surface" is intended to mean an external part or external layer of a substrate. The surface can be in contact with another material such as a gas, liquid, gel, polymer, organic polymer, second surface of a similar or different material, metal, or coating. The surface, or regions thereof, can be substantially flat. The substrate and/or the surface can have surface features such as wells, pits, channels, ridges, raised regions, pegs, posts or the like.

As used herein, the terms "cluster" and "colony" are used interchangeably to refer to a discrete site on a solid support that includes a plurality of immobilized polynucleotides and a plurality of immobilized complementary polynucleotides. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as a polymerase described herein, including embodiments. RCA may be performed by using any of the DNA polymerases that are known in the art (e.g., a Phi29 DNA polymerase, a Bst DNA polymerase, or SD polymerase).

As used herein, the term "hybridize" or "specifically hybridize" refers to a process where two complementary nucleic acid strands anneal to each other under appropriately stringent conditions. Hybridizations are typically and preferably conducted with oligonucleotides. The terms "annealing" and "hybridization" are used interchangeably to mean the formation of a stable duplex. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution. Those skilled in the art understand how to estimate and adjust the stringency of hybridization conditions such that sequences having at least a desired level of complementarity will stably hybridize, while those having lower complementarity will not. As used herein, the term "stringent condition" refers to condition(s) under which a polynucleotide probe or primer will hybridize preferentially to its target sequence, and to a lesser extent to, or not at all to, other sequences. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands (e.g., two single-stranded polynucleotides) that are hybridized to each other can form a duplex which comprises a double-stranded portion of nucleic acid.

II. Compositions & Kits

In an aspect is provided a polymerase including an amino acid sequence that is at least 80% identical to a continuous 500 amino acid sequence within SEQ ID NO: 1; including at least one mutation at amino acid position 7 or an amino acid position corresponding to position 7, wherein the mutation at amino acid position 7 includes histidine, lysine, or arginine; amino acid position 97 or an amino acid position corresponding to position 97, wherein the mutation at amino acid position 97 includes cysteine, histidine, lysine, serine, threonine, or methionine; amino acid position 579 or an amino acid position corresponding to position 579, wherein the mutation at amino acid position 579 includes leucine, isoleucine, valine, alanine, or glycine; amino acid position 588 or an amino acid position corresponding to position 588, wherein the mutation at amino acid position 588 includes leucine, isoleucine, valine, alanine, or glycine; or amino acid position 742 or an amino acid position corresponding to position 742, wherein the mutation at amino acid position 742 includes leucine, isoleucine, alanine, or glycine.

In another aspect is provided a polymerase including an amino acid sequence that is at least 80% identical to a continuous 500 amino acid sequence within SEQ ID NO: 1; including a first mutation at amino acid position 97 or an amino acid position corresponding to position 97, wherein the first mutation includes cysteine, histidine, lysine, serine, threonine, or methionine; a second mutation at amino acid position 588 or an amino acid position corresponding to position 588; wherein the second mutation includes leucine, isoleucine, valine, alanine, or glycine.

In embodiments, the first mutation is cysteine, histidine, or serine. In embodiments, the first mutation is cysteine. In embodiments, the first mutation is histidine. In embodiments, the first mutation is serine.

In embodiments, the second mutation is leucine, isoleucine, valine, or alanine. In embodiments, the second mutation is leucine. In embodiments, the second mutation is isoleucine. In embodiments, the second mutation is alanine. In embodiments, the second mutation is valine.

In embodiments, the polymerase further includes a mutation at amino acid position 742 or an amino acid position corresponding to position 742, wherein the mutation is leucine, isoleucine, alanine, or glycine. In embodiments, the polymerase further includes a mutation at amino acid position 742 or an amino acid position corresponding to position 742, wherein the mutation is leucine. In embodiments, the polymerase further includes a mutation at amino acid position 742 or an amino acid position corresponding to position 742, wherein the mutation is isoleucine. In embodiments, the polymerase further includes a mutation at amino acid position 742 or an amino acid position corresponding to position 742, wherein the mutation is alanine, or glycine. In embodiments, the polymerase further includes a mutation at amino acid position 742 or an amino acid position corresponding to position 742, wherein the mutation is alanine. In embodiments, the polymerase further includes a mutation at amino acid position 742 or an amino acid position corresponding to position 742, wherein the mutation is glycine.

In an aspect is provided a polymerase including an amino acid sequence that is at least 80% identical to a continuous 500 amino acid sequence within SEQ ID NO: 1; including a first mutation at amino acid position 588 or an amino acid position corresponding to position 588; wherein the first mutation is leucine, isoleucine, valine, alanine, or glycine; and a second mutation at amino acid position 7 or an amino acid position corresponding to position 7, wherein the second mutation is histidine, lysine, or arginine.

In an aspect is provided a polymerase including an amino acid sequence that is at least 80% identical to a continuous 500 amino acid sequence within SEQ ID NO: 1; including a first mutation at amino acid position 588 or an amino acid position corresponding to position 588; wherein the first mutation is leucine, isoleucine, valine, alanine, or glycine; and a second mutation at amino acid position 97 or an amino acid position corresponding to position 97, wherein the second mutation is cysteine, histidine, lysine, serine, threonine, or methionine.

In an aspect is provided a polymerase including an amino acid sequence that is at least 80% identical to a continuous 500 amino acid sequence within SEQ ID NO: 1; including a first mutation at amino acid position 588 or an amino acid position corresponding to position 588; wherein the first mutation is leucine, isoleucine, valine, alanine, or glycine; and a second mutation at amino acid position 742 or an amino acid position corresponding to position 742, wherein the second mutation is leucine, isoleucine, alanine, or glycine.

In embodiments, the polymerase further includes a mutation at amino acid position 726 or an amino acid position corresponding to amino acid position 726, wherein the mutation is aspartic acid, glutamic acid, asparagine, or glutamine. In embodiments, the polymerase further includes a mutation at amino acid position 726 or an amino acid position corresponding to amino acid position 726, wherein the mutation is aspartic acid. In embodiments, the polymerase further includes a mutation at amino acid position 726 or an amino acid position corresponding to amino acid position 726, wherein the mutation is glutamic acid. In embodiments, the polymerase further includes a mutation at amino acid position 726 or an amino acid position corresponding to amino acid position 726, wherein the mutation is asparagine. In embodiments, the polymerase further includes a mutation at amino acid position 726 or an amino acid position corresponding to amino acid position 726, wherein the mutation is glutamine.

In embodiments, the polymerase includes a mutation at amino acid position 769 or an amino acid position corresponding to position 769, wherein the mutation is leucine, isoleucine, arginine, valine, alanine, or glycine. In embodiments, the polymerase includes a mutation at amino acid position 769 or an amino acid position corresponding to position 769, wherein the mutation is leucine. In embodiments, the polymerase includes a mutation at amino acid position 769 or an amino acid position corresponding to position 769, wherein the mutation is isoleucine. In embodiments, the polymerase includes a mutation at amino acid position 769 or an amino acid position corresponding to position 769, wherein the mutation is valine. In embodiments, the polymerase includes a mutation at amino acid position 769 or an amino acid position corresponding to position 769, wherein the mutation is alanine. In embodiments, the polymerase includes a mutation at amino acid position 769 or an amino acid position corresponding to position 769, wherein the mutation is glycine. In embodiments, the polymerase includes a mutation at amino acid position 769 or an amino acid position corresponding to position 769, wherein the mutation is arginine.

In embodiments, the polymerase includes a mutation at amino acid position 7 or an amino acid position corresponding to position 7, wherein the mutation is histidine, lysine, or arginine. In embodiments, the polymerase includes a mutation at amino acid position 7 or an amino acid position corresponding to position 7, wherein the mutation is histidine. In embodiments, the polymerase includes a mutation at amino acid position 7 or an amino acid position corresponding to position 7, wherein the mutation is lysine. In embodiments, the polymerase includes a mutation at amino acid position 7 or an amino acid position corresponding to position 7, wherein the mutation is arginine.

In embodiments, the polymerase includes a mutation at amino acid position 13 or an amino acid position corresponding to position 13, wherein the mutation is arginine, isoleucine, methionine, or histidine. In embodiments, the polymerase includes a mutation at amino acid position 13 or an amino acid position corresponding to position 13, wherein the mutation is arginine or histidine. In embodiments, the polymerase includes a mutation at amino acid position 13 or an amino acid position corresponding to position 13, wherein the mutation is arginine. In embodiments, the polymerase includes a mutation at amino acid position 13 or an amino acid position corresponding to position 13, wherein the mutation is histidine. In embodiments, the polymerase includes a mutation at amino acid position 13 or an amino acid position corresponding to position 13, wherein the mutation is methionine. In embodiments, the polymerase includes a mutation at amino acid position 13 or an amino acid position corresponding to position 13, wherein the mutation is isoleucine. In embodiments, the polymerase includes a mutation at amino acid position 13 or an amino acid position corresponding to position 13, wherein the mutation is arginine, leucine, isoleucine, or histidine.

In embodiments, the polymerase includes a mutation at amino acid position 13 or an amino acid position corresponding to position 13, wherein the mutation is arginine, leucine, isoleucine, or histidine; and a mutation at amino acid position 579 or an amino acid position corresponding to position 579, wherein the mutation is alanine or glycine.

In embodiments, the polymerase includes a mutation at amino acid position 40 or an amino acid position corresponding to position 40, wherein the mutation is valine, leucine, or threonine. In embodiments, the mutation at amino acid position 40 is valine. In embodiments, the mutation at amino acid position 40 is leucine. In embodiments, the mutation at amino acid position 40 is threonine.

In embodiments, the polymerase includes a mutation at amino acid position 75 or an amino acid position corresponding to position 75, wherein the mutation at amino acid position 75 is cysteine, histidine, lysine, serine, threonine, or methionine. In embodiments, the mutation at amino acid position 75 is cysteine. In embodiments, the mutation at amino acid position 75 is histidine. In embodiments, the mutation at amino acid position 75 is lysine. In embodiments, the mutation at amino acid position 75 is serine. In embodiments, the mutation at amino acid position 75 is threonine. In embodiments, the mutation at amino acid position 75 is methionine.

In embodiments, the polymerase includes a glutamine, valine, arginine, or alanine at amino acid position 93 or an amino acid position corresponding to position 93. In embodiments, the mutation at amino acid position 93 is glutamine, valine, arginine, or alanine. In embodiments, the mutation at amino acid position 93 is glutamine. In embodiments, the mutation at amino acid position 93 is valine. In embodiments, the mutation at amino acid position 93 is arginine. In embodiments, the mutation at amino acid position 93 is alanine. In embodiments, the polymerase includes a glutamine, valine, arginine, or alanine at amino acid position 93 or the amino acid position corresponding to position 93. In embodiments, the polymerase includes a glutamine, valine, arginine, or alanine at amino acid position 93. It is known that the presence of uracil in DNA results in a dramatic increase in the binding affinity of archaeal family B DNA polymerases, stalling further polymerase activity (Lasken R S et al. J. Biol. Chem. 1996, 271 (30):17692-6 and Fogg M J et al. Nature Structural Biology. 2002, 9: 922-7). A specific point mutation in the uracil-binding pocket of these polymerases disrupts uracil binding and allows extension in the presence of uracil without compromising polymerase activity (Norholm MH BMC Biotechnology. 2010, 10:21). Provided herein are novel DNA polymerase variants (e.g., V93Q, V93R, V93A) that disrupt the uracil binding pocket. In embodiments, the polymerase includes a V93Q, V93R, or V93A mutation. In embodiments, the polymerase includes a V93Q mutation. In embodiments, the polymerase includes a V93I, V93L, V93N, V93D, or V93E mutation. In embodiments, the polymerase includes an amino acid substitution at position 93. In embodiments, the amino acid substitution at position 93 is a glutamine substitution. In embodiments, the amino acid substitution at position 93 is an arginine substitution. In embodiments, the amino acid substitution at position 93 is an alanine substitution. In embodiments, the amino acid substitution at position 93 is a leucine substitution. In embodiments, the amino acid substitution at position 93 is an isoleucine substitution.

In embodiments, the polymerase includes a mutation at amino acid position 97 or an amino acid position corresponding to position 97, wherein the mutation at amino acid position 97 is cysteine, histidine, leucine, lysine, serine, threonine, or methionine. In embodiments, the mutation at amino acid position 97 is cysteine. In embodiments, the mutation at amino acid position 97 is histidine. In embodiments, the mutation at amino acid position 97 is lysine. In embodiments, the mutation at amino acid position 97 is serine. In embodiments, the mutation at amino acid position 97 is threonine. In embodiments, the mutation at amino acid position 97 is methionine. In embodiments, the mutation at amino acid position 97 is leucine.

In embodiments, the polymerase includes a mutation at amino acid position 160 or an amino acid position corresponding to position 160, wherein the mutation is leucine, valine, alanine, or glycine. In embodiments, the mutation at amino acid position 160 is leucine. In embodiments, the mutation at amino acid position 160 is valine. In embodiments, the mutation at amino acid position 160 is alanine. In embodiments, the mutation at amino acid position 160 is glycine.

In embodiments, the polymerase includes a mutation at amino acid position 168 or an amino acid position corresponding to position 168, wherein the mutation is threonine, serine, cysteine, or glycine. In embodiments, the mutation at amino acid position 168 is threonine. In embodiments, the mutation at amino acid position 168 is serine. In embodiments, the mutation at amino acid position 168 is cysteine. In embodiments, the mutation at amino acid position 168 is glycine.

In embodiments, the polymerase includes a mutation at amino acid position 214 or an amino acid position corresponding to position 214, wherein the mutation is leucine, alanine, isoleucine, serine, threonine, or glycine. In embodiments, the mutation at amino acid position 214 is leucine. In embodiments, the mutation at amino acid position 214 is alanine. In embodiments, the mutation at amino acid position 214 is isoleucine. In embodiments, the mutation at amino acid position 214 is glycine. In embodiments, the mutation at amino acid position 214 is threonine. In embodiments, the mutation at amino acid position 214 is serine.

In embodiments, the polymerase includes a mutation at amino acid position 241 or an amino acid position corresponding to position 241, wherein the mutation is leucine, isoleucine, alanine, valine, or glycine. In embodiments, the polymerase includes a mutation at amino acid position 241 or an amino acid position corresponding to position 241, wherein the mutation is leucine. In embodiments, the polymerase includes a mutation at amino acid position 241 or an amino acid position corresponding to position 241, wherein the mutation is isoleucine. In embodiments, the polymerase includes a mutation at amino acid position 241 or an amino acid position corresponding to position 241, wherein the mutation is alanine. In embodiments, the polymerase includes a mutation at amino acid position 241 or an amino acid position corresponding to position 241, wherein the mutation is valine. In embodiments, the polymerase includes a mutation at amino acid position 241 or an amino acid position corresponding to position 241, wherein the mutation is glycine.

In embodiments, the polymerase includes a mutation at amino acid position 281 or an amino acid position corresponding to position 281, wherein the mutation is threonine, serine, cysteine, or glycine. In embodiments, the mutation at amino acid position 281 is threonine. In embodiments, the mutation at amino acid position 281 is serine. In embodiments, the mutation at amino acid position 281 is cysteine. In embodiments, the mutation at amino acid position 281 is glycine.

In embodiments, the polymerase includes a mutation at amino acid position 292 or an amino acid position corresponding to position 292, wherein the mutation is glutamic acid, valine, leucine, or glycine. In embodiments, the mutation at amino acid position 292 is glutamic acid. In embodiments, the mutation at amino acid position 292 is valine. In embodiments, the mutation at amino acid position 292 is leucine. In embodiments, the mutation at amino acid position 292 is glycine.

In embodiments, the polymerase includes a mutation at amino acid position 316 or an amino acid position corresponding to position 316, wherein the mutation is proline or glycine. In embodiments, the mutation at amino acid position 316 is proline. In embodiments, the mutation at amino acid position 316 is glycine.

In embodiments, the polymerase includes a mutation at amino acid position 350 or an amino acid position corresponding to position 350, wherein the mutation is threonine or serine. In embodiments, the mutation at amino acid position 350 is serine. In embodiments, the mutation at amino acid position 350 is threonine.

In embodiments, the polymerase includes a mutation at amino acid position 465 or an amino acid position corresponding to position 465, wherein the mutation is asparagine, aspartic acid, glutamic acid, threonine, or glutamine. In embodiments, the polymerase includes a mutation at amino acid position 465 or an amino acid position corresponding to position 465, wherein the mutation is asparagine. In embodiments, the polymerase includes a mutation at amino acid position 465 or an amino acid position corresponding to position 465, wherein the mutation is aspartic acid. In embodiments, the polymerase includes a mutation at amino acid position 465 or an amino acid position corresponding to position 465, wherein the mutation is glutamic acid. In embodiments, the polymerase includes a mutation at amino acid position 465 or an amino acid position corresponding to position 465, wherein the mutation is glutamine. In embodiments, the polymerase includes a mutation at amino acid position 465 or an amino acid position corresponding to position 465, wherein the mutation is threonine.

In embodiments, the polymerase includes a mutation at amino acid position 469 or an amino acid position corresponding to position 469, wherein the mutation is threonine, serine, cysteine, or methionine. In embodiments, the polymerase includes a mutation at amino acid position 469 or an amino acid position corresponding to position 469, wherein the mutation is threonine. In embodiments, the polymerase includes a mutation at amino acid position 469 or an amino acid position corresponding to position 469, wherein the mutation is serine. In embodiments, the polymerase includes a mutation at amino acid position 469 or an amino acid position corresponding to position 469, wherein the mutation is cysteine. In embodiments, the polymerase includes a mutation at amino acid position 469 or an amino acid position corresponding to position 469, wherein the mutation is methionine.

In embodiments, the polymerase includes a mutation at amino acid position 469 or an amino acid position corresponding to position 469, wherein the mutation is asparagine, aspartic acid, glutamic acid, or glutamine. In embodiments, the polymerase includes a mutation at amino acid position 469 or an amino acid position corresponding to position 469, wherein the mutation is asparagine. In embodiments, the polymerase includes a mutation at amino acid position 469 or an amino acid position corresponding to position 469, wherein the mutation is aspartic acid. In embodiments, the polymerase includes a mutation at amino acid position 469 or an amino acid position corresponding to position 469, wherein the mutation is glutamic acid. In embodiments, the polymerase includes a mutation at amino acid position 469 or an amino acid position corresponding to position 469, wherein the mutation is glutamine.

In embodiments, the polymerase includes a mutation at amino acid position 472 or an amino acid position corresponding to position 472, wherein the mutation is asparagine, aspartic acid, glutamic acid, or glutamine. In embodiments, the polymerase includes a mutation at amino acid position 472 or an amino acid position corresponding to position 472, wherein the mutation is asparagine. In embodiments, the polymerase includes a mutation at amino acid position 472 or an amino acid position corresponding to position 472, wherein the mutation is aspartic acid. In embodiments, the polymerase includes a mutation at amino acid position 472 or an amino acid position corresponding to position 472, wherein the mutation is glutamic acid. In embodiments, the polymerase includes a mutation at amino acid position 472 or an amino acid position corresponding to position 472, wherein the mutation is glutamine. In embodiments, the polymerase includes a mutation at amino acid position 472 or an amino acid position corresponding to position 472, wherein the mutation is asparagine or glutamic acid.

In embodiments, the polymerase includes a mutation at amino acid position 477 or an amino acid position corresponding to position 477, wherein the mutation is isoleucine, leucine, tryptophan, phenylalanine, alanine, or glycine. In embodiments, the mutation at amino acid position 477 is isoleucine. In embodiments, the mutation at amino acid position 477 is leucine. In embodiments, the mutation at amino acid position 477 is alanine. In embodiments, the mutation at amino acid position 477 is glycine. In embodiments, the mutation at amino acid position 477 is tryptophan. In embodiments, the mutation at amino acid position 477 is phenylalanine.

In embodiments, the polymerase includes a mutation at amino acid position 491 or an amino acid position corresponding to position 491, wherein the mutation is glycine, valine, leucine, or isoleucine. In embodiments, the polymerase includes a mutation at amino acid position 491 or an amino acid position corresponding to position 491, wherein the mutation is glycine. In embodiments, the polymerase includes a mutation at amino acid position 491 or an amino acid position corresponding to position 491, wherein the mutation is valine. In embodiments, the polymerase includes a mutation at amino acid position 491 or an amino acid position corresponding to position 491, wherein the mutation is leucine. In embodiments, the polymerase includes a mutation at amino acid position 491 or an amino acid position corresponding to position 491, wherein the mutation is isoleucine.

In embodiments, the polymerase includes a mutation at amino acid position 520 or an amino acid position corresponding to position 520, wherein the mutation is histidine, lysine, or arginine. In embodiments, the polymerase includes a mutation at amino acid position 520 or an amino acid position corresponding to position 520, wherein the mutation is histidine. In embodiments, the polymerase includes a mutation at amino acid position 520 or an amino acid position corresponding to position 520, wherein the mutation is lysine. In embodiments, the polymerase includes a mutation at amino acid position 520 or an amino acid position corresponding to position 520, wherein the mutation is arginine.

In embodiments, the polymerase includes a mutation at amino acid position 526 or an amino acid position corresponding to position 526, wherein the mutation is histidine, lysine, or glutamine. In embodiments, the mutation at amino acid position 526 is histidine. In embodiments, the mutation at amino acid position 526 is lysine. In embodiments, the mutation at amino acid position 526 is glutamine.

In embodiments, the polymerase includes a mutation at amino acid position 579 or an amino acid position corresponding to position 579, wherein the mutation is alanine or glycine. In embodiments, the mutation at amino acid position 579 is alanine. In embodiments, the mutation at amino acid position 579 is glycine.

In embodiments, the polymerase includes a mutation at amino acid position 563 or an amino acid position corresponding to amino acid position 563, wherein the mutation is aspartic acid, glycine, asparagine, or glutamine. In embodiments, the mutation at amino acid position 563 is aspartic acid. In embodiments, the mutation at amino acid position 563 is glycine. In embodiments, the mutation at amino acid position 563 is asparagine. In embodiments, the mutation at amino acid position 563 is glutamine.

In embodiments, the polymerase includes a mutation at amino acid position 577 or an amino acid position corresponding to amino acid position 577, wherein the mutation is aspartic acid, lysine, glycine, asparagine, or glutamine. In embodiments, the mutation at amino acid position 577 is aspartic acid. In embodiments, the mutation at amino acid position 577 is glycine. In embodiments, the mutation at amino acid position 577 is asparagine. In embodiments, the mutation at amino acid position 577 is glutamine. In embodiments, the mutation at amino acid position 577 is lysine.

In embodiments, the polymerase includes a mutation at amino acid position 579 or an amino acid position corresponding to amino acid position 579, wherein the mutation is aspartic acid, lysine, glycine, asparagine, or glutamine. In embodiments, the mutation at amino acid position 577 is aspartic acid. In embodiments, the mutation at amino acid position 577 is lysine. In embodiments, the mutation at amino acid position 577 is glycine. In embodiments, the mutation at amino acid position 577 is asparagine. In embodiments, the mutation at amino acid position 577 is glutamine.

In embodiments, the polymerase includes a mutation at amino acid position 588 or an amino acid position corresponding to position 588; wherein the second mutation is leucine, isoleucine, valine, alanine, or glycine. In embodiments, the mutation at amino acid position 588 or an amino acid position corresponding to position 588 is leucine. In embodiments, the mutation at amino acid position 588 or an amino acid position corresponding to position 588 is isoleucine. In embodiments, the mutation at amino acid position 588 or an amino acid position corresponding to position 588 is valine. In embodiments, the mutation at amino acid position 588 or an amino acid position corresponding to position 588 is alanine. In embodiments, the mutation at amino acid position 588 or an amino acid position corresponding to position 588 is glycine. In embodiments, the mutation at amino acid position 588 or an amino acid position corresponding to position 588 is leucine, isoleucine, valine, or alanine. In embodiments, the mutation at amino acid position 588 or an amino acid position corresponding to position 588 is leucine or valine.

In embodiments, the polymerase includes a mutation at amino acid position 601 or an amino acid position corresponding to amino acid position 601, wherein the mutation is aspartic acid, lysine, glycine, asparagine, or glutamine. In embodiments, the mutation at amino acid position 601 is aspartic acid. In embodiments, the mutation at amino acid position 601 is lysine. In embodiments, the mutation at amino acid position 601 is glycine. In embodiments, the mutation at amino acid position 601 is asparagine. In embodiments, the mutation at amino acid position 601 is glutamine.

In embodiments, the polymerase includes a mutation at amino acid position 635 or an amino acid position corresponding to amino acid position 635, wherein the mutation is aspartic acid, lysine, glutamic acid, asparagine, or glutamine. In embodiments, the mutation at amino acid position 635 is aspartic acid. In embodiments, the mutation at amino acid position 635 is glutamic acid. In embodiments, the mutation at amino acid position 635 is asparagine. In embodiments, the mutation at amino acid position 635 is glutamine. In embodiments, the mutation at amino acid position 635 is lysine.

In embodiments, the polymerase includes a mutation at amino acid position 637 or an amino acid position corresponding to amino acid position 637, wherein the mutation is aspartic acid, lysine, glutamic acid, asparagine, or glutamine. In embodiments, the mutation at amino acid position 637 is aspartic acid. In embodiments, the mutation at amino acid position 637 is glutamic acid. In embodiments, the mutation at amino acid position 637 is asparagine. In embodiments, the mutation at amino acid position 637 is glutamine. In embodiments, the mutation at amino acid position 637 is lysine.

In embodiments, the polymerase includes a mutation at amino acid position 655 or an amino acid position corresponding to amino acid position 655, wherein the mutation is aspartic acid, lysine, glycine, asparagine, or glutamine. In embodiments, the mutation at amino acid position 655 is aspartic acid. In embodiments, the mutation at amino acid position 655 is lysine. In embodiments, the mutation at amino acid position 655 is glycine. In embodiments, the mutation at amino acid position 655 is asparagine. In embodiments, the mutation at amino acid position 655 is glutamine.

In embodiments, the polymerase includes a mutation at amino acid position 706 or an amino acid position corresponding to position 706, wherein the mutation at amino acid position 706 is cysteine, histidine, leucine, lysine, serine, threonine, or methionine. In embodiments, the mutation at amino acid position 706 is cysteine. In embodiments, the mutation at amino acid position 706 is histidine. In embodiments, the mutation at amino acid position 706 is lysine. In embodiments, the mutation at amino acid position 706 is serine. In embodiments, the mutation at amino acid position 706 is threonine. In embodiments, the mutation at amino acid position 706 is methionine. In embodiments, the mutation at amino acid position 706 is leucine.

In embodiments, the polymerase includes a mutation at amino acid position 726 or an amino acid position corresponding to amino acid position 726, wherein the mutation is aspartic acid, glutamic acid, asparagine, or glutamine. In embodiments, the mutation at amino acid position 726 is aspartic acid. In embodiments, the mutation at amino acid position 726 is glutamic acid. In embodiments, the mutation at amino acid position 726 is asparagine. In embodiments, the mutation at amino acid position 726 is glutamine.

In embodiments, the polymerase includes a mutation at amino acid position 742 or an amino acid position corresponding to position 742, wherein the mutation is leucine, isoleucine, alanine, or glycine. In embodiments, the mutation at amino acid position 742 is leucine. In embodiments, the mutation at amino acid position 742 is isoleucine. In embodiments, the mutation at amino acid position 742 is alanine. In embodiments, the mutation at amino acid position 742 is glycine.

In embodiments, the polymerase includes a mutation at amino acid position 762 or an amino acid position corresponding to position 762, wherein the mutation is asparagine, glutamine, threonine, or serine. In embodiments, the mutation at amino acid position 762 is asparagine. In embodiments, the mutation at amino acid position 762 is glutamine. In embodiments, the mutation at amino acid position 762 is threonine. In embodiments, the mutation at amino acid position 762 is serine.

In embodiments, the polymerase includes an alanine at amino acid position 141 or an amino acid position corresponding to position 141; and an alanine at amino acid position 143 or an amino acid position corresponding to position 143. In embodiments, the polymerase includes an alanine at amino acid position 141 or the amino acid position corresponding to position 141; and an alanine at amino acid position 143 or the amino acid position corresponding to position 143. In embodiments, the polymerase includes an alanine at amino acid position 141; and an alanine at amino acid position 143.

In embodiments, the polymerase includes an amino acid substitution at position 141. In embodiments, the amino acid substitution at position 141 is an alanine substitution. In embodiments, the amino acid substitution at position 141 is a glycine substitution.

In embodiments, the polymerase includes an amino acid substitution at position 143. In embodiments, the amino acid substitution at position 143 is an alanine substitution. In embodiments, the amino acid substitution at position 143 is a glycine, alanine, threonine, or serine substitution.

In embodiments, the polymerase does not include a mutation at amino acid positions 409 and/or 410.

In embodiments, the polymerase includes, relative to SEQ ID NO:1, R97H, F588L, G635D, and V742A. In embodiments, the polymerase includes, relative to SEQ ID NO:1, K13R, R97C, E579G, and F588L. In embodiments, the polymerase includes, relative to SEQ ID NO:1. In embodiments, the polymerase includes, relative to SEQ ID NO:1, R97C, E563G, E579G, F588L, and V742A. In embodiments, the polymerase includes, relative to SEQ ID NO:1, R97H, F588L, and G635D. In embodiments, the polymerase includes, relative to SEQ ID NO:1, R97C, F588L, and V742A. In embodiments, the polymerase includes, relative to SEQ ID NO:1, Y7H, K13I, R97L, E579G, F588L, and V742A. In embodiments, the polymerase includes, relative to SEQ ID NO:1, Y7H, K13R, R97H, and V742A. In embodiments, the polymerase includes, relative to SEQ ID NO:1, Y7H, K13R, R97C, D141A, E579G, F588L, and V742A. In embodiments, the polymerase includes, relative to SEQ ID NO:1, R97C, E579G, F588L, and V742A. In embodiments, the polymerase includes, relative to SEQ ID NO:1, Y7H, R97C, E579G, and F588L. In embodiments, the polymerase includes, relative to SEQ ID NO:1, Y7H, R97C, and V742A. In embodiments, the polymerase includes, relative to SEQ ID NO:1, Y7H, K13R, E563G, F588L, and V742A. In embodiments, the polymerase includes, relative to SEQ ID NO:1, E29D, Y30F, R97H, I160V, K229E, A511V, I548V, F588L, G635D, and V742A. In embodiments, the polymerase includes, relative to SEQ ID NO:1, K13R, R32H, F75L, R97C, K201I, Y209H, I256V, Y291H, E383D, G400D, R526C, E579G, F588L, E638G, and A730V. In embodiments, the polymerase includes, relative to SEQ ID NO:1, F75L, R97C, I142T, V278I, A281T, A292E, M329L, P372S, H440N, E563G, E579G, F588L, D729Y, and V742A. In embodiments, the polymerase includes, relative to SEQ ID NO:1, I65V, R97H, F283S, V308M, K465E, F588L, T591A, I604M, G635D, and K727T. In embodiments, the polymerase includes, relative to SEQ ID NO:1, E25K, R97C, A168T, R255H, F326Y, K478R, R526H, E556K, K558N, P573S, E581N, F588L, E600K, E601K, R686H, R724H, V742A, K752E, and K762N. In embodiments, the polymerase includes, relative to SEQ ID NO:1, Y7H, K13I, F75L, R97L, I160V, V170I, A316P, K469E, A491V, E579G, F588L, V637D, H726D, and V742A. In embodiments, the polymerase includes, relative to SEQ ID NO:1, Y7H, K13R, A40V, R97H, F116L, A117S, K154E, A281T, I415V, K477I, K552N, N569S, E577K, A585G, F588I, E655D, and V742A. In embodiments, the polymerase includes, relative to SEQ ID NO:1, Y7H, K13R, I38F, A40V, R97C, D141A, P286L, G350S, R467C, and K469T, E579G, F588L, F721Y, H726D, V742A, L756C, R757A, W758G, Q759R, T761P, K762N, Q763R, V764L, and G765V. In embodiments, the polymerase includes, relative to SEQ ID NO:1, V63A, F75L, R97C, D98G, R188H, F214I, G245S, D246E, T319I, G350S, E579G, F588L, R690H, H726D, V742A, and K760N. In embodiments, the polymerase includes, relative to SEQ ID NO:1, Y7H, I18V, R97C, A168S, F214S, G284S, P286Q, A292V, G304D, K391I, E431D, K477I, Y567H, E579G, F588L, and H726D. In embodiments, the polymerase includes, relative to SEQ ID NO:1, Y7H, IBV, N23D, V66A, F75L, R97C, P217Q, A298S, A316P, K465E, R526H, E577K, E601D, T606I, E655D, R706C, V742A, and W769S. In embodiments, the polymerase includes, relative to SEQ ID NO:1, Y7H, K13R, L76P, K192E, K289T, R364C, L397M, Q484H, E563G, F588L, V637D, R706H, V742A, and L766P.

In embodiments, the polymerase includes an amino acid sequence that is at least 85% identical to a continuous 500 amino acid sequence within SEQ ID NO: 1. In embodiments, the polymerase includes an amino acid sequence that is at least 90% identical to a continuous 500 amino acid sequence within SEQ ID NO: 1. In embodiments, the polymerase includes an amino acid sequence that is at least 95% identical to a continuous 500 amino acid sequence within SEQ ID NO: 1. In embodiments, the polymerase includes an amino acid sequence that is at least 98% identical to a continuous 500 amino acid sequence within SEQ ID NO: 1. In embodiments, the polymerase includes an amino acid sequence that is at least 99% identical to a continuous 500 amino acid sequence within SEQ ID NO: 1. In embodiments, the polymerase includes an amino acid sequence that is 90% identical to a continuous 500 amino acid sequence within SEQ ID NO: 1. In embodiments, the polymerase includes an amino acid sequence that is 95% identical to a continuous 500 amino acid sequence within SEQ ID NO: 1. In embodiments, the polymerase includes an amino acid sequence that is 90% identical to SEQ ID NO: 1. In embodiments, the polymerase includes an amino acid sequence that is 95% identical to SEQ ID NO: 1.

In embodiments, the polymerase (e.g., a polymerase as described herein) is truncated at the C-terminus. In embodiments, the polymerase (e.g., a polymerase as described herein) is truncated at the C-terminus and retains the ability to incorporate a modified nucleotide. In embodiments, the polymerase (e.g., a polymerase as described herein) is truncated at the C-terminus, wherein the polymerase is truncated to remove at least 20 amino acids from the C-terminus. In embodiments, the polymerase (e.g., a polymerase as described herein) is truncated at the C-terminus, wherein the polymerase is truncated to remove at least 10 amino acids from the C-terminus. In embodiments, the polymerase (e.g., a polymerase as described herein) is truncated at the C-terminus, wherein the polymerase is truncated to remove at least 5 amino acids from the C-terminus. In embodiments, the polymerase (e.g., a polymerase as described herein) is truncated at the C-terminus, wherein the truncation removes 5 to 16 amino acids from the C-terminus. In embodiments, the polymerase (e.g., a polymerase as described herein) is truncated at the C-terminus, wherein the truncation removes 5 amino acids from the C-terminus. In embodiments, the polymerase (e.g., a polymerase as described herein) is truncated at the C-terminus, wherein the truncation removes 10 amino acids from the C-terminus. In embodiments, the polymerase (e.g., a polymerase as described herein) is truncated at the C-terminus, wherein the truncation removes 13 amino acids from the C-terminus. In embodiments, the polymerase (e.g., a polymerase as described herein) is truncated at the C-terminus, wherein the truncation removes 16 amino acids from the C-terminus.

In embodiments, the polymerase includes a polycationic sequence (e.g., a polyhistidine tag, such as a His-6 tag). To facilitate synthesis and/or purification, in embodiments a His6 tag (i.e., six consecutive histidine amino acids) are ligated to the C or N terminus of the polypeptide chain. It is understood that the presence of a His6 tag enables the isolation of peptide or protein products directly from ligation reaction mixtures by Ni-NTA affinity column purification. For example, common polyhistidine tags are formed of six histidine (6×His tag) residues which are added at the N-terminus preceded by methionine or C-terminus before a stop codon. Alternative polycationic sequences include alternating histidine and glutamine (e.g., three sets of HQ, referred to as an HQ tag) or alternating histidine and asparagine (e.g., six sets of HN, referred to as an HN tag).

In another aspect is provided a nucleic acid encoding a mutant or improved DNA polymerase as described herein, a vector comprising the recombinant nucleic acid, and/or a host cell transformed with the vector. In certain embodiments, the vector is an expression vector. Host cells comprising such expression vectors are useful in methods of the invention for producing the mutant or improved polymerase by culturing the host cells under conditions suitable for expression of the recombinant nucleic acid. The polymerases of the invention may be contained in reaction mixtures and/or kits. The embodiments of the recombinant nucleic acids, host cells, vectors, expression vectors, reaction mixtures and kits are as described herein. The full plasmid nucleic acid sequence used to generate a polymerase is provided in SEQ ID NO: 2.

In an aspect is provided a kit, wherein the kit includes a polymerase as described herein. Generally, the kit includes one or more containers providing a composition, and one or more additional reagents (e.g., a buffer suitable for polynucleotide extension). The kit may also include a template nucleic acid (DNA and/or RNA), one or more primer polynucleotides, nucleotides (including, e.g., deoxyribonucleotides, ribonucleotides, labeled nucleotides, and/or modified nucleotides), buffers, salts, and/or labels (e.g., fluorophores). In embodiments, the kit further includes instructions. In embodiments the kit includes one or more enclosures (e.g., boxes, bottles, or cartridges) containing the relevant reaction reagents and/or supporting materials.

Adapters and/or primers may be supplied in the kits ready for use, as concentrates-requiring dilution before use, or in a lyophilized or dried form requiring reconstitution prior to use. If required, the kits may further include a supply of a suitable diluent for dilution or reconstitution of the primers and/or adapters. Optionally, the kits may further include supplies of reagents, buffers, enzymes, and dNTPs for use in carrying out nucleic acid amplification and/or sequencing. Further components which may optionally be supplied in the kit include sequencing primers suitable for sequencing templates prepared using the methods described herein.

In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can include one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid.

III. Methods

In an aspect, a method of incorporating a nucleotide into a nucleic acid sequence is provided. The method includes allowing the following components to interact (e.g., by combining in a reaction vessel under suitable conditions): (i) a nucleic acid template, (ii) a primer that has an extendible 3' end, (iii) a nucleotide solution, and (iv) a polymerase (e.g., a DNA polymerase or a thermophilic nucleic acid polymerase as described herein). The polymerase used in the method includes an amino acid sequence that is at least 80% identical to a continuous 500 amino acid sequence within SEQ ID NO: 1 and includes one or more of the mutations described herein.

In an aspect is provided a method of incorporating a nucleotide into a nucleic acid sequence including combining in a reaction vessel: (i) a nucleic acid template, (ii) a nucleotide solution, and (iii) a polymerase, wherein the polymerase is a polymerase as described herein. In embodiments, the method includes combining the components in a reaction vessel under conditions for incorporating and/or polymerization. Such conditions are known in the art and described herein.

In embodiments, the method includes amplifying the polynucleotide via an isothermal amplification process. Isothermal amplification processes include SDA, LAMP, SMAP, ICAN, SMART. In these techniques, the extension reaction proceeds at a constant temperature, for example using strand displacement reactions. Amplification can be completed in a single step, by incubating the mixture of samples, primers, DNA polymerase with strand displacement activity, and substrates at a constant temperature. This reduces the number of steps required, eliminating thermal ramping steps and reducing the total cycle time for each amplification cycle, while simultaneously decreasing the reaction time required for each cycle.

In another aspect is provided a method of amplifying a nucleic acid sequence including: a. hybridizing a nucleic acid template with a primer to form a primer-template hybridization complex; b. contacting the primer-template hybridization complex with a DNA polymerase and nucleotides (e.g., a plurality of nucleotides, such as native nucleotides), wherein the DNA polymerase is the polymerase as described herein; and c. subjecting the primer-template hybridization complex to conditions which enable the polymerase to incorporate one or more nucleotides into the primer-template hybridization complex to generate amplification products, thereby amplifying a nucleic acid sequence.

In embodiments, the amplification products are double-stranded amplification products. In embodiments, generating a double-stranded amplification product includes amplifying the template polynucleotide or complement thereof on a solid support including a plurality of primers attached to the solid support, wherein the plurality of primers include a plurality of forward primers with complementarity to the template polynucleotide and a plurality of reverse primers with complementarity to a complement of the template polynucleotide, and the amplifying includes a plurality of cycles of strand denaturation, primer hybridization, and primer extension.

In embodiments, the plurality of strand denaturation cycles are different for one or more cycles, wherein the initial denaturation cycle is maintained at different conditions from the remaining denaturation cycles. For example, in embodiments, the initial denaturation cycle is at about 85° C.-95° C. for about 1 minute to about 10 minutes, whereas denaturation in the remaining cycles is different (e.g., about 85° C. for about 15-30 sec). In embodiments, the initial denaturation is maintained at about 85° C.-95° C. for about 5 minutes to about 10 minutes. In embodiments, the initial denaturation is maintained at 90° C.-95° C. for about 1 to 10 minutes. In embodiments, the initial denaturation is maintained at 80° C.-85° C. for about 1 to 10 minutes. In embodiments, the initial denaturation is maintained at 85° C.-90° C. for about 1 to 10 minutes. In embodiments, the initial denaturation is maintained at about 85° C.-95° C. for about 1 minutes to about 10 minutes. In embodiments, the initial denaturation is maintained at about 95° C. for about 5 minutes to about 10 minutes. In embodiments, the initial denaturation is maintained at about 85° C.-95° C. for about 5 minutes to about 10 minutes.

In embodiments, generating a double-stranded amplification product includes a thermal bridge polymerase chain reaction (t-bPCR) amplification. In embodiments, the plurality of cycles includes thermally cycling between (i) about 85° C. for about 15-30 sec for denaturation, and (ii) about 65° C. for about 1 minute for annealing/extension of the primer. In embodiments, the plurality of cycles includes thermally cycling between (i) about 85° C. for about 15-30 sec for denaturation, and (ii) about 65° C. for about 30 seconds for annealing/extension of the primer.

In embodiments, the plurality of cycles includes thermally cycling between (i) about 80° C. to 90° C. for denaturation, and (ii) about 55° C. to about 65° C. for annealing/extension of the primer. In embodiments, the plurality of cycles includes thermally cycling between (i) about 85° C. for denaturation, and (ii) about 55° C. for annealing/extension of the primer. In embodiments, the plurality of cycles includes thermally cycling between (i) about 85° C. for denaturation, and (ii) about 65° C. for annealing/extension of the primer. In embodiments, the plurality of cycles includes thermally cycling between (i) less than 80° C. (e.g., 70 to 80° C.) for denaturation, and (ii) about 55° C. to about 65° C. for annealing/extension of the primer. In embodiments, the plurality of cycles includes thermally cycling between (i) about 70° C. for denaturation, and (ii) about 65° C. for annealing/extension of the primer. In embodiments, the plurality of cycles includes thermally cycling between (i) about 75° C. for denaturation, and (ii) about 55° C. for annealing/extension of the primer. In embodiments, the plurality of cycles includes thermally cycling between (i) about 85° C. for denaturation, and (ii) about 65° C. for annealing/extension of the primer.

In embodiments, the plurality of cycles includes thermally cycling between (i) about 85° C. for less than 1 minute for denaturation, and (ii) about 65° C. for about 1 to 2 minutes for annealing/extension of the primer. In embodiments, the plurality of cycles includes thermally cycling between (i) about 85° C. for less than 1 minute for denaturation, and (ii) about 60° C. to about 65° C. for about 1 minute for annealing/extension of the primer. In embodiments, the plurality of cycles includes thermally cycling between (i) about 85° C. for about 15-30 sec for denaturation and (ii) about 65° C. for about 1 minute for annealing/extension of the primer. In embodiments, the plurality of cycles includes thermally cycling between (i) about 85° C. for about 30 sec for denaturation and (ii) about 65° C. for about 1 minute for annealing/extension of the primer. In embodiments, the plurality of cycles includes thermally cycling between (i) about 85° C. for about 15-30 sec for denaturation, and (ii) about 65° C. for about 30 seconds for annealing/extension of the primer. In embodiments, the plurality of cycles includes thermally cycling between (i) about 85° C. for about 15-30 sec for denaturation, and (ii) about 65° C. for about 1 minute for annealing/extension of the primer. In embodiments, the temperature and duration for the annealing of the primer and the extension of the primer are different. In embodiments, the plurality of cycles includes thermally cycling between (i) about 90° C. to 95° C. for about 15 to 30 sec for denaturation and (ii) about 55° C. to about 65° C. for about 30 to 60 seconds for annealing and about 65° C. to 70° C. for about 30 to 60 seconds for extension of the primer. In embodiments, the plurality of denaturation steps is at a temperature of about 80° C.-95° C. In embodiments, the plurality of denaturation steps is at a temperature of about 80° C.-90° C. In embodiments, the plurality of denaturation steps is at a temperature of about 85° C.-90° C. In embodiments, the plurality of denaturation steps is at a temperature of about 81° C., 82° C., 83° C., 84° C., 85° C., 86° C., 87° C., 88° C., 89° C., or about 90° C. In embodiments, the plurality of denaturation steps is at a temperature of about 91° C., 92° C., 93° C., 94° C., 95° C., 96° C., 97° C., 98° C., or about 99° C. In embodiments, the plurality of denaturation steps is at a temperature of about 87° C., 88° C., 89° C., 90° C., 91° C., 92° C., 93° C., 94° C., or about 95° C. In embodiments, the plurality of denaturation steps is at a temperature of about 90° C., 91° C., 92° C., 93° C., 94° C., or about 95° C. In embodiments, the plurality of denaturation steps is at a temperature of about 70° C.-85° C. In embodiments, the plurality of denaturation steps is at a temperature of about 70° C.-80° C. In embodiments, the plurality of denaturation steps is at a temperature of about 75° C.-80° C. In embodiments, the plurality of denaturation steps is at a temperature of about 70° C., 71° C., 72° C., 73° C., 74° C., 75° C., 76° C., 77° C., 78° C., 79° C., or about 80° C. In embodiments, the annealing/extension of the primer cycle is at a temperature of about 55° C., 56° C., 57° C., 58° C., 59° C., 60° C., 61° C., 62° C., 63° C., 64° C., or about 65° C.

In embodiments, the method includes includes exponential rolling circle amplification (eRCA). Exponential RCA is similar to the linear process except that it uses a second primer having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5(1994)).

In embodiments, forming a plurality of amplification products includes hyperbranched rolling circle amplification (HRCA). Hyperbranched RCA uses a second primer complementary to the first amplification product. This allows products to be replicated by a strand-displacement mechanism, which can yield a drastic amplification within an isothermal reaction (Lage et al., Genome Research 13:294-307 (2003), which is incorporated herein by reference in its entirety).

In embodiments, the method includes amplifying a template nucleic acid by extending an amplification primer with a strand-displacing polymerase for about 10 seconds to about 30 minutes. In embodiments, the method includes amplifying a template nucleic acid by extending an amplification primer with a strand-displacing polymerase for about 30 seconds to about 16 minutes. In embodiments, the method includes amplifying a template nucleic acid by extending an amplification primer with a strand-displacing polymerase for about 30 seconds to about 10 minutes. In embodiments, the method includes amplifying a template nucleic acid by extending an amplification primer with a strand-displacing polymerase for about 30 seconds to about 5 minutes. In embodiments, the method includes amplifying a template nucleic acid by extending an amplification primer with a strand-displacing polymerase for about 1 second to about 5 minutes. In embodiments, the method includes amplifying a template nucleic acid by extending an amplification primer with a strand-displacing polymerase for about 1 second to about 2 minutes.

In embodiments, the method includes amplifying a template nucleic acid by extending an amplification primer with a strand-displacing polymerase at a temperature of about 20° C. to about 50° C. In embodiments, the method includes amplifying a template nucleic acid by extending an amplification primer with a strand-displacing polymerase at a temperature of about 30° C. to about 50° C. In embodiments, the method includes amplifying a template nucleic acid by extending an amplification primer with a strand-displacing polymerase at a temperature of about 25° C. to about 45° C. In embodiments, the method includes amplifying a template nucleic acid by extending an amplification primer with a strand-displacing polymerase at a temperature of about 35° C. to about 45° C. In embodiments, the method includes amplifying a template nucleic acid by extending an amplification primer with a strand-displacing polymerase at a temperature of about 35° C. to about 42° C. In embodiments, the method includes amplifying a template nucleic acid by extending an amplification primer with a strand-displacing polymerase at a temperature of about 37° C. to about 40° C.

In embodiments, the nucleic acid template includes one or more adapters. The term “adapter” as used herein refers to any oligonucleotide that can be ligated to a nucleic acid molecule, thereby generating nucleic acid products that can be sequenced on a sequencing platform (e.g., an Illumina or Singular Genomics G4™ sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term “double-stranded adapter” or “blunt-ended” is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., P7 and P5 sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing. In some embodiments, an adapter is hairpin adapter. In some embodiments, a hairpin adapter comprises a single nucleic acid strand comprising a stem-loop structure. In some embodiments, a hairpin adapter comprises a nucleic acid having a 5'-end, a 5'-portion, a loop, a 3'-portion and a 3'-end (e.g., arranged in a 5' to 3' orientation). In some embodiments, the 5' portion of a hairpin adapter is annealed and/or hybridized to the 3' portion of the hairpin adapter, thereby forming a stem portion of the hairpin adapter. In some embodiments, the 5' portion of a hairpin adapter is substantially complementary to the 3' portion of the hairpin adapter. In certain embodiments, a hairpin adapter comprises a stem portion (i.e., stem) and a loop, wherein the stem portion is substantially double stranded thereby forming a duplex. In some embodiments, the loop of a hairpin adapter comprises a nucleic acid strand that is not complementary (e.g., not substantially complementary) to itself or to any other portion of the hairpin adapter. In some embodiments, a method herein comprises ligating a first adapter to a first end of a double stranded nucleic acid, and ligating a second adapter to a second end of a double stranded nucleic acid. In some embodiments, the first adapter and the second adapter are different. For example, in certain embodiments, the first adapter and the second adapter may comprise different nucleic acid sequences or different structures. In some embodiments, the first adapter is a Y-adapter and the second adapter is a hairpin adapter. In some embodiments, the first adapter is a hairpin adapter and a second adapter is a hairpin adapter. In certain embodiments, the first adapter and the second adapter may comprise different primer binding sites, different structures, and/or different capture sequences (e.g., a sequence complementary to a capture nucleic acid). In some embodiments, some, all or substantially all of the nucleic acid sequence of a first adapter and a second adapter are the same. In some embodiments, some, all or substantially all of the nucleic acid sequence of a first adapter and a second adapter are substantially different.

In embodiments, the nucleic acid template includes common sequences at their 5' and 3' ends. In this context the term “common” is interpreted as meaning common to all templates in the library. For example, the double-stranded amplification product may include a first adapter sequence at the 5' end and a second adapter sequence at the 3' end. Typically, the first adapter sequence and the second adapter sequence will consist of no more than 100, or no more than 50, or no more than 40 consecutive nucleotides at the 5' and 3' ends, respectively, of each strand of each template polynucleotide. The precise length of the two sequences may or may not be identical. The precise sequences of the common regions are generally not material to the invention and may be selected by the user. The common sequences must at least include primer-binding sequences (i.e., regions of complementarity for a primer) which enable specific annealing of primers when the template polynucleotides are in used in a solid-phase amplification reaction. The primer-binding sequences are thus determined by the sequence of the primers to be ultimately used for solid-phase amplification.

In embodiments, the method includes amplifying the template polynucleotide in a cell. In embodiments, the method includes amplifying the template polynucleotide in a tissue. In embodiments, the method includes amplifying the template polynucleotide one a solid support (e.g., a multiwell container). In embodiments, the amplification primer is immobilized on a solid support.

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases (e.g., a polymerase described herein) are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) are known and often comprise at least a suitable polymerase (e.g., a polymerase as described herein), a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

A nucleic acid can be amplified by a thermocycling method or by an isothermal amplification method. In some embodiments, a rolling circle amplification method is used. In some embodiments, amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution-based primers can be used. Non-limiting examples of solid phase nucleic acid amplification reactions include interfacial amplification, bridge amplification, emulsion PCR, WildFire amplification (e.g., US patent publication US20130012399), the like or combinations thereof.

In embodiments, the nucleic acid template is DNA, RNA, or analogs thereof. In embodiments, the nucleic acid template includes a primer hybridized to the template. In embodiments, the nucleic acid template is a primer. Primers are usually single-stranded for maximum efficiency in amplification, but may alternatively be double-stranded. If double-stranded, the primer is usually first treated to separate its strands before being used to prepare extension products. This denaturation step is typically affected by heat, but may alternatively be carried out using alkali, followed by neutralization. Thus, a "primer" is complementary to a nucleic acid template, and complexes by hydrogen bonding or hybridization with the template to give a primer/template complex for initiation of synthesis by a polymerase, which is extended by the addition of covalently bonded bases linked at their 3' end complementary to the template in the process of DNA synthesis. The DNA template for a sequencing reaction will typically comprise a double-stranded region having a free 3' hydroxyl group which serves as a primer or initiation point for the addition of further nucleotides in the sequencing reaction. The region of the DNA template to be sequenced will overhang this free 3' hydroxyl group on the complementary strand. The primer bearing the free 3' hydroxyl group may be added as a separate component (e.g. a short oligonucleotide), which hybridizes to a region of the template to be sequenced. Alternatively, the primer and the template strand to be sequenced may each form part of a partially self-complementary nucleic acid strand capable of forming an intramolecular duplex, such as for example a hairpin loop structure. Nucleotides are added successively to the free 3' hydroxyl group, resulting in synthesis of a polynucleotide chain in the 5' to 3' direction. After each nucleotide addition the nature of the base which has been added will be determined, thus providing sequence information for the DNA template.

In embodiments, the template polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA).

In embodiments, the template polynucleotide is about 100 to 1000 nucleotides in length. In embodiments, the template polynucleotide is about 500 to 2000 nucleotides in length. In embodiments, the template polynucleotide is about 1000 to 1000 nucleotides in length. In embodiments, the template polynucleotide is about 50 to 500 nucleotides in length. In embodiments, the template polynucleotide is about 500 to 1000 nucleotides in length. In embodiments, the template polynucleotide is about 350 nucleotides in length. In embodiments, the template polynucleotide is about 10, 20, 50, 100, 150, 200, 300, or 500 nucleotides in length. The template polynucleotide molecules can vary length, such as about 100-300 nucleotides long, about 300-500 nucleotides long, or about 500-1000 nucleotides long. In embodiments, the template polynucleotide molecular is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the template polynucleotide molecule is about 150 nucleotides. In embodiments, the template polynucleotide is about 100-1000 nucleotides long. In embodiments, the template polynucleotide is about 100-300 nucleotides long. In embodiments, the template polynucleotide is about 300-500 nucleotides long. In embodiments, the template polynucleotide is about 500-1000 nucleotides long. In embodiments, the template polynucleotide molecule is about 100 nucleotides. In embodiments, the template polynucleotide molecule is about 300 nucleotides. In embodiments, the template polynucleotide molecule is about 500 nucleotides. In embodiments, the template polynucleotide molecule is about 1000 nucleotides.

In embodiments the template polynucleotide (e.g., genomic template DNA) is first treated to form single-stranded linear fragments (e.g., ranging in length from about 50 to about 600 nucleotides). Treatment typically entails fragmentation, such as by chemical fragmentation, enzymatic fragmentation, or mechanical fragmentation, followed by denaturation to produce single-stranded DNA fragments. In embodiments, the template polynucleotide includes an adapter. The adapter may have other functional elements including tagging sequences (i.e., a barcode), attachment sequences, palindromic sequences, restriction sites, sequencing primer binding sites, functionalization sequences, and the like. Barcodes can be of any of a variety of lengths. In embodiments, the primer includes a barcode that is 10-50, 20-30, or 4-12 nucleotides in length. In embodiments, the adapter includes a primer binding sequence that is complementary to at least a portion of a primer (e.g., a sequencing primer). Primer binding sites can be of any suitable length. In embodiments, a primer binding site is about or at least about 10, 15, 20, 25, 30, or more nucleotides in length. In embodiments, a primer binding site is 10-50, 15-30, or 20-25 nucleotides in length.

In embodiments, the template polynucleotide and the double-stranded amplification products include known adapter sequences on the 5' and 3' ends. In embodiments, the template polynucleotide includes known adapter sequences on the 5' and 3' ends. In embodiments, the double-stranded amplification products include known adapter sequences on the 5' and 3' ends.

In some embodiments, the reaction conditions for amplification includes incubation in a denaturant. As used herein, the terms "denaturant" or plural "denaturants" are used in accordance with their plain and ordinary meanings and refer to an additive or condition that disrupts the base pairing between nucleotides within opposing strands of a double-stranded polynucleotide molecule. The term "denature" and its variants, when used in reference to any double-stranded polynucleotide molecule, or double-stranded polynucleotide sequence, includes any process whereby the base pairing between nucleotides within opposing strands of the double-stranded molecule, or double-stranded sequence, is disrupted. Typically, denaturation includes rendering at least some portion or region of two strands of the double-stranded polynucleotide molecule or sequence single-stranded or partially single-stranded. In some embodiments, denaturation includes separation of at least some portion or region of two strands of the double-stranded polynucleotide molecule or sequence from each other.

Typically, the denatured region or portion is then capable of hybridizing to another polynucleotide molecule or sequence. Optionally, there can be "complete" or "total" denaturation of a double-stranded polynucleotide molecule or sequence. Complete denaturation conditions are, for example, conditions that would result in complete separation of a significant fraction (e.g., more than 10%, 20%, 30%, 40% or 50%) of a large plurality of strands from their extended and/or full-length complements. Typically, complete or total denaturation disrupts all of the base pairing between the nucleotides of the two strands with each other. Similarly, a nucleic acid sample is optionally considered fully denatured when more than 80% or 90% of individual molecules of the sample lack any double-strandedness (or lack any hybridization to a complementary strand).

Alternatively, the double-stranded polynucleotide molecule or sequence can be partially or incompletely denatured. A given nucleic acid molecule can be considered partially denatured when a portion of at least one strand of the nucleic acid remains hybridized to a complementary strand, while another portion is in an unhybridized state (even if it is in the presence of a complementary sequence). The unhybridized portion is optionally at least 5, 10, 15, 20, 50, or more nucleotides in length. The hybridized portion is optionally at least 5, 10, 15, 20, 50, or more nucleotides in length. Partial denaturation includes situations where some, but not all, of the nucleotides of one strand or sequence, are based paired with some nucleotides of the other strand or sequence within a double-stranded polynucleotide. In some embodiments, at least 20% but less than 100% of the nucleotide residues of one strand of the partially denatured polynucleotide (or sequence) are not base paired to nucleotide residues within the opposing strand. In embodiments, at least 50% of nucleotide residues within the double-stranded polynucleotide molecule (or double-stranded polynucleotide sequence) are in single-stranded (or unhybridized) from, but less than 20% or 10% of the residues are double-stranded.

Optionally, a nucleic acid sample can be considered to be partially denatured when a substantial fraction of individual nucleic acid molecules of the sample (e.g., above 20%, 30%, 50%, or 70%) are in a partially denatured state. Optionally less than a substantial amount of individual nucleic acid molecules in the sample are fully denatured, e.g., not more than 5%, 10%, 20%, 30% or 50% of the nucleic acid molecules in the sample. Under exemplary conditions at least 50% of the nucleic acid molecules of the sample are partly denatured, but less than 20% or 10% are fully denatured. In other situations, at least 30% of the nucleic acid molecules of the sample are partly denatured, but less than 10% or 5% are fully denatured. Similarly, a nucleic acid sample can be non-denatured when a minority of individual nucleic acid molecules in the sample are partially or completely denatured.

In an embodiment, partially denaturing conditions are achieved by maintaining the duplexes as a suitable temperature range. For example, the nucleic acid is maintained at temperature sufficiently elevated to achieve some heat-denaturation (e.g., above 45° C., 50° C., 55° C., 60° C., 65° C., or 70° C.) but not high enough to achieve complete heat-denaturation (e.g., below 95° C. or 90° C. or 85° C. or 80° C. or 75° C.). In an embodiment the nucleic acid is partially denatured using substantially isothermal conditions. Alternatively, chemical denaturation can be accomplished by contacting the double-stranded polynucleotide to be denatured with appropriate chemical denaturants, such as strong alkalis, strong acids, chaotropic agents, and the like and can include, for example, NaOH, urea, or guanidine-containing compounds. In some embodiments, partial or complete denaturation is achieved by exposure to chemical denaturants such as urea or formamide, with concentrations suitably adjusted, or using high or low pH (e.g., pH between 4-6 or 8-9). In embodiments, the denaturant is a buffered solution including betaine, dimethyl sulfoxide (DMSO), ethylene glycol, formamide, glycerol, guanidine thiocyanate, 4-methylmorpholine 4-oxide (NMO), or a mixture thereof. In embodiments, the first denaturant is a buffered solution including about 0% to about 50% dimethyl sulfoxide (DMSO); about 0% to about 50% ethylene glycol; about 0% to about 20% formamide; or about 0 to about 3M betaine, or a mixture thereof. In an embodiment herein, partial denaturation and/or amplification, including any one or more steps or methods described herein, can be achieved using a recombinase and/or single-stranded binding protein.

In some embodiments, complete or partial denaturation of a double-stranded polynucleotide sequence is accomplished by contacting the double-stranded polynucleotide sequence using appropriate denaturing agents. For example, the double-stranded polynucleotide can be subjected to heat-denaturation (also referred to interchangeably as thermal denaturation) by raising the temperature to a point where the desired level of denaturation is accomplished. In some embodiments, thermal denaturation of a double-stranded polynucleotide, includes adjusting the temperature to achieve complete separation of the two strands of the polynucleotide, such that 90% or greater of the strands are in single-stranded form across their entire length. A completely denatured double-stranded polynucleotide results in a separated first strand and a second strand, each of which is a single-stranded polynucleotide. In some embodiments, complete thermal denaturation of a polynucleotide molecule (or polynucleotide sequence) is accomplished by exposing the polynucleotide molecule (or sequence) to a temperature that is at least 5° C., 10° C., 15° C., 20° C., 25° C., 30° C., 50° C., or 100° C., above the calculated or predict melting temperature (Tm) of the polynucleotide molecule or sequence.

In some embodiments, complete or partial denaturation is accomplished by treating the double-stranded polynucleotide sequence to be denatured using a denaturant mixture including an SSB protein (e.g., T4 gp32 protein, T7 gene 2.5 SSB protein, or phi29 SSB protein, *Thermococcus kodakarensis* (KOD) SSB, *Therms thermophilus* (TTH) SSB, *Sulfolobus solfataricus* (SSO) SSB, or Extreme Thermostable Single-Stranded DNA Binding Protein (ET-SSB)), a strand-displacing polymerase (e.g., Bst large fragment (Bst LF) polymerase, Bst 3.0 polymerase, Bst 2.0 polymerase, Bsu polymerase, SD polymerase, Vent exo-polymerase, Phi29 polymerase, or a mutant thereof), and one or more crowding agents (poly(ethylene glycol) (PEG), polyvinylpyrrolidone (PVP), bovine serum albumin (BSA), dextran, Ficoll (e.g., Ficoll 70 or Ficoll 400), glycerol, or a combination thereof). In embodiments, the crowding agent is poly(ethylene glycol) (e.g., PEG 200, PEG 600, PEG 800, PEG 2,050, PEG 4,600, PEG 6,000, PEG 8,000, PEG 10,000, PEG 20,000, or PEG 35,000), dextran sulfate, bovine pancreatic trypsin inhibitor (BPTI), ribonuclease A, lysozyme, β-lactoglobulin, hemoglobin, bovine serum albumin (BSA), or poly(sodium 4-styrene sulfonate) (PSS). In embodiments, the denaturant mixture including an SSB, a strand-displacing polymerase, and one or more crowding agents does not include a chemical denaturant (e.g., betaine, DMSO, ethylene glycol, formamide, guanidine thiocyanate, NMO, TMAC, or a mixture thereof).

In embodiments, mutation(s) may include substitution of the amino acid in the parent amino acid sequences with an amino acid, which is not the parent amino acid. In embodiments, the mutations may result in conservative amino acid changes. In embodiments, non-polar amino acids may be converted into polar amino acids (threonine, asparagine, glutamine, cysteine, tyrosine, aspartic acid, glutamic acid or histidine) or the parent amino acid may be changed to an alanine.

In embodiments, the method includes maintaining the temperature at about 55° C. In embodiments, the method includes maintaining the temperature at about 55° C. to about 80° C. In embodiments, the method includes maintaining the temperature at about 60° C. to about 70° C. In embodiments, the method includes maintaining the temperature at about 65° C. to about 75° C. In embodiments, the method includes maintaining the temperature at about 65° C. In embodiments, the method includes maintaining the temperature at about 60° C. In embodiments, the method includes maintaining the temperature at a pH of 8.0 to 11.0. In embodiments, the pH is 9.0 to 11.0. In embodiments, the pH is 9.5. In embodiments, the pH is 10.0. In embodiments, the pH is 8.0, 8.5, 9.0, 9.5, 10.0, 10.5, or 11.0. In embodiments, the pH is from 9.0 to 11.0, and the temperature is about 60° C. to about 70° C. In embodiments, the pH is from 8.5 to 9.5, and the temperature is about 58° C. to about 62° C.

In embodiments of the methods and compositions provided herein, the clusters have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 μm or a number or a range between any two of these values. In embodiments, the mean or median separation is about 0.1-10 microns. In embodiments, the mean or median separation is about 0.25-5 microns. In embodiments, the mean or median separation is about 0.5-2 microns. In embodiments, the mean or median separation is about or at least about 0.1 μm. In embodiments, the mean or median separation is about or at least about 0.25 μm. In embodiments, the mean or median separation is about or at least about 0.5 μm. In embodiments, the mean or median separation is about or at least about 1.0 μm. In embodiments, the mean or median separation is about or at least about 2.0 μm. In embodiments, the mean or median separation is about or at least about 5.0 μm. In embodiments, the mean or median separation is about or at least about 10 μm. The mean or median separation may be measured center-to-center (i.e., the center of one cluster to the center of a second cluster). In embodiments of the methods provided herein, the amplicon clusters have a mean or median separation (measured center-to-center) from one another of about 0.5-5 μm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 μm.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1,000, 1,100, 1,200, 1,300, 1,400, 1,500, 1,600, 1,700, 1,800, 1,900, 2000 nanometers or a number or a range between any two of these values. In embodiments, the mean or median diameter is about 100-3,000 nanometers. In embodiments, the mean or median diameter is about 100-2,000 nanometers. In embodiments, the mean or median diameter is about 500-2500 nanometers. In embodiments, the mean or median diameter is about 200-1000 nanometers. In embodiments, the mean or median diameter is about 1,000-2,000 nanometers. In embodiments, the mean or median diameter is about or at most about 100 nanometers. In embodiments, the mean or median diameter is about or at most about 200 nanometers. In embodiments, the mean or median diameter is about or at most about 500 nanometers. In embodiments, the mean or median diameter is about or at most about 400 nanometers. In embodiments, the mean or median diameter is about or at most about 500 nanometers. In embodiments, the mean or median diameter is about or at most about 600 nanometers. In embodiments, the mean or median diameter is about or at most about 700 nanometers. In embodiments, the mean or median diameter is about or at most about 1,000 nanometers. In embodiments, the mean or median diameter is about or at most about 2,000 nanometers. In embodiments, the mean or median diameter is about or at most about 2,500 nanometers. In embodiments, the mean or median diameter is about or at most about 3,000 nanometers.

In embodiments of the methods provided herein, each amplicon cluster (e.g., an amplicon cluster having a mean or median diameter of about 100-2000 nm, or about 200-1000 nm) includes about or at least about 100, 500, 1,000, 2,500, 5,000, 10,000, 15,000, 20,000, 25,000, 30,000, 35,000, 40,000, 45,000, or 50,000 dsDNA molecules. In embodiments, each amplicon cluster includes about 100 dsDNA molecules. In embodiments, each amplicon cluster includes about 500 dsDNA molecules. In embodiments, each amplicon cluster includes about 1000 dsDNA molecules. In embodiments, each amplicon cluster includes about 500 dsDNA molecules. In embodiments, each amplicon cluster includes about 1,000 dsDNA molecules. In embodiments, each amplicon cluster includes about 2,500 dsDNA molecules. In embodiments, each amplicon cluster includes about 5,000 dsDNA molecules. In embodiments, each amplicon cluster includes about 10,000 dsDNA molecules. In embodiments, each amplicon cluster includes about 20,000 dsDNA molecules. In embodiments, each amplicon cluster includes about 30,000 dsDNA molecules. In embodiments, each amplicon cluster includes about 40,000 dsDNA molecules. In embodiments, each amplicon cluster includes about 50,000 dsDNA molecules. In embodiments, each amplicon cluster includes more than about 50,000 dsDNA molecules.

In embodiments, the substrate is a particle. In embodiments, the substrate is a multiwell container. In embodiments, the substrate is a polymer coated particle or polymer coated planar support. In embodiments, the substrate includes a polymer. In embodiments, the particle includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the particle shell includes polymerized units of polyacrylamide (AAm), glicydyl methacrylate (GMA), polyethylene glycol methacrylate (PEGMA), polyethylene glycol methacrylate (PEGMA), isocyanatoethyl methacrylate (IEM), or a copolymer thereof. In embodiments, the particle includes polymerized units of polyethylene glycol methacrylate (PEGMA) and glicydyl methacrylate (GMA). In embodiments, the particle includes polymerized units of polyethylene glycol methacrylate (PEGMA) and isocyanatoethyl methacrylate (IEM). In embodiments, the particle includes polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the particle includes polymerized units of 3-azido-2-hydroxypropyl methacrylate, 2-azido-3-hydroxypropyl methacrylate, or 2-(((2-azidoethoxy)carbonyl)amino)ethyl methacrylate. In embodiments, the particle includes polymerized units of 3-azido-2-hydroxypropyl methacrylate. In embodiments, the particle includes polymerized units of 3-azido-2-hydroxypropyl methacrylate 2-azido-3-hydroxypropyl methacrylate. In embodiments, the particle includes polymerized units of 3-azido-2-hydroxypropyl methacrylate 2-(((2-azidoethoxy)carbonyl)amino)ethyl methacrylate.

In embodiments, the nucleic acid template or the nucleic acid primer are attached to a solid support. In embodiments, the solid support includes about 100, 500, 1000, 5000, 10000, or more primer-template hybridization complex (i.e., dsDNA molecules) in a 2 $\mu m^2$ area. In embodiments, the solid support includes about 1,000 to about 10,000 dsDNA molecules in a 2 $\mu m^2$ area. In embodiments, the solid support includes about 1,000 to about 10,000 dsDNA molecules in a 0.5 μm diameter feature. In embodiments, the solid support includes about 1,000 to about 50,000 dsDNA molecules in a 500, 600, 700, 800, 900, or 1,000 nm diameter feature. In embodiments, the solid support includes about 10,000 to about 50,000 dsDNA molecules in a 500, 600, 700, 800, 900, or 1,000 nm diameter feature. In embodiments, the solid support includes about 20,000 to about 40,000 dsDNA molecules in a 500, 600, 700, 800, 900, or 1,000 nm diameter feature. In embodiments, the solid support includes about 30,000 to about 40,000 dsDNA molecules in a 500, 600, 700, 800, 900, or 1,000 nm diameter feature. As used herein, a feature may be a wells, pits, channels, ridges, raised regions, pegs, or posts on a solid support. Each feature includes a colony and refers to a discrete site on a solid support that includes a plurality of immobilized polynucleotides.

In embodiments, the polymerases described herein have improved polymerase activity (i.e., improved relative to a control). Polymerase activity, in some instances, includes the measurable quantity $k_{cat}$, $k_{cat}/K_m$, or yields of incorporated nucleotides for a given time period. In embodiments, the polymerases described herein have increased extension activity (i.e., increased relative to a control). Increased extension activity variously refers to an increase in reaction kinetics (increased $k_{cat}$), increased $K_D$, decreased $K_m$, increased $k_{cat}/K_m$ ratio, faster turnover rate, higher turnover number, or other metric that is beneficial to the use of the polypeptide for nucleic acid extension with nucleotides. The polypeptides described herein often incorporate at least 30% more nucleotides than the wild-type polymerase in total or in a given duration of time.

In embodiments, the polymerases described herein often incorporate at least 10%, 20%, 30%, 50%, 75%, 100%, 125%, 150%, 200%, 500%, more nucleotides than a control (e.g., the wild-type polymerase) for a fixed amount of time and same nucleotide concentration. In embodiments, the polymerases described herein incorporate nucleotides at least 1.5, 2, 2.5, 5, 10, 15, 20, 25, or at least 50 times faster than a control (e.g., the wild-type polymerase) for a fixed amount of time. Such measurements are often measured under conditions such as a set period of time, such as at least, at most, or exactly 1, 2, 3, 5, 8, 10, 15, 20, or more than 20 minutes. Such measurements are often measured under conditions such as a set nucleotide concentration, such as less than 10 uM, 10 uM, 20 uM, 50 uM, 100 uM, 200 uM, 300 uM, 500 uM, or more than 500 uM, or any concentration within the range identified herein It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1. Focused Mutational Analysis

DNA amplification has many applications in molecular biology research and medical diagnostics. There are two main strategies for amplifying a defined sequence of nucleic acid: polymerase chain reaction (PCR) and isothermal amplification. The polymerase chain reaction relies upon thermal cycling to denature dsDNA templates, followed by annealing primers at specific sites in the denatured template, and extension of the primers by a thermostable DNA polymerase. Isothermal amplification of DNA, as the name implies, typically includes amplification of the dsDNA at a defined temperature. The lack of thermal cycling in isothermal amplification technologies reduces equipment needs and improves the time to answer, especially for point-of-care applications.

A variety of isothermal amplification methods have been developed, for example, strand displacement amplification (SDA) (Walker, G. T. et al. Nucleic Acids Res 20, 1691-6 (1992); and Walker, G. T., Little, M. C, Nadeau, J. G. & Shank, D. D. PNAS 89, 392-6 (1992)), rolling circle amplification (RCA) (Fire, A. & Xu, S. Q. PNAS 92, 4641-5 (1995)), cross priming amplification (CPA) (Xu, G. et al. Sci. Rep. 2, 246; (2012)) and loop mediated amplification (LAMP) (Notomi, T. et al. Nucleic Acids Res 28, e63 (2000)). While some isothermal amplification mechanisms depend upon multiple enzymes, e.g., nickases, recombinases, and ligases, to achieve continuous replication, RCA and LAMP require only polymerases and primers. These methods, like many other isothermal amplification methods, require the use of a DNA polymerase with a strong strand displacement activity to displace downstream DNA, thereby enabling continuous replication without thermal cycling. Additionally, efficient amplification requires elevated temperatures (e.g., 60° C. or greater) to enable the annealing of primers at specific locations on the dsDNA. Thus, a DNA polymerase suitable for these methods must be a thermostable DNA polymerase with a strong strand displacement activity.

Few thermostable, strand displacing enzymes exist. For example, SD DNA polymerase (a mutant Taq DNA polymerase) and the large fragment of Bst DNA polymerase possess favorable characteristics for isothermal amplification. *Bacillus stearothermophilus* (Bst) DNA Polymerase I is a member of polymerase family A and is one of the most popular enzymes with strand displacement activity because its optimum is about 63° C. Unfortunately, Bst polymerase is limited to temperatures up to 68-70° C.; at temperature 68° C. or higher it is inactivated (Xu, G. et al. Sci. Rep. 2, 246; (2012)). This complicates the workflow, since many isothermal amplification approaches depend on an initial heating step (e.g., to about 95° C.) to denature dsDNA templates. An aim of the general experimental plan was to produce a robust, optimized polymerase for nucleic acid sequencing methods. DNA polymerases of the *Pyrococcus* genus share similar anerobic features as other thermophilic genera (e.g., *Archaeoglobus, Thermoautotrophican, Methanococcus*), however, *Pyrococcus* species thrive in higher temperatures, ca 100° C., and tolerate extreme pressures. For example, the area around undersea hot vents, where *P. abyssi* has been found, there is no sunlight, the temperature is around 98° C.-100° C. and the pressure is about 200 atm. These *Pyrococcus* polymerases possess inherent properties that are beneficial for sequencing applications.

Directed evolution of enzymes is a process that mimics natural selection in vitro. Compartmentalized self-replication (CSR) is a method of directed evolution where a library containing mutated variants of the enzyme of interest goes through rounds of selective pressure, and over time, the most active or best performing variants are enriched in the library, compared to less active variants, as described in Abil, Z., & Ellington, A. D. (2018). *Current Protocols in Chemical Biology,* 10, 1-17. During CSR, the enzyme variants and its own encoding genes are compartmentalized in oil emulsions, together with dNTPs and primers. During the emulsion PCR, each enzyme that can surpass the selective pressure is able to replicate its own encoding gene and pass to the next round of selection. Over time, the best performers are enriched in the library.

DNA polymerases carry out crucial functions in many DNA metabolic processes, and due to their ability to catalyze the replication of DNA by incorporating nucleotides into the 3' end of a primer annealed to a template, DNA polymerases are frequently used in genomic research (e.g., next-generation sequencing, or NGS, technologies). The human genome encodes at least 14 DNA-dependent DNA polymerases, each serving a particular function. The general classification includes five different classes according to their function: DNA polymerase (Pol $\alpha$) catalyzes DNA replication at Okazaki fragments on the lagging strand; Pol $\beta$ participates in base-excision repair; Pol $\gamma$ is involved in mitochondrial DNA synthetic processes; Pol $\delta$ participates in lagging-strand synthesis; and Pol $\varepsilon$ catalyzes the synthesis of the leading strand of chromosomal DNA.

Structural analyses of DNA polymerases portray the enzyme as analogous to a human right hand, with three domains: a 'fingers' domain that interacts with the incoming dNTP and paired template base, and that closes at each nucleotide addition step; a 'palm' domain that catalyzes the phosphoryl-transfer reaction; and a 'thumb' domain that interacts with duplex DNA. The finger and palm subdomains of DNA polymerases (e.g., amino acids positions 448-603 of SEQ ID NO:1) are in close proximity to the nucleotide incorporation region. We initially limited our mutational analysis to mutations within the finger and palm subdomains (i.e., examining mutations in amino acids positions 448-603 of SEQ ID NO:1) before broadening out mutational analysis to the entire enzyme sequence (see, Example 2).

For brevity, amino acid mutation nomenclature is used throughout this application. One having skill in the art would understand the amino acid mutation nomenclature, such that D141A refers to aspartic acid (single letter code is D), at position 141, is replaced with alanine (single letter code A). Likewise, it is understood that when an amino acid mutation nomenclature is used and the terminal amino acid code is missing, e.g., P411, it is understood that no mutation was made relative to the wild type. Additionally, for amino acid positions that are frequently mutated herein, the wild type amino acid may be recited to emphasize that it is not mutated, for example P411P.

Prior to performing CSR, an error prone PCR library was generated with a target error rate of 6 to 8 mutations per clone using a mutant sequencing enzyme having homology to the sequence SEQ ID NO:3. The mutations were restricted to the approximately 155 amino acids within the finger and palm subdomain, which corresponds to about 465 nucleotides in the gene vector. The library was cloned using a commercial vector pET21b+ via Gibson Assembly, using the Gibson Assembly® Master Mix (NEB Catalog Number E2611S), using the standard protocol described in Gibson, D. G. et. al. (2009) Nature Methods, 343-345 and Gibson, D. G. et al. (2010) Nature Methods, 901-903. Gibson Assembly was developed by Dr. Daniel Gibson and colleagues at the J. Craig Venter Institute and licensed to NEB by Synthetic Genomics, Inc. It allows for successful assembly of multiple DNA fragments, regardless of fragment length or end compatibility. Gibson Assembly efficiently joins multiple overlapping DNA fragments in a single-tube isothermal reaction. The end result is a double-stranded fully sealed DNA molecule that can serve as template for PCR, RCA or a variety of other molecular biology applications. The assembled plasmids containing the diverse inserts were then purified utilizing the Monarch® PCR & DNA Cleanup Kit (NEB Catalog Number T1030L), and then transformed into T7 Express Electrocompetent *E. coli* cells (NEB Catalog Number C3026J). After plating the transformed cells, the library size as determined by the colony forming units (CFU) was estimated to be about $3.8\times10^6$.

The transformed cells were cultured in LB media overnight, and on the next day, protein expression was induced with Isopropyl-beta-D-thiogalactoside (IPDG). On the following day, the emulsion PCR was performed using the oil/surfactant mixtures containing Mineral oil, non-ionic emulsifier (e.g., polaxamer 124, polaxamer 181, or ABIL® EM 90), and a surfactant (e.g., Triton X-100). This mixture was added to the ePCR master mixes, containing a buffer, CSR primer oligonucleotides, BSA, dNTPs, and $1\times10^8$ cells. The emulsion was made using a TissueLyser (Qiagen®).

The emulsion PCR program was designed according to the selective pressure used, modulating the number and type of primers for each round. The product from the emulsion PCR was extracted from emulsion using the method known in the art, for example described by Williams et al. Nat Methods. 2006 July; 3(7):545-50. A recovery PCR reaction is performed using the product from the ePCR as a template. New primers and PCR programs are designed for this purpose. After that, a third PCR reaction is performed using the Recovery PCR's product as a template. The product from the Re-Amp PCR is then cloned into a commercial vector (pET21b+) via Gibson Assembly, and an additional selection round occurs.

To promote strand displacement, the selective pressure applied included i) progressively increasing the amount of double stranded regions within a nucleic acid template (i.e., increasing the amount of blocking oligos), and ii) decreasing the temperature to promote dsDNA formation. CSR primers would anneal to the template and after a few base pairs, the enzyme encountered one or more blocking primer(s), i.e., an oligonucleotide complementary to a region downstream of the CSR primers. Only the enzyme capable of displacing the double-stranded region would be able to replicate its own encoding gene, and therefore would be enriched in the library. A total of 6 rounds of selective pressure were performed, as described in Table 1 below.

TABLE 1

Selective pressure on the finger and palm subdomains. The conditions were progressively modulated to decrease the reaction temperature and progressively increase the amount of double stranded regions within a nucleic acid template (i.e., the quantity of blocking oligos).

| Round Number | Selective Pressure |
|---|---|
| Round 1 | Amplification at 72° C. |
| Round 2 | Amplification at 68° C. |
| Round 3 | Amplification at 66° C. and 2X concentration of blocking oligos |
| Round 4 | Amplification at 63° C. and 2X concentration blocking oligos |
| Round 5 | Amplification at 60° C. and 2X concentration of blocking oligos |
| Round 6 | Amplification at 60° C. and 4X concentration of blocking oligos |

The primers were designed to have a sequence that is the complement of a region of template/target DNA to which the primer hybridizes. A number of primer design tools exist, for example PrimerSelect (Plasterer TN. PRIMERSELECT. Primer and probe design, Methods Mol. Biol., 1997, vol. 70 (pg. 291-302)), Primer Express (Applied BiosystemsPrimer Express® Software Version 3.0 Getting Started Guide, 2004), OLIGO 7 (Rychlik W. OLIGO 7 primer analysis software, Methods Mol. Biol., 2007, vol. 402 (pg. 35-60)) and Primer3 (Untergasser, A. et al. Primer3-new capabilities and interfaces. Nucleic Acids Res 40, e115 (2012)). CSR primers contain a non-complimentary region at the 5' end ("tag") so that the product can be extracted and enriched via PCR. The tags are used to prevent the carry-over and accumulation of amplifications resulting from background amplifications (amplification of DNA polymerase sequences that were not selected for in the ePCR step but were carried over as parental plasmid DNA to recovery PCR).

Blocking oligos were designed to bind downstream of the CSR primer binding region, and had the 3' end blocked with a C3 spacer to prevent extension from the 3' end. Primers were designed taking into consideration the necessary Melting Temperatures, since one of the selective pressures was reduced extension temperature. Calculating the melting temperature and performing thermodynamic modelling for estimating the propensity of primers to hybridize with other primers or to hybridize at unintended sites in the template offer an accurate approach for predicting the energetic stability of DNA structures. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium).

The sequencing data from each mutant was analyzed to identify mutations in the nucleotide level, which were then translated to amino acids. The amino acid mutations calculated frequency of each mutation per round was obtained. The CSR Library was narrowed over the rounds of selection and shows many enriched mutations that are involved in strand-displacement. After each round of selection, the sequence of the enzyme was obtained to elucidate which mutations are responsible for the strand-displacement activity. Table 2 provides an overview of some of the mutations within the finger and palm subdomain responsible for increased strand displacing activity. Using the CSR techniques, novel mutations in the finger/palm subdomains in a DNA polymerase were found. For example, the mutations identified in over 30% of the mutant enzymes are identified in Table 2.

TABLE 2

| Summary of point mutations identified in strand-displacing mutants; the point mutations are relative to SEQ ID NO: 1. Point mutation |
|---|
| F588L |
| F588I |
| Q520H |
| E580G |
| K465E |
| A491V |
| K472E |

Example 2. Broader Mutational Analysis

Simultaneously, we extended the mutational analysis to the entire enzyme and not limiting it to a particular subdomain (e.g., the finger or palm subdomain). Prior to performing CSR, an error prone PCR library was generated with a target error rate of 8 to 15 mutations per clone using a mutant sequencing enzyme having the sequence of SEQ ID NO:1. The library was cloned using pET21b+ following standard restriction enzyme digestion and ligation as well as a commercial vector pD431-SR from ATUM via Gibson Assembly, using the Gibson Assembly® Master Mix (NEB Catalog Number E2611S), as described above.

Both libraries were subjected to 10 rounds of selective pressure, described in Table 3, wherein each round decreased the reaction temperature and/or increased the concentration of blocking oligos.

TABLE 3

Description of the selective pressure dimensions utilized to develop strand-displacing variants.

| | Selection Pressure | | | |
|---|---|---|---|---|
| Round # | Denaturation Tr | Extension temperature | Extension time | Excess blocking oligos |
| Round 1 | 91° C. | 72° C. | 3 min | 0 |
| Round 2 | 91° C. | 72° C. | 3 min | 0 |
| Round 3 | 91° C. | 68° C. | 3 min | 0 |
| Round 4 | 91° C. | 64° C. | 3 min | 2X |
| Round 5 | 91° C. | 60° C. | 3 min | 2X |
| Round 6 | 91° C. | 60° C. | 3 min | 4X |
| Round 7 | 91° C. | 57° C. | 3 min | 4X |
| Round 8 | 91° C. | 55° C. | 2 min | 4X |
| Round 9 | 96° C. | 55° C. | 1 min | 4X |
| Round 10 | 98° C. | 55° C. | 30 seconds | 4X |

An additional selective pressure was applied in later rounds, decreasing the reaction time from 3 minutes to a total extension time of 30 seconds, to provide enzymes with strand-displacing activity and accelerated processivity. A total of 195 unique point mutations were observed, however, the mutations occurring at the highest frequency are provided in Table 4.

TABLE 4

Summary of some of the point mutations identified in strand-displacing mutants; the point mutations are relative to SEQ ID NO: 1. Point mutations

| | |
|---|---|
| Y7H | A491V |
| K13R | R526H |
| A40V | E579G |
| F75L | F588L |
| R97C, H | T606I |
| G149D | G635D |
| K192R | V637D |
| K199E | N672D |
| F241I | H726D |
| M275L | V742A |
| A316S | F749Y |
| K395E | G765D |
| K469T | W769R |
| K472N | |

Example 3. Strand Displacing Assay

Random clones from the library including one or more of the high-frequency mutations, as well as new variants based on the enriched mutations, were screened for strand-displacement activity. The strand displacement assay was developed to measure the strand-displacing activity of the mutants, as described in Harris et al. BioTechniques 54:93-97 (February 2013), such that when extension occurs from the outer primer, it displaces the extension strand produced from the inner primer by utilizing a polymerase that has strand displacement activity. Briefly, the assay includes annealing two outer primers, PrimA and PrimD, to a template nucleic acid. Two or more inner primers are annealed to the template, Prim B and PrimC, wherein the primers hybridize to complementary regions between the outer primers. No strand-displacement activity is required to amplify from the inner primers (e.g., generating small fragments from PrimB to PrimC). Variants possessing strand-displacing activity are capable of generating amplification products from the outer primers and the inner primers. The results of the strand-displacement assay are provided in Table 5.

TABLE 5

Results of the strand displacing assay. A '+' is indicative of strand-displacing activity detection, whereas a '−' indicates no strand-displacing activity was detected. The point mutations provided below are relative to SEQ ID NO: 1.

| Internal Ref No. | SD products detected | Mutations |
|---|---|---|
| AMP1 | + | Q91H; R97H; D215G; G245S; D246E; G350S; R467C; K469T; A516S; E579G; F588L; H726D; V742A |
| AMP2 | + | Y7H; K13R; Q91H; R97H; D215G; G245S; D246E; G350S; R467C; K469T; E579G; F588L; H634Y; H726D; V742A |

TABLE 5-continued

Results of the strand displacing assay. A '+' is indicative of strand-displacing activity detection, whereas a '−' indicates no strand-displacing activity was detected. The point mutations provided below are relative to SEQ ID NO: 1.

| Internal Ref No. | SD products detected | Mutations |
|---|---|---|
| AMP3* | + | Y7H; N132S; E148G; I158V; D215E; K240M; G323S; E383G; K395R; G448S; K469E; K478R; F583L; E600K; G635D; E638D; A676V; R690H; R706H; V742A; **Q759**; G765D; W769R; K773E; G776D |
| AMP4* | + | Y7H; K13R; A56V; I65V; R97C; E182D; S186C; R193H; P217S; Y279C; L333M; R364C; F446S; R526H; Y580C; F588L; T606I; A630G; H726D; **W758**; **W769** |
| AMP5* | + | K52R; V62G; I65V; R97C; E148D; T208S; K289R; I295N; E314D; R426H; K466Q; R483C; A491V; Q520H; R526H; R527H; G550V; F588L; T591A; 1611V; K642E; V644M; H726D; V742A; K752R; G767D; **W769**; I770M |
| AMP6 | + | N23Y; F26S; D45N; V93I; R97H; E133V; I160V; A168T; A316P; R324H; S347N; K395E; L397M; Q462L; V514I; F588L; G635V; N636D; V656I; H726D; R753S; W769L |
| AMP7* | | Y7H; D11G; H59L; R97H; F116L; M129T; E148D; K154E; F214I; I282T; G302D; K395E; E430Q; D566Y; E579G; F588L; V637D; H726D; V742A; W769R; **K774** |
| AMP8 | + | E25V; I71N; R97H; G155D; S247I; A331D; K395E; K469N; K478M; L544P; R559H; E579G; F588L; T623I; H726D; V742A; K774E |
| AMP9 | + | Y7H; K13R; F75L; R97C; A117T; K229T; F283S; T319S; E579G; F588L; N653T; K693N; V742A; K762E; W769L; G776S |
| AMP10 | + | Y7H; I8V; N23D; V66A; F75L; R97C; P217Q; F283S; K297E; T319S; T349A; R526H; E579G; F588L; M688V; H726D; Q737R; V742A |
| AMP11 | + | Y7H; K13R; I38F; A40V; D98N; I109V; D141G; G149D; A168P; I176V; K192R; K199E; F214I; P286Q; A292T; R307S; S348N; K465N; C507S; R526H; G550D; F588L; T606I; E655D; R706C; V742A; W769R |
| AMP12 | + | I51V; E67G; R97G; P104S; F116L; A139V; I142F; I207V; F261S; A292V; K465N; Q484L; E579G; F588L; T623A; K660Q; H726D; V742A; K752E; W769R |
| AMP13* | + | E22K; K52R; I65V; Q57H; R97C; K174E; D215G; G245S; D246E; G350S; R467C; K469T; E579G; F588L; H726D; V742A; **W758** |
| AMP14 | + | Y7H; K13R; I65V; R97C; D98E; A117T; M190V; K289T; K317E; K391T; E579G; F588L; V742A; K771E |
| AMP15 | + | E25K; R97C; A168T; R255H; F326Y; K478R; R526H; E556K; K558N; P573S; E581N; F588L; E600K; E601K; R686H; R724H; V742A; K752E; K762N |
| AMP16 | + | Y7H; K13I; F75L; R97L; I160V; V170I; A316P; K469E; A491V; E579G; F588L; V637D; H726D; V742A |
| AMP17* | + | Y7H; K13R; E50D; F75L; R97C; F214I; Y320F; F326Y; E378V; E427D; K463N; I464V; R532H; V551I; F588L; E665K; R690H; Y751H; **L756** |
| AMP18 | + | Y7H; K13R; I38F; A40V; D49E; F75I; I109V; D141G; G149D; A168P; I176V; K192R; K199E; F214I; K289; A292T; R307S; S348N; K465N; C507S; K558R; F588L; G635D; Y664; I667L; A730E; V742A; Q763; G765D; K773R |
| AMP19 | + | Y7H; K13R; A40V; R97H; F116L; A117S; K154E; A281T; I415V; K477I; K552N; N569S; E577K; A585G; F588I; E655D; V742A |
| AMP20 | + | Y7F; A40V; I109V; D141G; G149D; A168P; I176V; K192R; K199E; F214I; P239L; T272A; A292T; R307S; S348N; K465N; C507S; E579G; F588L; V742A; K773E; K774M |
| AMP21 | + | Y7H; K13R; I38F; A40V; R97C; D141A; P286L; G350S; R467C; K469T; E579G; F588L; F721Y; H726D; V742A; L756C; R757A; W758G; Q759R; T761P; K762N; Q763R; V764L; G765V |
| AMP22 | + | Y7H; I18V; R97C; A168S; F214S; G284S; P286Q; A292V; G304D; K391I; E431D; K477I; Y567H; E579G; F588L; H726D |
| AMP23 | + | Y7H; K13R; V63I; F75L; R97C; E130D; F214S; F326Y; K391I; K478R; E618G; R706C; H726Y; I745L; F749Y |
| AMP24 | + | V63A; F75L; R97C; D98G; R188H; F214I; G245S; D246E; T319I; G350S; E579G; F588L; R690H; H726D; V742A; K760N |

TABLE 5-continued

Results of the strand displacing assay. A '+' is indicative of strand-displacing activity detection, whereas a '−' indicates no strand-displacing activity was detected. The point mutations provided below are relative to SEQ ID NO: 1.

| Internal Ref No. | SD products detected | Mutations |
|---|---|---|
| AMP25 | + | Y7H; I8V; N23D; V66A; F75L; R97C; P217Q; A298S; A316P; K465E; R526H; E577K; E601D; T606I; E655D; R706C; V742A; W769S |
| AMP26 | + | E29D; Y30F; R97H; I160V; K229E; A511V; I548V; F588L; G635D; V742A |
| AMP27 | + | Y7Q; I38F; A40V; Y86H; R97C; F261I; A296T; V434I; K437N; K465E; R526H; A561S; N569K; F588L; T606I; V644M; N672D; K693I; V742A; W758; W769R |
| AMP28 | + | K13R; R32H; F75L; R97C; K201I; Y209H; I256V; Y291H; E383D; G400D; R526C; E579G; F588L; E638G; A730V |
| AMP29 | + | F75L; R97C; I142T; V278I; A281T; A292E; M329L; P372S; H440N; E563G; E579G; F588L; D729Y; V742A |
| AMP30* | + | Y7H; R97L; I176F; L275P; Y279F; Q332P; V438I; L479Q; K535R; R560H; D566G; F588L; T591A; V644M; A676V; H726D; **L756** |
| AMP31 | + | Y7H; K13R; I38F; A40V; I65T; V93I; I109V; G149D; A168P; I176V; K192R; K199E; F214I; A292T; R307S; S348N; K465N; C507S; F588L; G635D; K660E; A676V; R690H; R706H; V742A; Q759; G765D; G767V; W769R; G776D |
| AMP32 | + | Y7H; K13R; I51V; E67G; I96F; R97S; F110L; K154M; I207V; K289N; E386D; E430D; K469T; S471L; R560H; F588L; T591A; W616C; V644M; A676V; H726D; L756 |
| AMP33 | + | I65V; R97H; F283S; V308M; K465E; F588L; T591A; I604M; G635D; K727T |
| AMP34 | + | Y7H; K13R; L76P; K192E; K289T; R364C; L397M; Q484H; E563G; F588L; V637D; R706H; V742A; L766P |
| AMP35 | + | Y7H |
| AMP36 | + | K13R |
| AMP37 | + | Q91H |
| AMP38 | + | R97H |
| AMP39 | + | R97C |
| AMP40 | + | D215G |
| AMP41 | + | D215E |
| AMP42 | + | G245S |
| AMP43 | | D246E |
| AMP44 | | G350S |
| AMP45 | | R467C |
| AMP46 | | K469T |
| AMP47 | − | R467C & K469T |
| AMP48 | + | E579G |
| AMP49 | + | F588L |
| AMP50 | + | E579G & F588L |
| AMP51 | + | H634Y |
| AMP52 | + | H726D |
| AMP53 | | V742A |
| AMP54 | + | N23Y |
| AMP55 | + | F26S |
| AMP56 | − | V742A/F588L |
| AMP57 | + | Y7H/R97H |
| AMP58 | + | Y7H/R97C |
| AMP59 | | V742A/H726D |
| AMP60 | | W769R |
| AMP61 | | R753S |
| AMP62 | | D45N |
| AMP63 | | E133V |
| AMP64 | | R97H/V742A/F588L |
| AMP65 | | Y7H/V742A/F588L |
| AMP66 | | E579G/V742A/F588L |
| AMP67 | | H726D/V742A/F588L |
| AMP68 | | W769L |

Clones from the library including one or more of the high-frequency mutations, as well as new variants based on the enriched mutations, were screened for strand-displacement activity and the point mutations providing increased strand-displacing activity (increased relative to a control, SEQ ID NO:1) are provided in Table 5. Some of the proteins were smaller and displayed different thermal stability profile than the control; investigating the amino acid sequence and the encoding polynucleotide sequence identifies one or more stop codons. A stop codon is a nucleotide triplet that signals the termination of the translation process of the current polypeptide. The smaller enzymes are indicated in Table 5 by a identifier, and the corresponding bold amino acid (e.g., L756 of AMP 17) is associated with the stop codon.

SEQUENCES

Amino Acid Sequence of wild type *P. horikoshii* OT3 (SEQ ID NO: 1):
MILDADYITEDGKPIIRIFKKENGEFKVEYDRNFRPYIYALLRDDSAIDEIKKITAQRHGKVVRIVETEKI
QRKFLGRPIEVWKLYLEHPQDVPAIRDKIREHPAVVDIFEYDIPFAKRYLIDKGLTPMEGNEKLTFLAVDI
ETLYHEGEEFGKGPVIMISYADEEGAKVITWKKIDLPYVEVVSSEREMIKRLIRVIKEKDPDVIITYNGDN
FDFPYLLKRAEKLGIKLLLGRDNSEPKMQKMGDSLAVEIKGRIHFDLFPVIRRTINLPTYTLEAVYEAIFG
KPKEKVYADEIAKAWETGEGLERVAKYSMEDAKVTYELGREFFPMEAQLARLVGQPVWDVSRSSTGNLVEW
EGCEEYDVAPKVGHRFCKDFPGFIPSLLGQLLEERQKIKKRMKESKDPVEKKLLDYRQRAIKILANSYYGY
YGYAKARWYCKECAESVTAWGROYIDLVRRELEARGFKVLYIDTDGLYATIPGVKDWEEVKRRALEFVDYI
NSKLPGVLELEYEGFYARGFFVTKKKYALIDEEGKIVTRGLEIVRRDWSEIAKETQARVLEAILKHGNVEE
AVKIVKDVTEKLTNYEVPPEKLVIYEQITRPINEYKAIGPHVAVAKRLMARGIKVKPGMVIGYIVLRGDGP
ISKRAISIEEFDPRKHKYDAEYYIENQVLPAVERILKAFGYKREDLRWQKTKQVGLGAWIKVKKS DNA Sequence of wild type *P. horikoshii* OT3 (SEQ ID NO: 2):
*Pyrococcus horikoshii* DNA Polymerase gene
ATGATTCTGGACGCTGATTATATTACTGAAGATGGTAAACCGATTATTCGTATTTTTAAAAAAGAAAA
TGGCGAGTTCAAAGTTGAATATGACCGTAACTTTCGTCCGTACATCTACGCGCTGTTGCGCGACGATA
GCGCGATCGATGAGATTAAGAAAATTACCGCGCAGCGTCATGGTAAAGTTGTTCGCATCGTTGAAACC
GAGAAAATTCAACGTAAATTCCTGGGCCGCCCAATTGAAGTGTGGAAGCTGTACCTGGAGCATCCGCA
AGATGTCCCGGCGATCCGTGACAAGATTCGCGAGCACCCGGCCGTCGTCGACATTTTCGAATACGATA
TTCCGTTCGCAAAGCGTTACCTGATCGATAAGGGTCTGACCCCGATGGAGGGTAATGAAAAGCTGACG
TTCCTGGCTGTCGATATTGAAACGTTGTACCACGAGGGTGAAGAGTTTGGTAAGGGCCCGGTCATTAT
GATCAGCTACGCGGATGAAGAGGGCGCCAAAGTTATCACGTGGAAAAAAATTGATCTGCCGTACGTTG
AAGTTGTGTCCAGCGAGCGCGAGATGATTAAACGCTTGATTCGTGTGATTAAAGAAAAAGATCCAGAC
GTGATCATTACCTATAATGGTGACAACTTTGACTTTCCGTACTTGCTGAAACGTGCTGAGAAACTGGG
TATCAAGCTGTTGCTGGGTCGCGATAATAGCGAGCCGAAGATGCAAAAAATGGGCGATAGCCTGGCAG
TCGAGATCAAGGGTCGCATCCACTTTGATCTCTTTCCGGTGATTCGTCGCACGATCAATCTGCCGACC
TATACGCTGGAAGCTGTCTACGAGGCAATCTTTGGTAAGCCGAAAGAAAAAGTCTATGCGGACGAAAT
TGCGAAAGCGTGGGAAACCGGCGAGGGCCTGGAGCGTGTGGCAAAGTACTCTATGGAAGATGCCAAAG
TGACCTATGAACTGGGTCGTGAGTTCTTCCCAATGGAAGCCCAGTTGGCGCGCTTGGTGGGCCAACCG
GTTTGGGACGTTTCCCGTAGCAGCACCGGTAACCTGGTTGAGTGGTTTCTGTTGCGTAAAGCGTATGA
GCGTAATGAACTGGCACCGAACAAGCCTGACGAGAAAGAATATGAACGTCGCCTGCGTGAATCTTACG
AGGGTGGTTACGTCAAAGAACCGGAAAAGGGTCTGTGGGAAGGCATCGTGAGCCTGGATTTCCGTAGC
CTGTACCCTAGCATCATCATCACGCACAATGTTAGCCCGGACACCCTGAACCGCGAGGGCTGCGAAGA
GTACGACGTTGCGCCGAAAGTCGGCCATCGTTTTTGTAAAGACTTCCCTGGTTTCATCCCAAGCCTGC
TGGGTCAGCTGCTGGAAGAGAGACAGAAAATTAAAAAACGCATGAAAGAATCGAAAGATCCGGTTGAG
AAAAAGCTGCTGGATTACCGCCAGCGTGCCATCAAGATTCTGGCTAACTCATATTATGGCTACTACGG
TTATGCTAAAGCGCGTTGGTACTGTAAAGAGTGCGCGGAGTCCGTCACCGCGTGGGGTCGCCAGTATA
TCGATCTGGTGCGTCGCGAGCTGGAAGCGCGTGGTTTTAAGGTCCTGTACATCGATACTGACGGTCTG
TATGCAACCATCCCTGGTGTCAAAGACTGGGAAGAGGTTAAGCGTCGTGCACTGGAATTTGTGGACTA
TATCAATTCTAAGTTGCCGGGTGTGCTGGAGCTGGAGTACGAAGGCTTCTATGCACGCGGCTTTTTCG
TTACGAAAAAGAAATACGCACTGATCGACGAAGAGGGCAAGATTGTGACTCGTGGTCTGGAAATCGTT
CGTCGCGACTGGAGCGAGATTGCAAAAGAAACCCAAGCTCGCGTTCTGGAAGCAATCCTGAAACATGG
TAACGTCGAAGAAGCCGTCAAGATCGTGAAAGATGTCACCGAAAAGTTGACCAACTACGAAGTTCCAC
CGGAAAAACTGGTGATTTATGAGCAAATCACGCGTCCGATCAATGAATATAAGGCCATTGGCCCGCAC
GTCGCGGTGGCCAAGCGCCTGATGGCGCGTGGTATCAAAGTGAAACCGGGTATGGTTATTGGTTACAT
CGTGCTGCGTGGCGACGGCCCGATTAGCAAACGTGCGATCAGCATTGAAGAATTTGACCCGCGTAAGC
ACAAATATGACGCGGAATACTATATCGAGAATCAAGTGCTGCCGGCCGTGGAACGCATTCTGAAAGCT
TTCGGCTACAAGCGTGAAGATTTGCGCTGGCAGAAAACCAAACAGGTTGGTCTTGGTGCGTGGATCAA
GGTCAAAAAGTCCTAA

*Pyrococcus abyssi* (SEQ ID NO: 3)
MIIDADYITEDGKPIIRIFKKEKGEFKVEYDRTFRPYIYALLKDDSAIDEVKKITAERHGKIVRITEV
EKVQKKFLGRPIEVWKLYLEHPQDVPAIREKIREHPAVVDIFEYDIPFAKRYLIDKGLTPMEGNEELT
FLAVDIETLYHEGEEFGKGPIIMISYADEEGAKVITWKSIDLPYVEVVSSEREMIKRLVKVIREKDPD
VIITYNGDNFDFPYLLKRAEKLGIKLPLGRDNSEPKMQRMGDSLAVEIKGRIHFDLFPVIRRTINLPT
YTLEAVYEAIFGKSKEKVYAHEIAEAWETGKGLERVAKYSMEDAKVTFELGKEFFPMEAQLARLVGQP
VWDVSRSSTGNLVEWFLLRKAYERNELAPNKPDEREYERRLRESYEGGYVKEPEKGLWEGIVSLDFRS
LYPSIIITHNVSPDTLNRENCKEYDVAPQVGHRFCKDFPGFIPSLLGNLLEERQKIKKRMKESKDPVE
KKLLDYRQRAIKILANSYYGYYGYAKARWYCKECAESVTAWGRQYIDLVRRELESRGFKVLYIDTDGL
YATIPGAKHEEIKEKALKFVEYINSKLPGLLELEYEGFYARGFFVTKKKYALIDEEGKIVTRGLEIVR
RDWSEIAKETQAKVLEAILKHGNVDEAVKIVKEVTEKLSKYEIPPEKLVIYEQITRPLSEYKAIGPHV
AVAKRLAAKGVKVKPGMVIGYIVLRGDGPISKRAIAIEEFDPKKHKYDAEYYIENQVLPAVERILRAF
GYRKEDLKYQKTKQVGLGAWLKF

*Pyrococcus woesei* (SEQ ID NO: 4)
MILDVDYITEEGKPVIRLFKKENGKFKIEHDRTFRPYIYALLRDDSKIEEVKKITGERHG
KIVRIVDVEKVEKKFLGKPITVWKLYLEHPQDVPTIREKVREHPAVVDIFEYDIPFAKRY
LIDKGLIPMEGEEELKILAFDIETLYHEGEEFGKGPIIMISYADENEAKVITWKNIDLPY
VEVVSSEREMIKRFLRIIREKDPDIIVTYNGDSFDFPYLAKRAEKLGIKLTIGRDGSEPK
MQRIGDMTAVEVKGRIHFDLYHVITRTINLPTYTLEAVYEAIFGKPKEKVYADEIAKAWE
SGENLERVAKYSMEDAKATYELGKEFLPMEIQLSRLVGQPLWDVSRSSTGNLVEWFLLRK
AYERNEVAPNKPSEEEYQRRLRESYTGGFVKEPEKGLWENIVYLDFRALYPSIIITHNVS
PDTLNLEGCKNYDIAPQVGHKFCKDIPGFIPSLLGHLLEERQKIKTKMKETQDPIEKILL
DYRQKAIKLLANSFYGYYGYAKARWYCKECAESVTAWGRKYIELVWKELEEKFGFKVLYI
DTDGLYATIPGGESEEIKKKALEFVKYINSKLPGLLELEYEGFYKRGFFVTKKRYAVIDE
EGKVITRGLEIVRRDWSEIAKETQARVLETILKHGDVEEAVRIVKEVIQKLANYEIPPEK
LAIYEQITRPLHEYKAIGPHVAVAKKLAAKGVKIKPGMVIGYIVLRGDGPISNRAILAEE
YDPKKHKYDAEYYIENQVLPAVLRILEGFGYRKEDLRYQKTRQVGLTSWLNIKKS -continued

| SEQUENCES |
| --- |

*Pyrococcus furiosus* (SEQ ID NO: 5)
MILDVDYITEEGKPVIRLFKKENGKFKIEHDRTFRPYIYALLRDDSKIEEVKKITGERHGKIVRIVDV
EKVEKKFLGKPITVWKLYLEHPQDVPTIREKVREHPAVVDIFEYDIPFAKRYLIDKGLIPMEGEEELK
ILAFDIETLYHEGEEFGKGPIIMISYADENEAKVITWKNIDLPYVEVVSSEREMIKRFLRIIREKDPD
IIVTYNGDSFDFPYLAKRAEKLGIKLTIGRDGSEPKMQRIGDMTAVEVKGRIHFDLYHVITRTINLPT
YTLEAVYEAIFGKPKEKVYADEIAKAWESGENLERVAKYSMEDAKATYELGKEFLPMEIQLSRLVGQP
LWDVSRSSTGNLVEWFLLRKAYERNEVAPNKPSEEEYQRRLRESYTGGFVKEPEKGLWENIVYLDFRA
LYPSIIITHNVSPDTLNLEGCKNYDIAPQVGHKFCKDIPGFIPSLLGHLLEERQKIKTKMKETQDPIE
KILLDYRQKAIKLLANSFYGYYGYAKARWYCKECAESVTAWGRKYIELVWKELEEKFGFKVLYIDTDG
LYATIPGGESEEIKKKALEFVKYINSKLPGLLELEYEGFYKRGFFVTKKRYAVIDEEGKVITRGLEIV
RRDWSEIAKETQARVLETILKHGDVEEAVRIVKEVIQKLANYEIPPEKLAIYEQITRPLHEYKAIGPH
VAVAKKLAAKGVKIKPGMVIGYIVLRGDGPISNRAILAEEYDPKKHKYDAEYYIENQVLPAVLRILEG
FGYRKEDLRYQKTRQVGLTSWLNIKKS

*Pyrococcus glycovorans* (SEQ ID NO: 6)
MILDADYITEDGKPIIRIFKKENGEFKVEYDRNFRPYIYALLKDDSQIDEVKKITAERHGKIVRIVDVEK
VKKKFLGRPIEVWKLYFEHPQDVPAIRDKIREHPAVVDIFEYDIPFAKRYLIDKGLIPMEGDEELKLLAF
DIETLYHEGEEFAKGPIIMISYADEEGAKVITWKKVDLPYVEVVSSEREMIKRFLKVIREKDPDVIITYN
GDSFDLPYLVKRAEKLGIKLPLGRDGSEPKMQRLGDMTAVEIKGRIHFDLYHVIRRTINLPTYTLEAVYE
AIFGKPKEKVYAHEIAEAWETGKGLERVAKYSMEDAKVTYELGREFFPMEAQLSRLVGQPLWDVSRSSTG
PDTLNREGCMEYDVAPEVKHKFCKDFPGFIPSLLKRLLDERQEIKRRMKASKDPIEKKMLDYRQRAIKIL
ANSYYGYYGYAKARWYCKECAESVTAWGREYIEFVRKELEEKFGFKVLYIDTDGLYATIPGAKPEEIKRK
ALEFVEYINAKLPGLLELEYEGFYVRGFFVTKKKYALIDEEGKIITRGLEIVRRDWSEIAKETQAKVLEA
ILKHGNVEEAVKIVKEVTEKLSKYEIPPEKLVIYEQITRPLHEYKAIGPHVAVAKRLAARGVKVRPGMVI
GYIVLRGDGPISKRAILAEEFDPRKHKYDAEYYIENQVLPAVLRILEAFGYRKEDLRWQKTKQTGLTAWL
NVKKK

*Pyrococcus* sp. NA2 (SEQ ID NO: 7)
MILDADYITEDGKPIIRLFKKENGRFKVEYDRNFRPYIYALLKDDSAIDDVRKITSERHGKVVRVIDV
EKVKKKFLGRPIEVWKLYFEHPQDVPAMRDKIREHPAVIDIFEYDIPFAKRYLIDKGLIPMEGNEELT
FLAVDIETLYHEGEEFGKGPIIMISYADEEGAKVITWKKIDLPYVEVVANEREMIKRLIKVIREKDPD
VIITYNGDNFDFPYLLKRAEKLGMKLPLGRDNSEPKMQRLGDSLAVEIKGRIHFDLFPVIRRTINLPT
YTLEAVYEAIFGKQKEKVYPHEIAEAWETGKGLERVAKYSMEDAKVTYELGKEFFPMEAQLARLVGQP
LWDVSRSSTGNLVEWYLLRKAYERNELAPNKPDEREYERRLRESYEGGYVKEPERGLWEGIVSLDFRS
LYPSIIITHNVSPDTLNKEGCGEYDEAPEVGHRFCKDFPGFIPSLLGSLLEERQKIKKRMKESKDPVE
RKLLDYRQRAIKILANSFYGYYGYAKARWYCKECAESVTAWGRQYIELVRRELEERGFKVLYIDTDGL
YATIPGEKNWEEIKRRALEFVNYINSKLPGILELEYEGFYTRGFFVTKKKYALIDEEGKIVTRGLEIV
RRDWSEIAKETQAKVLEAILKHGNVEEAVKIVKEVTEKLSNYEIPVEKLVIYEQITRPLNEYKAIGPH
VAVAKRLAAKGIKIKPGMVIGYVVLRGDGPISKRAIAIEEFDGKKHKYDAEYYIENQVLPAVERILKA
FGYKREDLRWQKTKQVGLGAWLKVKKS

*Pyrococcus* sp. ST700 (SEQ ID NO: 8)
MILDADYITENGKPIIRLFKKENGKFKVEYDRNFRPYIYALLKDDSAIDDVRKITSERHGKVVRVIDVEK
VSKKFLGRPIEVWKLYFEHPQDVPAIRDKIREHPAVIDIFEYDIPFAKRYLIDKGLIPMEGNEELSFLAV
DIETLYHEGEEFGKGPIIMISYADEEGAKVITWKKIDLPYVEVVANEREMIKRLVRIIREKDPDIIITYN
GDNFDFPYLLKRAEKLGIKLPLGRDNSEPKMQRLGESLAVEIKGRIHFDLFPVIRRTINLPTYTLRTVYE
AIFGKPKEKVYPHEIAEAWETGKGLERVAKYSMEDAKVTYELGKEFFPMEAQLARLVGQPVWDVSRSSTG
NLVEWFLLRKAYERNELAPNKPDEKEYEKRLRESYEGGYVKEPEKGLWEGIVSLDFRSLYPSIIITHNVS
PDTLNREGCGKYDEAPEVGHRFCKDFPGFIPSLLGDLLEERQKIKKRMKESKDPIEKKLLDYRQRAIKIL
ANSFYGYYGYAKARWYCKECAESVTAWGRQYIELVRRELEERGFKVLYIDTDGLYATIPGEKNWEEIKRK
ALEFVNYINSKLPGILELEYEGFYTRGFFVTKKKYALIDEEGKIITRGLEIVRRDWSEIAKETQAKVLEA
ILKHGNVEEAVKIVKEVTEKLSNYEIPVEKLVIYEQITRPLNEYKAIGPHVAVAKRLAAKGIKIKPGMVI
GYVLLRGDGPISKRAIAIEEFDGKKHKYDAEYYIENQVLPAVERILKAFGYKKEDLRWQ

*Pyrococcus kukulkanii* (SEQ ID NO: 9)
MILDADYITEDGKPIIRIFKKENGEFKVEYDRNFRPYIYALLKDDSQIDEVRKITAERHGKIVRIIDA
EKVRKKFLGRPIEVWRLYFEHPQDVPAIRDKIREHSAVIDIFEYDIPFAKRYLIDKGLIPMEGDEELK
LLAFDIETLYHEGEEFAKGPIIMISYADEEEAKVITWKKIDLPYVEVVSSEREMIKRFLKVIREKDPD
VIITYNGDSFDLPYLVKRAEKLGIKLPLGRDGSEPKMQRLGDMTAVEIKGRIHFDLYHVIRRTINLPT
YTLEAVYEAIFGKPKEKVYAHEIAEAWETGKGLERVAKYSMEDAKVTYELGREFFPMEAQLSRLVGQP
LWDVSRSSTGNLVEWYLLRKAYERNELAPNKPDEREYERRLRESYAGGYVKEPEKGLWEGLVSLDFRS
LYPSIIITHNVSPDTLNREGCREYDVAPEVGHKFCKDFPGFIPSLLKRLLDERQEIKRKMKASKDPIE
KKMLDYRQRAIKILANSYYGYYGYAKARWYCKECAESVTAWGREYIEFVRKELEEKFGFKVLYIDTDG
LYATIPGAKPEEIKKKALEFVDYINAKLPGLLELEYEGFYVRGFFVTKKKYALIDEEGKIITRGLEIV
RRDWSEIAKETQAKVLEAILKHGNVEEAVKIVKEVTEKLSKYEIPPEKLVIYEQITRPLHEYKAIGPH
VAVAKRLAARGVKVRPGMVIGYIVLRGDGPISKRAILAEEFDLRKHKYDAEYYIENQVLPAVLRILEA
FGYRKEDLRWQKTKQTGLTAWLNIKKK

*Pyrococcus yayanosii* (SEQ ID NO: 10)
MILDADYITENGKPVVRIFKKENGEFKVEYDRSFRPYIYALLRDDSAIEDIKKITAERHGKVVRVVEA
EKVRKKFLGRPIEVWKLYFEHPQDVPAIREKIREHPAVIDIFEYDIPFAKRYLIDKGLIPMEGNEELK
LLAFDIETLYHEGDEFGSGPIIMISYADEKGAKVITWKGVDLPYVEVVSSEREMIKRFLRVIREKDPD
VIITYNGDNFDFPYLLKRAEKLGMKLPIGRDGSEPKMQRMGDGFAVEVKGRIHFDIYPVIRRTINLPT
YTLEAVYEAVFGRPKEKVYPNEIARAWENCKGLERVAKYSMEDAKVTYELGREFFPMEAQLARLVGQP
VWDVSRSSTGNLVEWFLLRKAYERNELAPNRPDEREYERRLRESYEGGYVKEPEKGLWEGIIYLDFRS
LYPSIIITHNISPDTLNKEGCNSYDVAPKVGHRFCKDFPGFIPSLLGQLLDERQKIKRKMKATIDPIE
RKLLDYRQRAIKILANSYYGYYGYAKARWYCKECAESVTAWGREYIELVSRELEKRGFKVLYIDTDGL -continued

| SEQUENCES |
| --- |
| YATIPGSREWDKIKERALEFVKYINARLPGLLELEYEGFYKRGFFVTKKKYALIDEEGKIITRGLEIV<br>RRDWSEIAKETQARVLEAILKEGNLEKAVKIVKEVTEKLSKYEVPPEKLVIYEQITRDLKDYKAVGPH<br>VAVAKRLAARGIKVRPGMVIGYLVLRGDGPISRRAIPAEEFDPSRHKYDAEYYIENQVLPAVLRILEA<br>FGYRKEDLRYQKTRQAGLDAWLKRKASL |
| *Pyrococcus* sp. ST04 (SEQ ID NO: 11)<br>MILDADYITEDGKPVIRLFKKENGEFKIEYDRTFKPYIYALLKDDSAIDEVRKVTAERHGKIVRIIDV<br>EKVKKKYLGRPIEVWKLYFEHPQDVPAIREKIREHPAVVEIFEYDIPFAKRYLIDKGIVPMDGDEELK<br>LLAFDIETLYHEGEEFGKGPILMISYADEEGAKVITWKRINLPYVEVVSSEREMIKRFLKVIREKDPD<br>VIITYNGDSFDFPYLVKRAEKLGIKLPLGRDGSPPKMQRLGDMNAVEIKGRIHFDLYHVVRRTINLPT<br>YTLEAVYEAIFGKPKEKVYAHEIAEAWETGKGLERVAKYSMEDAQVTYELGKEFFPMEVQLTRLVGQP<br>LYPSIIITHNVSPDTLNREGCRKYDIAPEVGHKFCKDVEGFIPSLLGHLLEERQKIKRKMKATINPVE<br>KKLLDYRQKAIKILANSYYGYYGYAKARWYCKECAESVTAWGREYIELVRKELEGKFGFKVLYIDTDG<br>LYATIPRGDPAEIKKKALEFVRYINEKLPGLLELEYEGFYRRGFFVTKKKYALIDEEDKIITRGLEIV<br>RRDWSEIAKETQAKVLEAILKEGNVEKAVKIVKEVTEKLMKYEVPPEKLVIYEQITRPLNEYKAIGPH<br>VAVAKRLAAKGVKVRPGMVIGYIVLRGDGPISKRAILAEEYDPRKNKYDAEYYIENQVLPAVLRILEA<br>FGYKKEDLKYQKSRQVGLGAWIKVKK |
| *Pyrococcus* sp. GB-D (SEQ ID NO: 12)<br>MILDADYITEDGKPIIRIFKKENGEFKVEYDRNFRPYIYALLKDDSQIDEVRKITAERHGKIVRIIDAEK<br>VRKKFLGRPIEVWRLYFEHPQDVPAIRDKIREHSAVIDIFEYDIPFAKRYLIDKGLIPMEGDEELKLLAF<br>DIETLYHEGEEFAKGPIIMISYADEEEAKVITWKKIDLPYVEVVSSEREMIKRFLKVIREKDPDVIITYN<br>GDSFDLPYLVKRAEKLGIKLPLGRDGSEPKMQRLGDMTAVEIKGRIHFDLYHVIRRTINLPTYTLEAVYE<br>AIFGKPKEKVYAHEIAEAWETGKGLERVAKYSMEDAKVTYELGREFFPMEAQLSRLVGQPLWDVSRSSTG<br>PDTLNREGCREYDVAPEVGHKFCKDFPGFIPSLLKRLLDERQEIKRKMKASKDPIEKKMLDYRQRAIKIL<br>ANSYYGYYGYAKARWYCKECAESVTAWGREYIEFVRKELEEKFGFKVLYIDTDGLYATIPGAKPEEIKKK<br>ALEFVDYINAKLPGLLELEYEGFYVRGFFVTKKKYALIDEEGKIITRGLEIVRRDWSEIAKETQAKVLEA<br>ILKHGNVEEAVKIVKEVTEKLSKYEIPPEKLVIYEQITRPLHEYKAIGPHVAVAKRLAARGVKVRPGMVI<br>GYIVLRGDGPISKRAILAEEFDLRKHKYDAEYYIENQVLPAVLRILEAFGYRKEDLRWQKTKQTGLTAWL<br>NIKKK |

EMBODIMENTS

Embodiment 1. A polymerase comprising an amino acid sequence that is at least 80% identical to a continuous 500 amino acid sequence within SEQ ID NO: 1; comprising a first mutation at amino acid position 7 or an amino acid position corresponding to position 7, wherein the mutation is histidine, lysine, or arginine; and a second mutation at amino acid position 588 or an amino acid position corresponding to position 588; wherein the second mutation comprises leucine, isoleucine, valine, alanine, or glycine.

Embodiment 2. The polymerase of Embodiment 1, wherein the first mutation is histidine.

Embodiment 3. The polymerase of Embodiments 1 or 2, comprising a mutation at amino acid position 76 or an amino acid position corresponding to amino acid position 76, wherein the mutation is proline, histidine, arginine, or glycine.

Embodiment 4. The polymerase of any one of Embodiments 1 to 3, comprising a mutation at amino acid position 76 or an amino acid position corresponding to amino acid position 76, wherein the mutation is proline, histidine, or glycine.

Embodiment 5. The polymerase of any one of Embodiments 1 to 4, comprising a mutation at amino acid position 742 or an amino acid position corresponding to position 742, wherein the mutation is leucine, isoleucine, alanine, or glycine.

Embodiment 6. The polymerase of any one of Embodiments 1 to 4, comprising a mutation at amino acid position 742 or an amino acid position corresponding to position 742, wherein the mutation is alanine or glycine.

Embodiment 7. The polymerase of any one of Embodiments 1 to 6, comprising a mutation at amino acid position 13 or an amino acid position corresponding to position 13, wherein the mutation is arginine or histidine.

Embodiment 8. The polymerase of any one of Embodiments 1 to 6, comprising a mutation at amino acid position 13 or an amino acid position corresponding to position 13, wherein the mutation is arginine.

Embodiment 9. The polymerase of any one of Embodiments 1 to 8, comprising a mutation at amino acid position 397 or an amino acid position corresponding to position 397, wherein the mutation is methionine, cysteine, isoleucine, valine, or alanine.

Embodiment 10. The polymerase of any one of Embodiments 1 to 8, comprising a mutation at amino acid position 397 or an amino acid position corresponding to position 397, wherein the mutation is methionine, valine, or alanine.

Embodiment 11. A polymerase comprising an amino acid sequence that is at least 80% identical to a continuous 500 amino acid sequence within SEQ ID NO: 1; comprising a first mutation at amino acid position 97 or an amino acid position corresponding to position 97, wherein the first mutation comprises cysteine, histidine, lysine, serine, threonine, or methionine; and a second mutation at amino acid position 588 or an amino acid position corresponding to position 588; wherein the second mutation comprises leucine, isoleucine, valine, alanine, or glycine.

Embodiment 12. The polymerase of Embodiment 1, wherein the first mutation is cysteine, histidine, or serine.

Embodiment 13. The polymerase of any one of Embodiments 1 to 12, wherein the second mutation is leucine, isoleucine, valine, or alanine.

Embodiment 14. The polymerase of Embodiment any one of Embodiments 11 to 13, comprising a mutation at amino acid position 742 or an amino acid position corresponding to position 742, wherein the mutation is leucine, isoleucine, alanine, or glycine.

Embodiment 15. The polymerase of Embodiment any one of Embodiments 11 to 13, comprising a mutation at amino acid position 742 or an amino acid position corresponding to position 742, wherein the mutation is alanine or glycine.

Embodiment 16. The polymerase of Embodiment any one of Embodiments 1 to 15, comprising a mutation at amino acid position 726 or an amino acid position corresponding to amino acid position 726, wherein the mutation is aspartic acid, glutamic acid, asparagine, or glutamine.

Embodiment 17. The polymerase of Embodiment any one of Embodiments 1 to 16, comprising a mutation at amino acid position 769 or an amino acid position corresponding to position 769, wherein the mutation is leucine, isoleucine, valine, alanine, or glycine.

Embodiment 18. The polymerase of Embodiment any one of Embodiments 11 to 17, comprising a mutation at amino acid position 7 or an amino acid position corresponding to position 7, wherein the mutation is histidine, lysine, or arginine.

Embodiment 19. The polymerase of Embodiment any one of Embodiments 1 to 18, comprising a mutation at amino acid position 13 or an amino acid position corresponding to position 13, wherein the mutation is arginine, leucine, isoleucine, or histidine.

Embodiment 20. The polymerase of Embodiment any one of Embodiments 1 to 19, comprising a mutation at amino acid position 241 or an amino acid position corresponding to position 241, wherein the mutation is leucine, isoleucine, alanine, valine, or glycine.

Embodiment 21. The polymerase of Embodiment any one of Embodiments 1 to 20, comprising a mutation at amino acid position 472 or an amino acid position corresponding to position 472, wherein the mutation is asparagine, aspartic acid, glutamic acid, or glutamine.

Embodiment 22. The polymerase of Embodiment any one of Embodiments 1 to 20, comprising a mutation at amino acid position 472 or an amino acid position corresponding to position 472, wherein the mutation is asparagine or glutamic acid.

Embodiment 23. The polymerase of Embodiment any one of Embodiments 1 to 22, comprising a mutation at amino acid position 469 or an amino acid position corresponding to position 469, wherein the mutation is threonine, serine, cysteine, or methionine.

Embodiment 24. The polymerase of Embodiment any one of Embodiments 1 to 22, comprising a mutation at amino acid position 469 or an amino acid position corresponding to position 469, wherein the mutation is asparagine, aspartic acid, glutamic acid, or glutamine.

Embodiment 25. The polymerase of Embodiment any one of Embodiments 1 to 24, comprising: a mutation at amino acid position 520 or an amino acid position corresponding to position 520, wherein the mutation is histidine, lysine, or arginine; a mutation at amino acid position 465 or an amino acid position corresponding to position 465, wherein the mutation is asparagine, aspartic acid, glutamic acid, or glutamine; and/or a mutation at amino acid position 491 or an amino acid position corresponding to position 491, wherein the mutation is glycine, valine, leucine, or isoleucine.

Embodiment 26. The polymerase of Embodiment any one of Embodiments 1 to 25, comprising a glutamine, valine, arginine, or alanine at amino acid position 93 or an amino acid position corresponding to position 93.

Embodiment 27. The polymerase of Embodiment any one of Embodiments 1 to 26, comprising an alanine at amino acid position 141 or an amino acid position corresponding to position 141; and an alanine at amino acid position 143 or an amino acid position corresponding to position 143.

Embodiment 28. A method of incorporating a nucleotide into a nucleic acid sequence comprising combining in a reaction vessel: (i) a nucleic acid template, (ii) a nucleotide solution, and (iii) a polymerase, wherein the polymerase is a polymerase of Embodiment any one of Embodiments 1 to 27.

Embodiment 29. A method of amplifying a nucleic acid sequence comprising: a. hybridizing a nucleic acid template with a primer to form a primer-template hybridization complex; b contacting the primer-template hybridization complex with a DNA polymerase and a plurality of nucleotides, wherein the DNA polymerase is the polymerase of Embodiment any one of Embodiments 1 to 27; c incorporating one or more nucleotides into the primer-template hybridization complex with the DNA polymerase to generate amplification products, thereby amplifying a nucleic acid sequence.

Embodiment 30. A kit comprising a polymerases of any one of embodiments 1 to 27.

Embodiment 31. A polymerase comprising an amino acid sequence that is at least 80% identical to a continuous 500 amino acid sequence within SEQ ID NO: 1; comprising a first mutation at amino acid position 588 or an amino acid position corresponding to position 588; wherein the first mutation is leucine, isoleucine, valine, alanine, or glycine; and a second mutation at amino acid position 7 or an amino acid position corresponding to position 7, wherein the mutation is histidine, lysine, or arginine; at amino acid position 97 or an amino acid position corresponding to position 97, wherein the mutation is cysteine, histidine, lysine, serine, threonine, or methionine; or at amino acid position 742 or an amino acid position corresponding to position 742, wherein the mutation is leucine, isoleucine, alanine, or glycine.

Embodiment 32. The polymerase of Embodiment 31, wherein the second mutation is a mutation at amino acid position 7 or an amino acid position corresponding to position 7, wherein the mutation is histidine, lysine, or arginine.

Embodiment 33. The polymerase of Embodiment 32, further comprising a mutation at amino acid position 742 or an amino acid position corresponding to position 742, wherein the mutation is leucine, isoleucine, alanine, or glycine.

Embodiment 34. The polymerase of Embodiment 31, wherein the second mutation is a mutation at amino acid position 97 or an amino acid position corresponding to position 97, wherein the mutation is cysteine, histidine, lysine, serine, threonine, or methionine.

Embodiment 35. The polymerase of Embodiment 34, further comprising a mutation at amino acid position 742 or an amino acid position corresponding to position 742, wherein the mutation is leucine, isoleucine, alanine, or glycine.

Embodiment 36. The polymerase of Embodiment 31, wherein the second mutation is a mutation at amino acid position 742 or an amino acid position corresponding to position 742, wherein the mutation is leucine, isoleucine, alanine, or glycine.

Embodiment 37. The polymerase of any one of Embodiments 31 to 36, comprising a mutation at amino acid position 13 or an amino acid position corresponding to position 13, wherein the mutation is arginine, isoleucine, methionine, or histidine.

Embodiment 38. The polymerase of Embodiment 31, wherein the second mutation is a mutation at amino acid position 97 or an amino acid position corresponding to position 97, wherein the mutation is cysteine or histidine.

Embodiment 39. The polymerase of any one of Embodiments 31 to 38, wherein the first mutation is leucine, isoleucine, valine, or alanine.

Embodiment 40. The polymerase of any one of Embodiments 31 to 38, wherein the first mutation is leucine or valine.

Embodiment 41. The polymerase of any one of Embodiments 31 to 40, comprising a mutation at amino acid position 579 or an amino acid position corresponding to position 579, wherein the mutation is alanine or glycine.

Embodiment 42. The polymerase of any one of Embodiments 31 to 41, comprising a mutation at amino acid position 726 or an amino acid position corresponding to amino acid position 726, wherein the mutation is aspartic acid, glutamic acid, asparagine, or glutamine.

Embodiment 43. The polymerase of any one of Embodiments 31 to 42, comprising a mutation at amino acid position 13 or an amino acid position corresponding to position 13, wherein the mutation is arginine, leucine, isoleucine, or histidine.

Embodiment 44. The polymerase of any one of Embodiments 31 to 43, comprising: a mutation at amino acid position 13 or an amino acid position corresponding to position 13, wherein the mutation is arginine, leucine, isoleucine, or histidine; and a mutation at amino acid position 579 or an amino acid position corresponding to position 579, wherein the mutation is alanine or glycine.

Embodiment 45. The polymerase of Embodiment 31, comprising: R97H, F588L, G635D, and V742A; K13R, R97C, E579G, and F588L; R97C, E563G, E579G, F588L, and V742A; R97H, F588L, and G635D; R97C, F588L, and V742A; Y7H, K13I, R97L, E579G, F588L, and V742A; Y7H, K13R, R97H, and V742A; 7H, K13R, R97C, D141A, E579G, F588L, and V742A; R97C, E579G, F588L, and V742A; Y7H, R97C, E579G, and F588L; Y7H, R97C, and V742A; or Y7H, K13R, E563G, F588L, and V742A.

Embodiment 46. The polymerase of Embodiment 31, comprising: E29D, Y30F, R97H, I160V, K229E, A511V, I548V, F588L, G635D, and V742A; K13R, R32H, F75L, R97C, K201I, Y209H, I256V, Y291H, E383D, G400D, R526C, E579G, F588L, E638G, and A730V; F75L, R97C, I142T, V278I, A281T, A292E, M329L, P372S, H440N, E563G, E579G, F588L, D729Y, and V742A; I65V, R97H, F283S, V308M, K465E, F588L, T591A, I604M, G635D, and K727T; E25K, R97C, A168T, R255H, F326Y, K478R, R526H, E556K, K558N, P573S, E581N, F588L, E600K, E601K, R686H, R724H, V742A, K752E, and K762N; Y7H, K13I, F75L, R97L, I160V, V170I, A316P, K469E, A491V, E579G, F588L, V637D, H726D, and V742A; Y7H, K13R, A40V, R97H, F116L, A117S, K154E, A281T, I415V, K477I, K552N, $N_{569}S$, E577K, A585G, F588I, E655D, and V742A; Y7H, K13R, I38F, A40V, R97C, D141A, P286L, G350S, R467C, and K469T, E579G, F588L, F721Y, H726D, V742A, L756C, R757A, W758G, Q759R, T761P, K762N, Q763R, V764L, and G765V; V63A, F75L, R97C, D98G, R188H, F214I, G245S, D246E, T319I, G350S, E579G, F588L, R690H, H726D, V742A, and K760N; Y7H, 118V, R97C, A168S, F214S, G284S, P286Q, A292V, G304D, K391I, E431D, K477I, Y567H, E579G, F588L, and H726D; Y7H, I8V, $N_{23}D$, V66A, F75L, R97C, P217Q, A298S, A316P, K465E, R526H, E577K, E601D, T606I, E655D, R706C, V742A, and W769S; or Y7H, K13R, L76P, K192E, K289T, R364C, L397M, Q484H, E563G, F588L, V637D, R706H, V742A, and L766P.

Embodiment 47. The polymerase of any one of Embodiments 31 to 46, comprising an alanine at amino acid position 141 or an amino acid position corresponding to position 141; and an alanine at amino acid position 143 or an amino acid position corresponding to position 143.

Embodiment 48. A method of incorporating a nucleotide into a nucleic acid sequence comprising combining in a reaction vessel: (i) a nucleic acid template, (ii) a nucleotide solution, and (iii) a polymerase, wherein the polymerase is a polymerase of any one of Embodiments 31 to 47.

Embodiment 49. A method of amplifying a nucleic acid sequence comprising: hybridizing a nucleic acid template with a primer to form a primer-template hybridization complex; b. contacting the primer-template hybridization complex with a DNA polymerase and a plurality of nucleotides, wherein the DNA polymerase is the polymerase of any one of Embodiments 31 to 47; c. incorporating one or more nucleotides into the primer-template hybridization complex with the DNA polymerase to generate amplification products, thereby amplifying a nucleic acid sequence.

Embodiment 50. A kit comprising the polymerase of any one of Embodiments 31 to 47.

What is claimed is:

1. A polymerase comprising an amino acid sequence that is at least 80% identical to a contiguous 500 amino acid sequence within SEQ ID NO: 1; comprising a first substitution at amino acid position 588 or an amino acid position corresponding to position 588; wherein the first substitution is leucine, isoleucine, valine, alanine, or glycine; and a second substitution:

at amino acid position 7 or an amino acid position corresponding to position 7, wherein the second substitution is histidine, lysine, or arginine;

at amino acid position 97 or an amino acid position corresponding to position 97, wherein the second substitution is cysteine, histidine, lysine, serine, threonine, or methionine; or at amino acid position 742 or an amino acid position corresponding to position 742, wherein the second substitution is leucine, isoleucine, alanine, or glycine.

2. The polymerase of claim 1, wherein the second substitution is a substitution at amino acid position 7 or an amino acid position corresponding to position 7, wherein the substitution is histidine, lysine, or arginine.

3. The polymerase of claim 2, further comprising a substitution at amino acid position 742 or an amino acid position corresponding to position 742, wherein the substitution is leucine, isoleucine, alanine, or glycine.

4. The polymerase of claim 1, wherein the second substitution is a substitution at amino acid position 97 or an amino acid position corresponding to position 97, wherein the substitution is cysteine, histidine, lysine, serine, threonine, or methionine.

5. The polymerase of claim 4, further comprising a substitution at amino acid position 742 or an amino acid position corresponding to position 742, wherein the substitution is leucine, isoleucine, alanine, or glycine.

6. The polymerase of claim 1, wherein the second substitution is a substitution at amino acid position 742 or an amino acid position corresponding to position 742, wherein the substitution is leucine, isoleucine, alanine, or glycine.

7. The polymerase of claim 1, comprising a substitution at amino acid position 13 or an amino acid position corresponding to position 13, wherein the substitution is arginine, isoleucine, methionine, or histidine.

8. The polymerase of claim 1, wherein the second substitution is a substitution at amino acid position 97 or an amino acid position corresponding to position 97, wherein the substitution is cysteine or histidine.

9. The polymerase of claim 1, wherein the first substitution is leucine, isoleucine, valine, or alanine.

10. The polymerase of claim 1, wherein the first substitution is leucine or valine.

11. The polymerase of claim 1, comprising a substitution at amino acid position 579 or an amino acid position corresponding to position 579, wherein the substitution is alanine or glycine.

12. The polymerase of claim 1, comprising a substitution at amino acid position 726 or an amino acid position corresponding to amino acid position 726, wherein the substitution is aspartic acid, glutamic acid, asparagine, or glutamine.

13. The polymerase of claim 1, comprising a substitution at amino acid position 13 or an amino acid position corresponding to position 13, wherein the substitution is arginine, leucine, isoleucine, or histidine.

14. The polymerase of claim 1, comprising:

a substitution at amino acid position 13 or an amino acid position corresponding to position 13, wherein the substitution is arginine, leucine, isoleucine, or histidine; and a substitution at amino acid position 579 or an amino acid position corresponding to position 579, wherein the substitution is alanine or glycine.

15. The polymerase of claim 1, comprising:

R97H, F588L, G635D, and V742A;

K13R, R97C, E579G, and F588L;

R97C, E563G, E579G, F588L, and V742A;

R97H, F588L, and G635D;

R97C, F588L, and V742A;

Y7H, K13I, E579G, F588L, and V742A;

Y7H, K13R, R97H, and V742A;

Y7H, K13R, R97C, D141A, E579G, F588L, and V742A;

R97C, E579G, F588L, and V742A;

Y7H, R97C, E579G, and F588L;

Y7H, R97C, and V742A; or

Y7H, K13R, E563G, F588L, and V742A.

16. The polymerase of claim 1, comprising:

E29D, Y30F, R97H, I160V, K229E, A511V, 1548V, F588L, G635D, and V742A;

K13R, R32H, F75L, R97C, K201I, Y209H, 1256V, Y291H, E383D, G400D, R526C, E579G, F588L, E638G, and A730V;

F75L, R97C, I142T, V278I, A281T, A292E, M329L, P372S, H440N, E563G, E579G, F588L, D729Y, and V742A;

I65V, R97H, F283S, V308M, K465E, F588L, T591A, I604M, G635D, and K727T;

E25K, R97C, A168T, R255H, F326Y, K478R, R526H, E556K, K558N, P573S, E581N, F588L, E600K, E601K, R686H, R724H, V742A, K752E, and K762N;

Y7H, K13I, F75L, R97L, I160V, V170I, A316P, K469E, A491V, E579G, F588L, V637D, H726D, and V742A;

Y7H, K13R, A40V, R97H, F116L, A117S, K154E, A281T, I415V, K477I, K552N, N569S, E577K, A585G, F588I, E655D, and V742A;

Y7H, K13R, I38F, A40V, R97C, D141A, P286L, G350S, R467C, and K469T, E579G, F588L, F721Y, H726D, V742A, L756C, R757A, W758G, Q759R, T761P, K762N, Q763R, V764L, and G765V;

V63A, F75L, R97C, D98G, R188H, F214I, G245S, D246E, T319I, G350S, E579G, F588L, R690H, H726D, V742A, and K760N;

Y7H, I18V, R97C, A168S, F214S, G284S, P286Q, A292V, G304D, K391I, E431D, K477I, Y567H, E579G, F588L, and H726D;

Y7H, 18V, N23D, V66A, F75L, R97C, P217Q, A298S, A316P, K465E, R526H, E577K, E601D, T606I, E655D, R706C, V742A, and W769S; or Y7H, K13R, L76P, K192E, K289T, R364C, L397M, Q484H, E563G, F588L, V637D, R706H, V742A, and L766P.

17. The polymerase of claim 1, further comprising an alanine at amino acid position 141 or an amino acid position corresponding to position 141; and an alanine at amino acid position 143 or an amino acid position corresponding to position 143.

18. A method of incorporating a nucleotide into a nucleic acid sequence comprising combining in a reaction vessel: (i) a nucleic acid template, (ii) a nucleotide solution, and (iii) a polymerase, wherein the polymerase is a polymerase of claim 1.

19. A method of amplifying a nucleic acid sequence comprising:

a. hybridizing a nucleic acid template with a primer to form a primer-template hybridization complex;

b. contacting the primer-template hybridization complex with a DNA polymerase and a plurality of nucleotides, wherein the DNA polymerase is the polymerase of claim 1;

c. incorporating one or more nucleotides into the primer-template hybridization complex with the DNA polymerase to generate amplification products, thereby amplifying a nucleic acid sequence.

20. A kit comprising the polymerase of claim 1.

21. The polymerase of claim 1, comprising an amino acid sequence that is 85% identical to SEQ ID NO: 1.

* * * * *